US010285984B2

(12) United States Patent
Zhao et al.

(10) Patent No.: US 10,285,984 B2
(45) Date of Patent: May 14, 2019

(54) METHODS AND COMPOSITIONS FOR IMPROVING GUT MICROBIOTA POPULATION

(71) Applicants: SHANGHAI JIAO TONG UNIVERSITY, Shanghai (CN); PERFECT (CHINA) CO., LTD, Zhongshan (CN)

(72) Inventors: Liping Zhao, Shanghai (CN); Xu Zhang, Shanghai (CN); Menghui Zhang, Shanghai (CN); Yufeng Zhao, Shanghai (CN); Xiaoyan Pang, Shanghai (CN); Xiaojun Zhang, Shanghai (CN); Linghua Wang, Shanghai (CN); Guang Ning, Shanghai (CN); Xiaoying Li, Shanghai (CN); Yifei Zhang, Shanghai (CN)

(73) Assignee: Shanghai Jiao Tong University, Shanghai (CN)

( * ) Notice: Subject to any disclaimer, the term of this patent is extended or adjusted under 35 U.S.C. 154(b) by 783 days.

(21) Appl. No.: 14/405,874

(22) PCT Filed: Jun. 4, 2013

(86) PCT No.: PCT/CN2013/076709
§ 371 (c)(1),
(2) Date: Dec. 5, 2014

(87) PCT Pub. No.: WO2013/182038
PCT Pub. Date: Dec. 12, 2013

(65) Prior Publication Data
US 2015/0119415 A1 Apr. 30, 2015

(30) Foreign Application Priority Data

Jun. 6, 2012 (CN) .......................... 2012 1 0185004

(51) Int. Cl.
| A61K 36/71 | (2006.01) |
| A61K 36/718 | (2006.01) |
| A61K 31/4375 | (2006.01) |
| A61K 36/756 | (2006.01) |
| A61K 36/8964 | (2006.01) |
| A61K 36/185 | (2006.01) |
| A61K 36/288 | (2006.01) |
| A61K 36/29 | (2006.01) |
| A61K 36/42 | (2006.01) |
| A61K 36/489 | (2006.01) |
| A61K 36/515 | (2006.01) |
| A61K 36/539 | (2006.01) |
| A61K 36/708 | (2006.01) |
| A61K 36/744 | (2006.01) |
| A61K 36/75 | (2006.01) |
| A61K 36/88 | (2006.01) |
| A61K 35/74 | (2015.01) |

(Continued)

(52) U.S. Cl.
CPC ........ *A61K 31/4375* (2013.01); *A23L 33/105* (2016.08); *A23L 33/30* (2016.08); *A61K 35/74* (2013.01); *A61K 35/741* (2013.01); *A61K 35/745* (2013.01); *A61K 36/185* (2013.01); *A61K 36/28* (2013.01); *A61K 36/288* (2013.01); *A61K 36/29* (2013.01); *A61K 36/42* (2013.01); *A61K 36/48* (2013.01); *A61K 36/489* (2013.01); *A61K 36/515* (2013.01); *A61K 36/53* (2013.01); *A61K 36/539* (2013.01); *A61K 36/59* (2013.01); *A61K 36/70* (2013.01); *A61K 36/708* (2013.01); *A61K 36/71* (2013.01); *A61K 36/718* (2013.01); *A61K 36/74* (2013.01); *A61K 36/744* (2013.01); *A61K 36/75* (2013.01); *A61K 36/756* (2013.01); *A61K 36/88* (2013.01); *A61K 36/8964* (2013.01); *C12Q 1/689* (2013.01); *G01N 33/5088* (2013.01); *A23V 2002/00* (2013.01); *C12Q 2600/136* (2013.01); *G01N 2500/10* (2013.01)

(58) Field of Classification Search
CPC .. A61K 31/4375; A61K 35/74; A61K 35/741; A61K 35/745; A61K 2300/00; A61K 36/185; A61K 36/28; A61K 36/288; A61K 36/29; A61K 36/42; A61K 36/48; A61K 36/489; A61K 36/515; A61K 36/53; A61K 36/539; A61K 36/59; A61K 36/70; A61K 36/708; A61K 36/71; A61K 36/718; A61K 36/74; A61K 36/744; A61K 36/75; A61K 36/756; A61K 36/88; A61K 36/8964; A23L 33/105; A23L 33/30; A23V 2002/00; C12Q 1/689; C12Q 2600/136; G01N 2500/10; G01N 33/05

See application file for complete search history.

(56) References Cited

FOREIGN PATENT DOCUMENTS

CN 101291597 A 10/2008

OTHER PUBLICATIONS

Cayman Chemical "Berberine" cayman catalog (url: https://www.caymanchem.com/product/10006427), May 27, 2005, 6 pages.*
Tang J, et al "Berberine and Coptidis Rhizoma as novel antineoplastic agents: A review of traditional use and biomedical investigations" Journal of Ethnopharmacology,2009,126,p. 5-17. doi:10.1016/j.jep.2009.08.009.*

(Continued)

*Primary Examiner* — Aaron J Kosar
(74) *Attorney, Agent, or Firm* — Zhihua Han

(57) ABSTRACT

A method and a composition for improving gut micro biota structure, selectively increase a first gut microbiota population while simultaneously decrease a second gut micro biota population in a subject. The first gut micro biota population includes a short-chain fatty acid (SCFA)-producing bacterium and the second gut microbiota population includes an endotoxin-producing bacterium.

3 Claims, 6 Drawing Sheets
Specification includes a Sequence Listing.

(51) Int. Cl.

| | |
|---|---|
| *A61K 35/741* | (2015.01) |
| *A61K 35/745* | (2015.01) |
| *A61K 36/28* | (2006.01) |
| *A61K 36/48* | (2006.01) |
| *A61K 36/53* | (2006.01) |
| *A61K 36/59* | (2006.01) |
| *A61K 36/70* | (2006.01) |
| *A61K 36/74* | (2006.01) |
| *C12Q 1/689* | (2018.01) |
| *G01N 33/50* | (2006.01) |
| *A23L 33/00* | (2016.01) |
| *A23L 33/105* | (2016.01) |

(56) References Cited

OTHER PUBLICATIONS

IDS document 1 OA1 of PI 2014703639.
IDS document 2 English translation of OA1 of MXa2014014789.
IDS document 3 OA1 of MXa2014014789.
IDS document 4 OA2 of MXa2014014789.
IDS document 5 English translation of OA2.of MXa2014014789.
IDS document 6 OA5 of CN2012101850042.
IDS document 7 English translation of OA5 of CN2012101850042.
IDS document 8 rejection of CN2012101850042.
IDS document 9 English translation of rejection of CN2012101850042.

\* cited by examiner

METHODS AND COMPOSITIONS FOR IMPROVING GUT MICROBIOTA POPULATION

CROSS REFERENCE TO RELATED APPLICATIONS

This application is a national stage application of International application number PCT/CN2013/076709, filed Jun. 4 2013, titled "Methods and Compositions for Improving Gut Microbiota Population," which claims the benefit of the filing date of Chinese Patent Application No. 201210185004.2 filed Jun. 6, 2012, the entire disclosure of which is incorporated by reference herein.

SEQUENCE LISTING

The Sequence Listing associated with this application is provided in text format in lieu of a paper copy, and is hereby incorporated by reference into the specification. The name of the text file containing the Sequence Listing is Sequence listing.txt. The text file is about 87 KB, was created on Dec. 18, 2014, and is being submitted electronically via EFS-Web.

TECHNICAL FIELD

The present application relates to compositions and methods for improving gut microbiota populations and related application in drugs, nutritional supplements, health care products, food and beverage.

BACKGROUND

Unless otherwise indicated herein, the materials described in this section are not prior art to the claims in this application and are not admitted to be prior art by inclusion in this section.

Inside the human body lives a large number of symbiotic microbes, among which the gut microbiota acts asan important environmental factor to host health. There are more than 1000 species of bacteria, whose number exceeds 10 folds of the number of human cells, and whose gene number is about 150 folds of that in human cells. In this context, the human body as a "superorganism" made of host cells and symbioticmicrobes including gut microbiota, and the genome encoding a consortium of gut microbes (microbiome) is considered as the second human genome, also known as "humanmetagenome". When human health status changes, the composition of symbioticmicrobes changes accordingly. Conversely, changes in the composition of symbioticmicrobes lead to the change in the human health status. Together, the diversity in human genome and the genome of gut microbiome affects immunity, nutrition, metabolism, and the health and disease status of the human host. However, up to now, it is not clear by what mechanisms the gut microbiota contribute to disease etiology and pathology, which type of bacteria is positively correlated with the health status of the host, and which type of bacteria is negatively correlated with the health status of the host.

SUMMARY

The following summary is illustrative only and is not intended to be in any way limiting. In addition to the illustrative aspects, embodiments, and features described above, further aspects, embodiments, and features will become apparent by reference to the drawings and the following detailed description.

In one aspect, the application provides methods for improving gut microbiota population. In one embodiment, the method includes administering to a subject a composition to increase a first gut microbiota population while simultaneously decrease a second gut microbiota population in the subject. The first gut microbiota population may include a short-chain fatty acid (SCFA)-producing bacteria. The second gut microbiota population may include an endotoxin-producing bacterium.

In another aspect, the application provides methods for screening a test compound that may be active in improving gut microbiota population. In one embodiment, the method includes administering to a control subject an effective amount of a control composition to increase a first gut microbiota population while simultaneously decrease a second gut microbiota population in the control subject, administering to a test subject an amount of a test compound, and comparing the gut microbiota population of the controlled subject with the gut microbiota population of the test subject. A similarity of at least about 80% is indicative that the test compound is active in improving gut microbiota population. The first gut microbiota population may include a short-chain fatty acid (SCFA)-producing bacteria. The second gut microbiota population may include an endotoxin-producing bacterium.

In a further aspect, the application provides compositions for improving gut microbiota population. In one embodiment, the composition is capable of selectively increasing a first gut microbiota population while simultaneously decreasing a second gut microbiota population in a subject. The first gut microbiota population may include a short-chain fatty acid (SCFA)-producing bacteria. The second gut microbiota population may include an endotoxin-producing bacterium. In one embodiment, the composition is administered to the subject at a dosage of from about 50 mg/kg body weight to about 400 mg/body weight and with once a day administration for at least two weeks.

BRIEF DESCRIPTION OF THE DRAWINGS

The foregoing and other features of this disclosure will become more fully apparent from the following description and appended claims, taken in conjunction with the accompanying drawings. Understanding that these drawings depict only several embodiments arranged in accordance with the disclosure and are, therefore, not to be considered limiting of its scope, the disclosure will be described with additional specificity and detail through use of the accompanying drawings, in which:

FIG. 1A is the PCoA score plot of changes in the rat gut microbiota structure in response to HFD feeding and berberine administration; FIG. 1B shows the clustering of the gut microbiota based on mahalanobis distances calculated using MANOVA; and FIG. 1C shows the Shannon-Wiener index, calculated after rarefying to an equal number of sequence reads for all samples;

FIG. 3A shows the levels of total short-chain fatty acids (SCFAs); FIG. 3B shows the level of acetic acid; FIG. 3C shows the level of propionic acid; and FIG. 3D shows the level of butyric acid (D);

FIG. 4A shows the effect of berberine on the body weight gain; FIG. 4B shows the effect of berberine on the adiposity index, calculated as the fat pad weight (sum of epididymal and perirenal fat pads) per 100 g of total body weight; and FIG. 4C shows the food intake of rats during the entire trial;

FIG. 5A shows the effect of berberine on fasting blood glucose (FBG); FIG. 5B shows the effect of berberine on fasting serum insulin (FINS); FIG. 5C shows the effect of berberine onhomeostasis assessment of insulin resistance (HOMA-IR) value, calculated according to the formula fasting insulin (μU/mL)×fasting glucose (mmol/L)/22.5; FIG. 5D shows the effect of berberine onoral glucose tolerance test (OGTT); and FIG. 5E shows the effect of berberine onintra-peritoneal insulin tolerance test (ITT); FIG. 6A shows the effect of berberine onserum lipopolysaccharide (LPS)-binding protein (LBP); FIG. 6B shows the effect of berberine onserum leptin; FIG. 6C shows the effect of berberine onserum MCP-1; and FIG. 6D shows the effect of berberine onserum adiponectin corrected for body fat.

DETAILED DESCRIPTION

Figure 1:
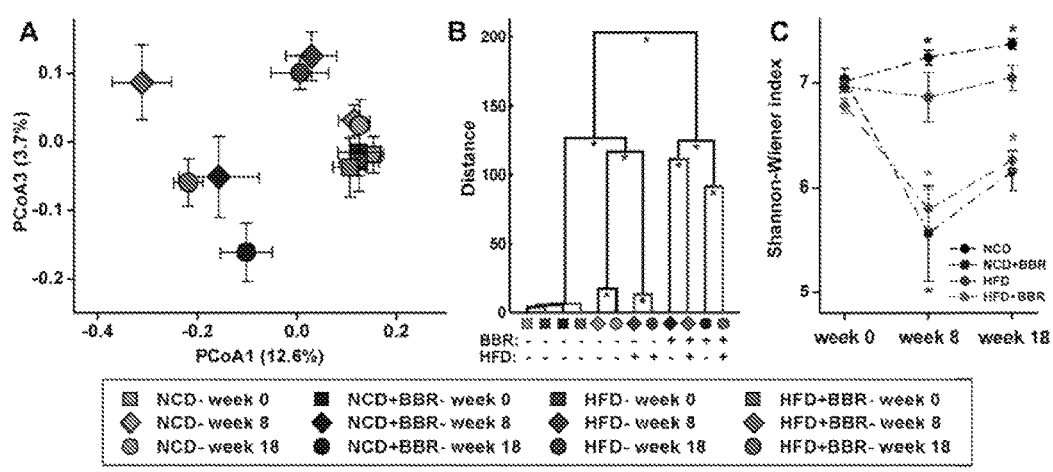
FIG. 1 illustrates the effect of berberine on the rat gut microbiota structure.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

This application is generally drawn, inter alia, to compositions, methods, processes, apparatus, systems, devices, and/or products related to improving gut microbiota population.

The application provides novel compositions and methods for improving gut microbiota population. The application identifies bacteria families that are closely related to host metabolism utilizing, for example, high throughput sequencing and multivariate statistical methods.

In one aspect, the application provides methods for improving gut microbiota population. In one embodiment, the method may include selectively enriching a first gut microbiota population. The first gut microbiota population may include, for example, an short-chain fatty acid (SCFA)-producing bacterium. In one embodiment, the method may include suppressing a second gut microbiota population. The second gut microbiota population may include, for example, an endotoxin-producing bacterium.

In one embodiment, the method may include the step of administering to a subject a composition. The composition may be an oral or parenteral formulation. The composition may selectively increase the first gut microbiota population while simultaneously decrease the second gut microbiota population.

The enrichment of the first gut microbiota population and suppression of the second microbiota population may be carried out simultaneously. The method may result in the prevention or treatment of metabolic syndrome including, without limitation, obesity, diabetes mellitus, insulin resistance, hyperlipoproteinemia, hyperuricemia, hepatic steatosis, hypercholesterolemia, hypertriglyceridemia, inflammation, and other disorders.

The short-chain fatty acid (SCFA)-producing bacteria inside gut are mostly beneficial bacteria. These bacteria either directly or, by increasing short-chain fatty acid inside gut, thus indirectly, perform functions including without limitation anti-inflammation, protecting intestinal barrier function, and regulating metabolism and immune system. These functions lead to the prevention or treatment of obesity, insulin resistance, diabetes, and other metabolic diseases.

Using the disclosed methods for improving gut microbiota population, the increased gut microbiota populationmay include *Alistipes, Allobaculum, Bacteroides, Barnesiella, Blautia, Butyricicoccus, Butyricimonas, Dorea, Helicobacter, Hespellia, Holdemania, Lawsonia, Oscillibacter, Parabacteroides, Phascolarctobacterium, Prevotella*, or *Sedimentibacter*. In one embodiment, the increased gut microbiota population may include *Bacteroidaceae, Coriobacteriaceae, Desulfovibrionaceae, Erysipelotrichaceae, Flavobacteriaceae, Helicobacteracea, IncertaeSedis XI, IncertaeSedis XIV, Lachnospiraceae, Porphyromonadaceae, Prevotellaceae, Rikenellaceae, Ruminococcaceae*, or *Veillonellaceae*; alternatively, the increased gut bacteria may include *Campylobacterales, Desulfovibrionales, Bacteroidales, Coriobacteriales, Flavobacteriales, Clostridiales*, or *Erysipelotrichales*; alternatively, the increased gut bacteria may include *Epsilonproteobacteria, Deltaproteobacteria, Bacteroidia, Coriobacteridae, Flavobacteria, Clostridia*, or *Erysipelotrichi*; alternatively, the increased gut bacteria may include *Proteobacteria, Bacteroidetes, Actinobacteria*, or *Firmicutes*.

For example, the increased gut microbiota population may include a bacterium whose V3 region of 16S rRNA gene sequence has at least about 70%, at least about 75%, at least about 80%, at least about 85%, at least about 90%, at least about 95%, at least about 98%, or at least about 99% similarity with a nucleic acid sequence selected from a group consisting of SEQ ID NO: 1-93.

The endotoxin-producing bacteria inside gut are mostly harmful bacteria, which, either directly or indirectly by increasing endotoxin, promote inflammation, damage intestinal barrier function, and increase disorder in metabolism and immune system, as a result inducing obesity, insulin resistance, diabetes and other metabolic diseases.

According to the methods for improving gut microbiota population disclosed herein, the decreased gut bacteria may include *Alistipes, Anaeroplasma, Barnesiella, Bifidobacterium, Butyricimonas, Butyrivibrio, Coprococcus, Fastidiosipila, Helicobacter, Hespellia, Marvinbryantia, Oribacterium, Oscillibacter, Prevotella, Roseburia, Ruminococcus*, or *TM7_genera_incertae_sedis*; alternatively, the decreased gut bacteria may include *Helicobacteraceae, Lachnospiraceae, Porphyromonadaceae, Prevotellaceae, Rikenellaceae, Ruminococcaceae, Anaeroplasmataceae*, or *Bifidobacteriaceae*. In one embodiment, the decreased gut microbiota population may include *Campylobacterales, Bacteroidales, Clostridiales, Anaeroplasmatales*, or *Bifidobacteriales*; alternatively, the decreased gut bacteria may include *Epsilonproteobacteria, Alphaaproteobacteria, Bacteroidia, Clostridia, Actinobacteridae*, or *Mollicutes*. In one embodiment, the decreased gut microbiota population may include *Proteobacteria, Bacteroidetes, Actinobacteria, Firmicutes*, or *Tenericutes*.

For example, the decreased gut bacteria may include a bacteria whose V3 region of 16S rRNA gene sequence has at least about 70%, at least about 75%, at least about 80%, at least about 85%, at least about 90%, at least about 95%, at least about 98%, or at least about 99% similarity with a nucleic acid sequence selected from a group consisting of SEQ ID NO: 94-268.

The methods may cause decrease of the serum level of pro-inflammatory factors. Example pro-inflammatory factors include without limitation cytokines such as lipopolysaccharide-binding protein, monocyte chemoattractant protein-1, or leptin. Additionally and optionally, the methods may increase the serum level of cytokine such as adiponectin.

The level of gut short-chain fatty acids may be increased using the disclosed methods. The short-chain fatty acids may include without limitation acetic acid, propionic acid, butyric acid, valeric acid, isobutyric acid, and isovaleric acid.

To improve the gut microbiota population, the compositions may be administered orally or parentally. In one embodiment, the composition may be a food, a drink, a supplement, or a pharmaceutical formulation. In one embodiment, the composition may be in the form of suppository, tablet, pill, granule, powder, film, microcapsule, aerosol, spirit, tincture, tonic, liquid suspension, or syrup. The composition may be administered at a dosage of from about 50 mg/kg body weight to about 400 mg/body weight.

In one example, the composition including berberine was administered to a subject. The gut microbiota population of the subject was then analyzed using 454 pyrosequencing techniques and the level of short-chain fatty acid was assayed by gas chromatography. The results demonstrated that berberine is capable of altering gut microbiota population: enriching certain bacteria including those that produce short-chain fatty acid while simultaneously suppressing or eliminating certain bacteria including those that produce endotoxin. It is further demonstrated that berberine administered orally is capable of increasing the level of shot-chain fatty acid inside the gut, and the increase is more pronounced in individuals who have metabolic syndrome. Additional experimentation and observation further demonstrated that above described effects by berberine on the gut microbiota population have beneficial results including without limitation improving insulin sensitivity, reducing inflammation, controlling weight gain, and preventing obesity induced by over-eating, chronic inflammation and insulin resistance.

In another aspect, the application provides methods for screening drugs, compounds, compositions, extracts, or formulations capable of improving gut microbiota population. The methods may be used in the development of drugs, nutritional supplements, health care products, food, and beverages that improve health and/or prevent obesity or other related metabolic syndromes by targeting gut microbiota population in a subject.

In one embodiment, the screening method may include administering to a control subject an effective amount of a control composition to increase the first gut microbiota population while simultaneously decrease the second gut microbiota population in the control subject, administering to a test subject an amount of a test composition, and comparing the gut microbiota population of the controlled subject and the gut microbiota population of the test subject.

As used herein, the term "subject" refers to an animal, such as a mammal, for example a human. In some embodiments, the subject may be a rat. In some embodiments, the subject may be a mouse. In some embodiments, the subject may be a human.

If the test compound demonstrates similar effect on gut microbiota as the control, the test compound is active in improving gut microbiota population. As used therein, "similar" refers to a similarity of at least about 75%, at least about 80%, at least about 90%, at least about 95%, at least about 98%, or at least about 99%.

The test composition may be a single compound, a mixture, a food, a food additive, a nutritional supplement, health care product, a pharmaceutical formulation, or a beverage.

In a further aspect, the application provides compositions for improving gut microbiota population. In one embodiment, the composition may be capable of selectively increasing the first gut microbiota population while simultaneously decreasing the second gut microbiota population in a subject.

The composition may include a chemical compound, a natural medicine, a natural product, or an herbal extract. In one embodiment, the chemical compound may include, without limitation, berberine, berberine derivatives, isoquinoline alkaloids, or any combinations thereof.

In one embodiment, the composition may include natural medicine, whole, fragmented or powdered herb, or herbal extract derived from plants of *Berberis, Coptis, Scutellaria, Phellodendron, Momordica, Ilex, Sophora, Gentiana, Anemarrhena, Gardenia, Rheum*, or *Taraxacum*. In one embodiment, the composition may include natural medicine, whole, fragmented or powdered herb, or herbal extract derived from plants of *Berberidaceae, Ranunculaceae, Lamiaceae, Rutaceae, Cucurbitacea, Aquifoliaceae, Leguminosae, Gentianaceae, Agavaceae, Rubiaceae, Polygonaceae, Asteraceae, Menispermaceae*, or *Cucurbitaceae*. In one embodiment, the composition may include natural medicine, whole, fragmented or powdered herb, or herbal extract derived from *Berberis vulgaris, Coptischinensis, Scutellariabaicalensis, PhellodendriChinensis, Momordicacharantia, Ilex kudingcha, Sophoraflavescens, Gentianascabra, Anemarrhenaasphodeloides, Gardenia jasminoides, Rheum palmatum*, or *Herba Taraxaci*.

The following examples are for illustration of the execution and property of representative method of the application. These examples are not intended to limit the scope of the application.

EXAMPLES

These examples use Wistar rats (8 weeks old, male) as testing subjects and berberine as a representative compound. 40 Wistar rats were acclimatized for two weeks and were subsequently randomly divided into four groups: normal diet group (NCD), normal diet plus berberine treatment (NCD+BBR), high fat diet (HFD), and high fat diet plus berberine treatment (HFD+BBR). Each group continued for another 18 weeks. During these 18 weeks, the NCD+BBR group received intragastric administration of berberine at stated levels. Feces samples from each animal were collected at various time points. 454 pyrosequencing was performed to analyze gut microbiota structure. Gas chromatography was used to assay the short-chain fatty acid level of the feces. In addition, weight, food intake, insulin sensitivity, systemic inflammation levels were monitored and measured during the 18-week period.

Berberine Altered the Gut Microbiota Population Under Both Normal Diet and High Fat Diet Conditions The gut microbiota populations in rats from all four experimental groups were analyzed by 454 pyrosequencing and multivariate statistical analyses. PCoA analysis based on unweighted Unifrac distance demonstrated that berberine altered gut microbiota structure in both the normal diet group and high fat diet group at a statistically significant level; and berberine accounts for 12.6% of overall changes in the gut microbiota population (FIG. 1A). Diet also exerted statistically significant influence on gut microbiota population. FIG. 1A reveals a statistically significant difference (3.7%) in gut microbiota population between two different diets (NCD versus HFD) along the vertical axis. The multivariate variance analysis (MANOVA) on the four groups demonstrated that berberine or diet has a statistically significant influence on the gut microbiota ($P<0.01$), but the most pronounced difference derives from the presence of berberine (FIG. 1B). Shannon-Wiener parameter indicates that berberine reduces diversity of gut microbiota population at a statistically significant level ($P<0.05$).

Figure 2:
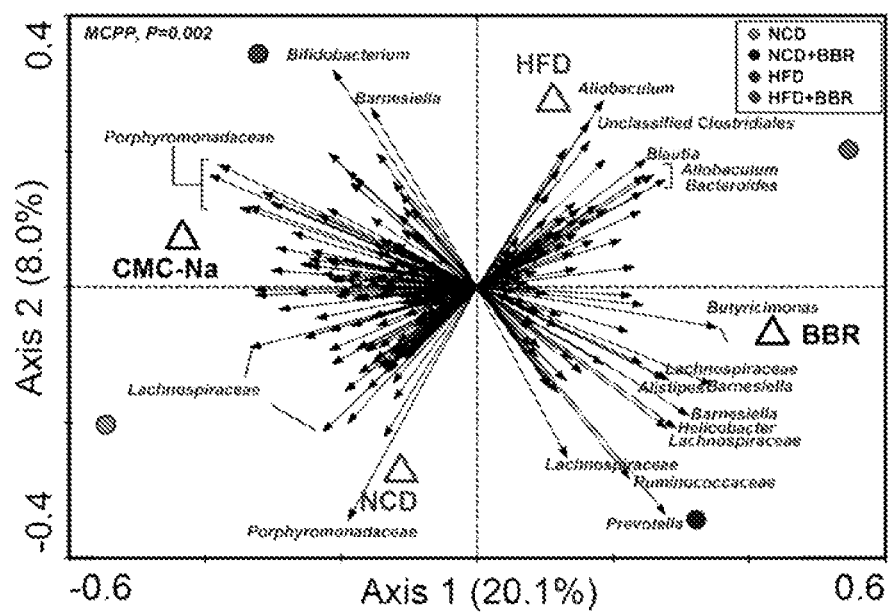
FIG. 2 illustrates some representative differences in the gut microbiota structure caused by berberine treatment using distance triplot of the RDA of gut microbiota.

Berberine Enriches the Short-Chain Fatty Acid-Producing Bacteria and Reduces Endotoxin-Producing Bacteria in Gut Microbiota Population 268 berberine-related OTU were identified by redundancy analysis (RDA) and the detailed results are shown in FIG. 2, TABLE 1, and TABLE 2. 93 OTU (SEQ_ID_NO 1-93) (TABLE 1) are enriched by berberine, while 175 OTU (SEQ_ID_NO 94-268) (TABLE 2) were suppressed or eliminated.

The taxonomy of these 268 OTU was analyzed using RDP classifier with representative sequence of the OTU. It was revealed that the berberine-suppressed bacteria included those of *Alistipes, Anaeroplasma, Barnesiella, Bifidobacterium, Butyricimonas, Butyrivibrio, Coprococcus, Fastidiosipila, Helicobacter, Hespellia, Marvinbryantia, Oribacterium, Oscillibacter, Prevotella, Roseburia, Ruminococcus, TM7_genera_incertae_sedis*, and others. Among them, the *Helicobacter*, belonging to *Proteobacteria phylum*, is capable of producing highly active endotoxin. In addition, it was revealed that the berberine-increased bacteria included those of *Alistipes, Allobaculum, Bacteroides, Barnesiella, Blautia, Butyricicoccus, Butyricimonas, Dorea, Helicobacter, Hespellia, Holdemania, Lawsonia, Oscillibacter, Parabacteroides, Phascolarctobacterium, Prevotella*, and *Sedimentibacter*. Among them, *Blautia, Allobaculum, Prevotella, Bacteroides*, and *Butyricimonas* are relatively abundant and are capable of producing short-chain fatty acid.

Therefore, when administered to a subject, berberine is capable of enriching the short-chain fatty acid-producing bacteria and reducing endotoxin-producing bacteria in gut microbiota population.

Figure 3:
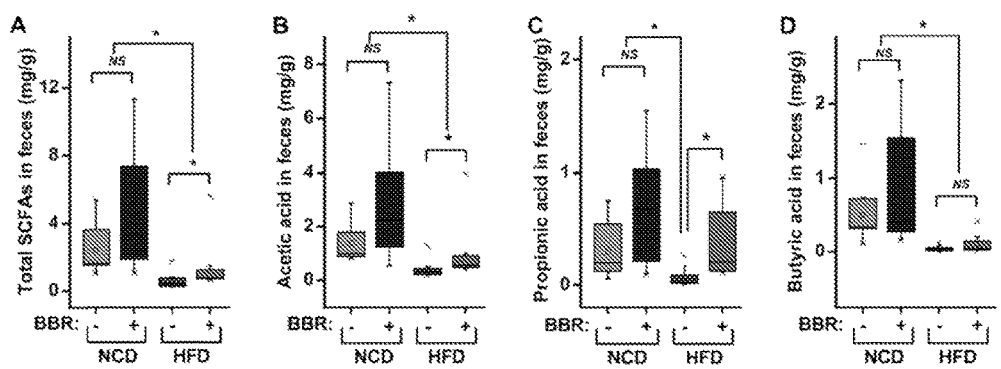
FIG. 3 illustrates the effect on the short-chain fatty acid contents in rat feces when the rats were fed with high fat diet or normal chow diet.

Berberine Increases Gut Short-Chain Fatty Acid Level in Rats Fed Normal Diet or High Fat Diet The levels of short-chain fatty acid (including acetic acid, propionic acid, butyric acid, valeric acid, isobutyric acid, isovaleric acid, etc.) in rat feces were assayed by gas chromatography. The result demonstrated that oral administration of 100 mg/kg body weight may increase the level of gut short-chain fatty acid in rats fed with normal diet or high fat diet. The effect on the levels of acetic acid and propionic acid are especially pronounced (FIG. 3). Therefore, berberine is capable of increasing gut short-chain fatty acid level in rats fed normal diet or high fat diet.

Berberine Reduces Obesity Phenotype of Rats

Figure 4:
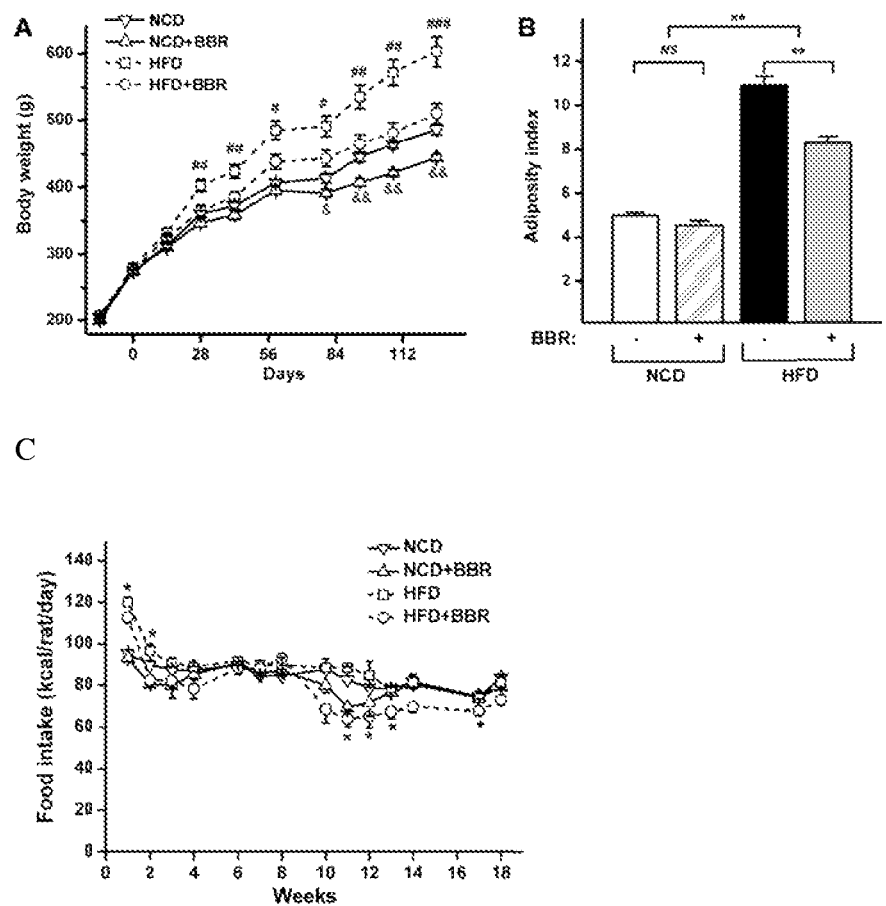
FIG. 4 illustrates the effect of berberine on obesity phenotypes and food intake in rats.

The body weight of all four groups of rats were monitored during the duration of the experiments and analyzed. The results demonstrated that, after 18 weeks of high fat diet, the HFD group has significantly higher body weight than the normal diet group ($P<0.01$); intragastric administration of berberine at the dosage of 100 mg/kg effectively limits rat body weight growth, especially for rats fed high fat diet. The result is especially surprising that during the entire experimental process, the body weight of the HFD+BBR group is limited to a level similar to that of normal diet group, displaying no statistically significant difference ($P>0.05$). Berberine also influences, to a certain degree, the body weight of rats fed a normal diet (FIG. 4).

At the end of experiment, animals were euthanized. Fasting body weight, epididymal fat weight, and perirenal fat weight were measured. Adiposity index ([epididymal fat weight+perirenal fat]/fasting weight×100) is shown in FIG. 4B. After 18 weeks of high fat diet, the adiposity index of the HFD group is significantly higher than that of NCD, and berberine treatment significantly reduces adiposity index. Moreover, neither high fat diet nor berberine had significant effect on liver and pancreas, indicating surprisingly that long term use of berberine has no obvious side effect to rat's normal physiological function. Results of the calorie intake of these rats demonstrated that oral administration of berberine at 100 mg/kg body weight has a significant inhibitory effect on rat food intake, especially on rats fed a high fat diet (FIG. 4C).

Figure 5:
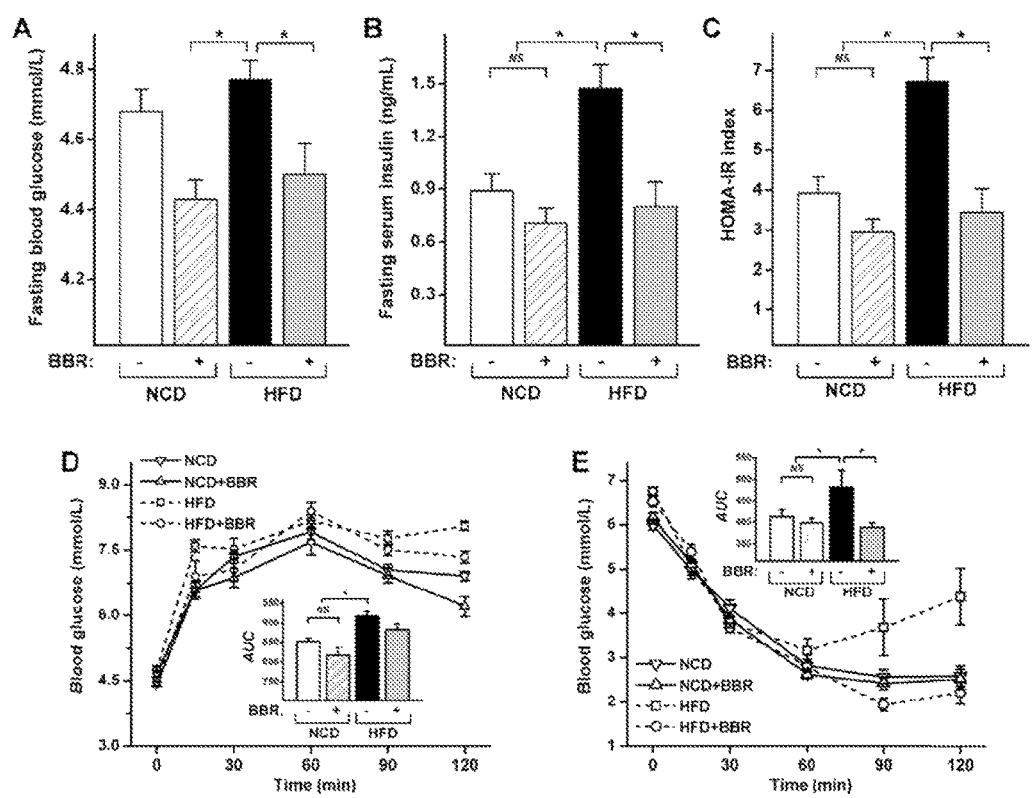
FIG. 5 illustrates the effect of berberine on the insulin sensitivity in rats.

Berberine Reduces Insulin sensitivity in Rats Fed a Normal Diet or High Fat Diet The fasting blood glucose (FBG) and fasting insulin in serum (FINS) were measured for all four experimental groups of rats. Rats fed a HFD for 18 months had a significant higher level of FBG than that of NCD. Surprisingly, berberine effectively reduced FBG in NCD and HFD rats, especially in HFD rats where the FBG reduction was significant ($P<0.05$) (FIG. 5A). The result of berberine effect on insulin level is shown in FIG. 5B. The FINS of rat fed a HFD was significantly higher than that of NCD group; however, after 18 month of berberine intervention at the level of 100 mg/kg body weight, FINS level was significantly reduced even in rats fed a HFD (HFD+BBR), to reach a level comparable to that of normal diet. FIG. 5C shows the result of HOMA insulin resistance index to evaluate the insulin resistance status in rats, which demonstrates that after 18 weeks of HFD induction, rats formed apparent insulin resistance; yet berberine intervention at 100 mg/kg body weight prevented the formation of insulin resistance ($P<0.05$).

In order to further examine insulin sensitivity, oral glucose tolerance test and intraperitoneal injection of insulin tolerance test were conducted, and the results are shown in FIG. 5D, and 5E, respectively. Consistent with the FBG and FINS result, after 18 weeks of high fat diet inducement, oral glucose tolerance and intraperitoneal injection of insulin tolerance were significantly damaged, meanwhile, berberine intervention at 100 mg/kg body weight significantly prevented the loss of glucose tolerance and insulin tolerance, demonstrating the berberine may play an important role in improving glucosemetabolism.

Berberine Reduces Systemic inflammation Level in Rats Fed a High Fat Diet

Figure 6:
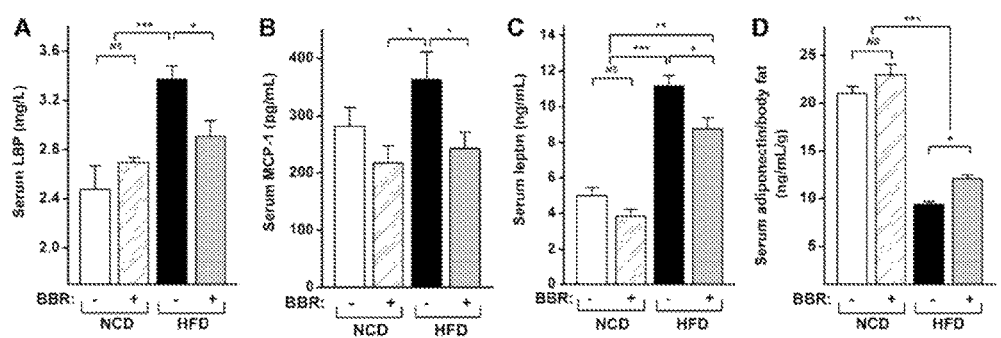
FIG. 6 illustrates the effect of berberine on the level of inflammation factors in rats.

In order to evaluate the systemic inflammation levels of all four experimental groups of rats, the serum levels of lipopolysaccharide (LPS)-binding protein (LBP), monocyte chemoattractant protein-1 (MCP-1), leptin, and adiponectin were measured, and results are shown in FIG. 6. The experiments demonstrates that HFD significantly increased LBP level in serum; but administering berberine at 100 mg/kg significantly abrogated the increase of serum LBP ($P<0.05$, FIG. 6A).

MCP-1 is a pro-inflammatory cytokine that functions in chemotaxis and activation of monocytes/macrophages. Occurrence and development of many inflammation-related diseases are closely related to MCP-1, including atherosclerosis, obesity, type 2 diabetes, arthritis, sepsis, and chronic bacterial infection. The results from the experiment demonstrated that, in the process of the gradual onset of obesity and insulin resistance in rat induced by HFD, MCP-1 level is gradually elevated; however, after intervention with berberine administering, MCP-1 level was significantly reduced, and, surprisingly, was even lower than that of NCD group (FIG. 6B).

Leptin is a hormone secreted by adipose tissue, and broadly participates in lipid, glucose, and energy metabolism. The results from the experiment demonstrated that serum leptin level in HFD group is significantly higher than that of NCD group ($P<0.01$); however, berberine significantly reduced the serum leptin level in rat, especially in rats fed a HFD ($P<0.05$, FIG. 6C).

The adiponectin levels in all four groups were analyzed. The results show that the adiponectin level normalized against body fat weight, was significantly lower in HFD group when compared to that of NCD group ($P<0.001$); however, berberine administration significantly increased adiponectin level in rats fed a HFD ($P<0.01$, FIG. 6D). Therefore, berberine improves gut microbiota population, reduces LPB, MCP-1, and lpetin level, and increases adiponectin secretion. TABLE 1 16S rRNA gene V3 region sequence of those bacteria enriched by berberine.

| List | OTUName | 16S rRNA Gene V3 Region Sequence |
|---|---|---|
| SEQ_ID_NO_1 | R_U00449939 | TAGGGAATATTGCTCAATGGGGAAACCCTGAAGCAGCAACGCCGCGTGGAGGATGAAGGTTTTCGGATTGTAAACTCCTTTTCTAAGAGAAGATTATGACGGTATCTTAGGAATAAGCACCGGCTAACTCCGTGCC |
| SEQ_ID_NO_2 | R_U01131573 | GGGGAAACCCTGAAGCAGCAACGCCGCGTGGAGGATGAAGGTTTCGGATTGTAAACTCCTTTCTAAGAGAAGATTATGACGGTATCTTAGGAATAAGCACCGGCTAACTCCGTGCC |
| SEQ_ID_NO_3 | R_U00442991 | TGGGGAATATTGCGCAATGGGCGAAAGCCTGACGCAGCGACGCCGCGTGAGGGATGAAGGTCCTCGGATCGTAAACCTCTGTCAGGGGGGAAGAAGCGCCTGTGAGCAAATAGTTCATGGGTTTGACGGTACCCCCAAAGGAAGCACCGGCTAACTCCGTGCC |
| SEQ_ID_NO_4 | R_U01131468 | TGAGGAATATTGGTCAATGGGCGCAGGCCTGAACCAGCCAAGTAGCGTGAAGGATGACTGCCCTATGGGTTGTAAACTTCTTTTATATGGGAATAAAGTTTTCCACGTGTGGAATTTTGTATGTGCCATATGAATAAGGATCGGCTAACTCCGTGCC |
| SEQ_ID_NO_5 | R_U00000076 | TGAGGAATATTGGTCAATGGACGAGAGTCTGAACCAGCCAAGTAGCGTGAAGGATGACTGCCCTATGGGTTGTAAACTTCTTTTATATGGGAATAAAGTGAGCCACGTGTGGCTTTTTGTATGTACCATACGAATAAGGATCGGCTAACTCCGTGCC |
| SEQ_ID_NO_6 | R_U00000261 | TGAGGAATATTGGTCAATGGGCGCAGGCCTGAACCAGCCAAGTAGCGTGAAGGATGACTGCCCTATGGGTTGTAAACTTCTTTTATATGGGAATAAAGTTTTCCACGTGTGGAATTTTGTATGTACCATATGAATAAGGATCGGCTAACTCCGTGCC |
| SEQ_ID_NO_7 | R_U00277049 | TGAGGAATATTGGTCAATGGGCGCAGGCCTGAACCAGCCAAGTAGCGTGAAGGATGACTGCCCTATGGGTTGTAAACTTCTTTTATATGGGAATAAAGTTTTCCTACGTGTGGAATTTTGTTATGTACCATATGAATAAGGATCGGCTAACTCCGTGCC |
| SEQ_ID_NO_8 | R_U01140154 | TGAGGAATATTGGTCAATGGGCGCGAGCCTGAACCAGCCAAGTAGCGTGCAGGACGACGGCCCTATGGGTTGTAAACTGTCTTTTATACGGGGATAAAGTATGCCACGTGTGGTTTATTGCAGGTACCGTATGAATAAGGACCGGCTAATTCCGTGCC |

| List | OTUName | 16S rRNA Gene V3 Region Sequence |
|---|---|---|
| SEQ_ID_NO_9 | R_U00797917 | TGAGGAATATTGGTCAATGGGCGCGAGCCTGAACCA GCCAAGTAGCGTGCAGGACGACGGCCCTATGGGTTG TAAACTGCTTTTATACGGGGATAAAGTATGCCACGTG TGGTTTATTGCAGGTACCGTATGAATAAGGACCGGCT AATTCCGTGCC |
| SEQ_ID_NO_10 | R_U01135802 | TGAGGAATATTGGTCAATGGGCGGAAGCCTGAACCA GCCAAGTCGCGTGAGGGAAGACGGCCCTACGGGTTG TAAACCTCTTTTGCCGGGGAGGCAATGCCCACGCTCG CGAGCTGGGAAGGAGAGTACCCGGAGAAAAAGACAT CGGCTAACTCCGTGCC |
| SEQ_ID_NO_11 | R_U01199632 | TGAGGAATATTGGTCAATGGGCGGAAGCCTGAACCA GCCAAGTCGCGTGAGGGAAGACGGCCCTACGGGTTG TAAACCTCTTTTGCCGGGGAGCAATGCCCACGCTCGC GAGCTGGGAAGGAGAGTACCCGGAGAAAAAGACATC GGCTAACTCCGTGCC |
| SEQ_ID_NO_12 | R_U01136954 | TGAGGAATATTGGTCAATGGGCGGAAGCCTGAACCA GCCAAGTCGCGTGAGGGAAGACGGCCCTACGGGTTG TAAACCTCTTTTGCCGGGGAGCAAATGCCCAGCTCGC GAGCTGGGAAGGAGAGTACCCGGAGAAAAAGCATCG GCTAAACTCCGTGCC |
| SEQ_ID_NO_13 | R_U01156163 | TGAGGAATATTGGTCAATGGGCGAGAGCCTGAACCA GCCAAGTCGCGTGAGGGAAGACGGCCCTACGGGTTG TAAACCTCTTTTGTCAGGGAGCAAGAACAGGCACGT GTGCCTGACTGAGAGTACCTGAAGAAAAAGACATCG GCTAACTCCGTGCC |
| SEQ_ID_NO_14 | R_U00436427 | TGAGGAATATTGGTCAATGGCCGGAAGGCTGAACCA GCCAAGTCGCGTGAGGGACTAAGGCCCTACGGGTTG TAAACCTCTTTTGCCGGGGAGCAATGGGGCCCTTGCG AGGGCCCAGGGAGAGTACCCGGAGAAAAAGCATCGG CTAACTCCGTGCC |
| SEQ_ID_NO_15 | R_U01161731 | TGAGGAATATTGGTCAATGGCCGGGAGGCTGAACCA GCCAAGTCGCGTGAGGGATGACGGCCCTACGGGTTG TAAACCTCTTTTGTCGGGGAGCAAAGGACTTCACGAG TGGAGTTTCGAGAGTACCCGAAGAAAAAGACATCGG CTAACTCCGTGCC |
| SEQ_ID_NO_16 | R_U00804243 | TGAGGAATATTGGTCAATGGCCGGGAGGCTGAACCA GCCAAGTCGCGTGAGGGATGACGGCCCTACGGGTTG TAAACCTCTTTTGTCGGGGAGCAAAGGACTTCACGAG TGGAGTTTCGAGAGTACCCGAAGAAAAAGCATCGGC TAACTCCGTGCC |
| SEQ_ID_NO_17 | R_U00832647 | TGAGGAATATTGGTCAATGGCCGGGAGGCTGAACCA GCCAAGTCGCGTGAGGGATGACGGCCCTACGGGTTG TAAACCTCTTTGTCGGGGAGCAAAGGACTTCACGAGT GGAGTTTCGAGAGTACCCGAAGAAAGACATCGGCTA ACTCCGTGCC |
| SEQ_ID_NO_18 | R_U00013412 | TGAGGAATATTGGTCAATGGGCGAGAGCCTGAACCA GCCAAGTCGCGTGAGGGAAGACGGCCCTACGGGTTG TAAACCTCTTTTGTCAGGGAGCAAGAACAGGCACGT GTGCCTGACTGAGAGTACCTGAAGAAAAAGCATCGG CTAACTCCGTGCC |
| SEQ_ID_NO_19 | R_U00807079 | TGAGGAATATTGGTCAATGGCCGAGAGGCTGAACCA GCCAAGTCGCGTGAGGGATGACGGCCCTACGGGTTG TAAACCTCTTTTGTCGGGGAGCAAAGGACTTCACGTG TGAAGTTTCGAGAGTACCCGAAGAAAAAGCATCGGC TAACTCCGTGCC |
| SEQ_ID_NO_20 | R_U00005346 | TGAGGAATATTGGTCAATGGGCGGAAGCCTGAACCA GCCAAGTCGCGTGAGGGAAGACGGTCCTATGGATTG TAAACCTCTTTTGCCGGGGAGCAATGCCGCTCTTGCG AGAGCGGAGGGAGAGTACCCGGAGAAAAAGCATCG GCTAACTCCGTGCC |
| SEQ_ID_NO_21 | R_U00004086 | TGAGGAATATTGGTCAATGGCCGGAAGGCTGAACCA GCCAAGTCGCGTGAGGGAATAAGGCCCTACGGGTCG TAAACCTCTTTTGTCAGGGAGCAAAGCTGGTACGCG TAGCCAGAAGGAGAGTACCTGAAGAAAAAGCATCGG CTAACTCCGTGCC |

-continued

| List | OTUName | 16S rRNA Gene V3 Region Sequence |
|---|---|---|
| SEQ_ID_NO_ 22 | R_U01130438 | TGAGGAATATTGGTCAATGGGCGGAAGCCTGAACCA GCCAAGTCGCGTGAGGGAAGACGGCCCTACGGGTTG TAAACCTCTTTGCCGGGGAGCAATGCCCAGCTCGCGAG CTGGGAAGGAGAGTACCCGGAGAAAAGACATCGGCT AACTCCGTGCC |
| SEQ_ID_NO_ 23 | R_U01131459 | TGAGGAATATTGGTCAATGGGCGGAAGCCTGAACCA GCCAAGTCGCGTGAGGGAAGACGGCCCTACGGGTTG TAAACCTCTTTGCCGGGGAGCAATGCCCAGCTCGCGA GCTGGGAAGGAGAGTACCCGGAGAAAAGACATCGGC TAACTCCGTGCC |
| SEQ_ID_NO_ 24 | R_U00436448 | TGAGGAATATTGGTCAATGGGCGGAAGCCTGAACCA GCCAAGTCGCGTGAGGGACTAAGGCCCTACGGGTCG TAAACCTCTTTTGCCGGGGAGCAAGCCGTCCCACGTG TGGGCCGGTGGAGAGTACCCGGAGAAAAAGCATCGG CTAACTCCGTGCC |
| SEQ_ID_NO_ 25 | R_U00474862 | TGAGGAATATTGGTCAATGGGCGGAAGCCTGAACCA GCCAAGTCGCGTGAGGGACTAAGGCCCTACGGGTCG TAAACCTCTTTTGCCGGGGAGCAAGCCGTCCCACGTG TGGGCCGGTGGAGAGTACCCGGAGAAAAAGACATCG GCTAACTCCGTGCC |
| SEQ_ID_NO_ 26 | R_U00001388 | TGAGGAATATTGGTCAATGGGCGGAAGCCTGAACCA GCCAAGTCGCGTGAGGGAAGACGGCCCTACGGGTTG TAAACCTCTTTTGCCGGGGAGCAATGCCCAGCTCGCG AGCTGGGAAGGAGAGTACCCGGAGAAAAAGCATCGG CTAACTCCGTGCC |
| SEQ_ID_NO_ 27 | R_U01185184 | TGAGGAATATTGGTCAATGGGCGGAAGCCTGAACCA GCCAAGTCGCGTGAGGGAAGACGGCCCTACGGGTTG TAAACCTCTTTTTGCCGGGGGAGCAATGCCCAGCTCG CGAGCTGGGAAGGAGAGTACCCGGAGAAAAAAGCAT CGGCTAACTCCGTGCC |
| SEQ_ID_NO_ 28 | R_U00000528 | TGAGGAATATTGGTCAATGGGCGAGAGCCTGAACCA GCCAAGTCGCGTGAAGGATGAAGGATCTATGGTTTGT AAACTTCTTTTATATGGGAATAAAGTGAGGAACGTGT TCCTTTTTGTATGTACCATATGAATAAGCATCGGCTA ACTCCGTGCC |
| SEQ_ID_NO_ 29 | R_U00000002 | TGAGGAATATTGGTCAATGGACGAGAGTCTGAACCA GCCAAGTAGCGTGAAGGATGACTGCCCTATGGGTTGT AAACTTCTTTTATACGGGAATAAAGTGAGGCACGTGT GCCTTTTTGTATGTACCGTATGAATAAGGATCGGCTA ACTCCGTGCC |
| SEQ_ID_NO_ 30 | R_U00147566 | TGAGGAATATTGGTCAATGGACGCAAGTCTGAACCA GCCATGCCGCGTGCAGGAAGACGGCTCTATGAGTTGT AAACTGTCTTTTGTACTAGGGTAAACGCTCTTACGTG TAGGAGCCTGAAAGTATAGTACGAATAAGGATCGGC TAACTCCGTGCC |
| SEQ_ID_NO_ 31 | R_U00000394 | TGAGGAATATTGGTCAATGGACGCAAGTCTGAACCA GCCATGCCGCGTGCAGGAAGACGGCTCTATGAGTTGT AAACTGCTTTTGTACTAGGGTAAACGCTTCTACGTGT AGGAGCCTGAAAGTATAGTACGAATAAGGATCGGCT AACTCCGTGCC |
| SEQ_ID_NO_ 32 | R_U00047397 | TGGGGAATTTTGCGCAATGGGGGAACCCTGACGCA GCAACGCCGCGTGCGGGATGACGGCCCTCGGGTTGT AAACCGCTTTCAGCAGGGAAGACCACGACGGTACCT GCAGAAGAAGCTCCGGCTAACTACGTGCC |
| SEQ_ID_NO_ 33 | R_U00000552 | TGAGGAATATTGGGCAATGGGCGGAAGCCTGACCCA GCCATGCCGCGTGCAGGAAGACAGCCCTATGGGTCG TAAACTGCTTTTTTAGAGGAAGAATAAAGTSTACGTG TAGACCGATGACGGTACTTTAAGAAAAAGCATCGGC TAACTCCGTGCC |
| SEQ_ID-NO_ 34 | R_U00441706 | GTAGGGAATATTGCACAATGGGGGAAACCCTGATGC AGCGACGCCGCGTGAAGGAAGAAGTATCTCGGTATG TAAACTTCTATCAGCAGGGAAGACAATGACGGTACC TGACTAAGAAGCCCCGGCTAACTACGTGCC |

-continued

| List | OTUName | 16S rRNA Gene V3 Region Sequence |
|---|---|---|
| SEQ_ID_NO_35 | R_U00119974 | TGGGGAATATTGCACAATGGGGGAAACCCTGATGCA<br>GCGACGCCGCGTGAAGGAAGAAGTATTTCGGTATGT<br>AAACTTCTATCAGCAGGGAAGAAAGTGACAGTACCT<br>GACTAAGAAGCCCCGGCTAACTACGTGCC |
| SEQ_ID_NO_36 | R_U00104206 | TGGGGAATATTGCACAATGGGGGAAACCCGTACGAT<br>GCAGCGACGCCGCGTGAAGGAAGAAGTATCTCGGTA<br>TGTAAACTTCTATCAGCAGGGAAGATAATGACGGTA<br>CCTGACTAAGAAGCCCCGGCTAACTACGTGCC |
| SEQ_ID_NO_37 | R_U00580795 | TGGGGAATATTGCACAATGGGGGAAACCCGTACGAT<br>GCAGCGACGCCGCGTGAAGGAAGAAGTATCTCGGTA<br>TGTAAACTTACTATCAGCAGGGAAGATAATGACGGT<br>ACCTGACTAAGAAGCCCCGGCCTAACTACGTGCC |
| SEQ_ID_NO_38 | R_U01129900 | AAACCCTGATGCAGCGACGCCGCGTGAAGGAAGAAG<br>TATCTCGGTATGTAAACTTCTATCAGCAGGGAAGACA<br>ATGACGGTACCTGACTAAGAACGCCCGGCTAACTAC<br>GTGCC |
| SEQ_ID_NO_39 | R_U00016467 | TGGGGAATATTGCACAATGGGGGAAACCCTGATGCA<br>GCGACGCCGCGTGAAGGAAGAAGTATCTCGGTATGT<br>AAACTTCTATCAGCAGGGAAGATAATGACGGTACCT<br>GACTAAGAAGCCCCGGCTAATTACGTGCC |
| SEQ_ID_NO_40 | R_U00000367 | TGGGGAATATTGCACAATGGGGGAAACCCTGATGCA<br>GCGACGCCGCGTGAAGGAAGAAGTATCTCGGTATGT<br>AAACTTCTATCAGCAGGGAAGATAATGACGGTACCT<br>GACTAAGAAGCCCCGGCTAACTACGTGCC |
| SEQ_ID_NO_41 | R_U00459481 | TGGGGAATATTGCACAATGGGGGAAACCCTGATGCA<br>GCAACGCCGCGTGGGTGAAGGAGCGTTTCGGCGCGT<br>AAAGCCCTGTCAGCGGGGAAGAAAAAAGACGGTACC<br>CGACCAAGAAGCCCCGGCTAACTACGTGCC |
| SEQ_ID_NO_42 | R_U00000215 | TGGGGAATATTGCACAATGGGCGCAAGCCTGATGCA<br>GCGACGCCGCGTGAGTGAAGAAGTATTTCGGTATGT<br>AAAGCTCTATCAGCAGGGAAGAAAATGACGGTACCT<br>GACTAAGAAGCCCCGGCTAACTACGTGCC |
| SEQ_ID_NO_43 | R_U00071963 | TGGGGAATATTGCACAATGGGGGAAACCCTGATGCA<br>GCGACGCCGCGTGAAAGATGAAGTATTTCGGTATGT<br>AAACTTCTATCAGCAGGGAAGAAAATGACGGTACCT<br>GACTAAGAAGCCCCGGCTAACTACGTGCC |
| SEQ_ID_NO_44 | R_U00000939 | TGGGGAATATTGCACAATGGAGGAAACTCTGATGCA<br>GCGACGCCGCGTGAGTGAAGAAGTATTTCGGTATGT<br>AAAGCTCTATCAGCAGGGAAGACAGTGACGGTACCT<br>GACTAAGAAGCTCCGGCTAAATACGTGCC |
| SEQ_ID_NO_45 | R_U00472681 | TGGGGAATATTGCACAATGGGGGGAACCCTGATGCA<br>GCGACGCCGCGTGAGTGACGAAGTATCTCGGTATGT<br>AAAGCTCTGTCAGCAGGGAAGAAGAATGACGGTACC<br>TGAAGAAGAAGCACCGGCTAAATACGTGCC |
| SEQ_ID_NO_46 | R_U00000105 | TGGGGAATATTGCACAATGGGCGAAAGCCTGATGCA<br>GCGACGCCGCGTGAGTGAAGAAGTATTTCGGTATGT<br>AAAGCTCTATCAGCAGGGAAGAAAATGACGGTACCT<br>GACTAAGAAGCCCCGGCTAACTACGTGCC |
| SEQ_ID_NO_47 | R_U00000279 | TGGGGAATATTGCACAATGGGCGAAAGCCTGATGCA<br>GCAACGCCGCGTGAAGGAAGACGGTTTTCGGATTGT<br>AAACTTCTATCAATAGGGAAGAAAGAAATGACGGTA<br>CCTAAATAAGAAGCCCCGGCTAACTACGTGCC |
| SEQ_ID_NO_48 | R_U00022935 | TGGGGAATATTGCACAATGGGGGAAACCCTGATGCA<br>GCAACGCCGCGTGAAGGAAGACGGTTTTCGGATTGT<br>AAACTTCTATCAATAGGGAAGAAAGAAATGACGGTA<br>CCTAAATAAGAAGCCCCGGCTAACTACGTGCC |
| SEQ_ID_NO_49 | R_U00000550 | TGGGGAATATTGCACAATGGGGGAAACCCTGATGCA<br>GCGACGCCGTGGAGGAAGAAGGTCTTCGGATTGT<br>AAACTCCTGTCCCAGGGGACGATAATGACGGTACCCT<br>GGGAGGAAGCACCGGCTAACTACGTGCC |

| List | OTUName | 16S rRNA Gene V3 Region Sequence |
|---|---|---|
| SEQ_ID_NO_50 | R_U00009280 | TGGGGAATATTGCACAATGGGCGCAAGCCTGATGCAGCAACGCCGCGTGAAGGAAGACGGTTTTCGGATTGTAAACTTCTGTTCTTAGTGAAGAAGAATGACGGTAGCTAAGGAGCAAGCCACGGCTAACTACGTGCC |
| SEQ_ID_NO_51 | R_U00164237 | TGGGGAATATTGCACAATGGGCGCAAGCCTGATGCAGCAACGCCGCGTGAAGGAAGACGGTTTTCGGATTGTAAACTTCTGTTCTTAGTGAAGAATAATGACGGTAACTAAGGAGCAAGCCACGGCTAACTACGTGCC |
| SEQ_ID_NO_52 | R_U00032911 | TGGGGAATATTGCACAATGGGGGAAACCCTGATGCAGCGACGCCGAGTGAGGGAAGAAGGTTTTCGGATTGTAAACCTCTGTCCTTGGTGAAGATAATGACGGTAGCCAAGGAGGAAGCTACGGCTAACTACGTGCC |
| SEQ_ID_NO_53 | R_U00040533 | TGGGGAATATTGCACAATGGGGGAAACCCTGATGCAGCGACGCCGCGTGAGGGAAGACGGCCTTCGGGTTGTAAACCTCTGTCGCAGGGGACGAAGGAAGTGACGGTACCCTGTGAGGAAGCCACGGCTAACTACGTGCC |
| SEQ_ID_NO_54 | R_U01145869 | GAATATTGCGCAATGGGGGCAACCCTGACGCAGCAACGCCGCGTGAAGGATGAAGGTTTTCGGATTGTAAACTTCTTTTATCAAGGACGAAGGACGTGACGGTACTTGATGAATAAGCCACGGCTAACTACGTGCC |
| SEQ_ID_NO_55 | R_U00211687 | TGGGGAATATTGGGCAATGGGGGAAACCCTGACCCAGCAACGCCGCGTGAAGGAAGAAGGCTTTCGGGTTGTAAACTTCTTTTACCAGGGGACGAAGGACGTGACGGTACCTGGAGAAAAAGCAACGGCTAACTACGTGCC |
| SEQ_ID_NO_56 | R_U01206474 | TGGGGAATATTGGGCAATGGGGGAAACCCTGACCCAGCAACGCCGCGTGAAGGAAGAAGGCTTTCGGGTTGTAAACTTCTTTTACCTAGGGACGAAGGACGTGACGGTACCTGGAGAAAAAGACAACGGCTAACTACGTGCC |
| SEQ_ID_NO_57 | R_U01219720 | TGGGGAATATTGGGCAATGGGGGAAACCCTGACCCAGCAACGCCGCGTGAAGGAAGAAGGTTTTCGGGTTGTAAACTTCTTTTACCAGGGACGAAGGACGTGACGGTACCTGGAGAAAAAGCAACGGCTAACTACGTGCC |
| SEQ_ID_NO_58 | R_U01210669 | GACCCAGCAACGCCGCGTGAAGGAAGAAGGTCGTTTCGGGTTAGTAAACTTCTTTTACCGAGGGACGAAGGACGTGACGGTACCTGGAGAAAAAGCAACGGCTAACTACGTGCC |
| SEQ_ID_NO_59 | R_U00001394 | TGGGGAATATTGGGCAATGGGGGAAACCCTGACCCAGCAACGCCGCGTGAAGGAAGAAGGCTTTCGGGTTGTAAACTTCTTTTACCAGGGACGAAGGACGTGACGGTACCTGGAGAAAAAGCAACGGCTAACTACGTGCC |
| SEQ_ID_NO_60 | R_U00460521 | TGGGGAATATTGGGCAATGGGGGAAACCCTGACCCAGCAACGCCGCGTGAAGGAAGAAGGCTTTCGGGTTGTAAACTTCTTTTACCTAGGGACGAAGGACGTGACGGTACCTGGAGAAAAAGACAACGGCTAACTACGTGCC |
| SEQ_ID_NO_61 | R_U00831992 | TGGGGAATATTGGGCAATGGGGGAAACCCTGACCCAGCAACGCCGCGTGAAGGAAGAAGGCTTTCGGGTTGTAAACTTCTTTTACCAGGGACGAAGGACGTGACGGTACCTGGAGAAAAAGACAACGGCTAACTACGTGCC |
| SEQ_ID_NO_62 | R_U01143501 | TGGGGAATATTGGGCAATGGGCGCAAGCCTGACCCAGCAACGCCGCGTGAAGGAAGAAGGCTTTCGGGTTGTAAACTTCTTTTCTGGGGACGAAGAAAGTGACGGTACCCCACGGAATAAGCCACGGCTAACTACGTGCC |
| SEQ_ID_NO_63 | R_U00815791 | TGGGGAATATTGGGCAATGGGCGCAAGCCTGACCCAGCAACGCCGCGTGAAGGAAGAAGGCTTTCGGGTTGTAAACTTCTTTTCTGGGGGCGAAGAAAGTGACGGTACCCCAGGAATAAGCCACGGCTAACTACGTGCC |
| SEQ_ID_NO_64 | R_U00043629 | TGGGGAATATTGGGCAATGGGCGCAAGCCTGACCCAGCAACGCCGCGTGAAGGAAGAAGGCTTTCGGGTTGTAAACTTCTTTTCTGGGGACGAAGAAAGTGACGGTACCCCAGGAATAAGCCACGGCTAACTACGTGCC |

| List | OTUName | 16S rRNA Gene V3 Region Sequence |
|---|---|---|
| SEQ_ID_NO_ 65 | R_U00164098 | TGGGGAATATTGGGCAATGGGCGCAAGCCTGACCCA GCAACGCCGCGTGAAGGAAGAAGGCTTTCGGGTTGT AAACTTCTTTTCTCGGGGACGAACAAATGACGGTACC CGAGGAATAAGCCACGGCTAACTACGTGCC |
| SEQ_ID_NO_ 66 | R_U00000374 | TGGGGAATATTGCGCAATGGGGGCAACCCTGACGCA GCAACGCCGCGTGATTGAAGAAGGTCTTCGGATTGTA AAAATCTTTTATCAAGGACGAAGAAGTGACGGTACTT GATGAATAAGCTCCGGCTAACTACGTGCC |
| SEQ_ID_NO_ 67 | R_U00003296 | TGGGGAATATTGGGCAATGGGGGGAACCCTGACCCA GCAACGCCGCGTGAGGGAAGAAGGTTTTCGGATCGT AAACCTCTGTCCTTGGTGAAGAGGAGAAGACGGTAG CCAAGGAGGAAGCCCCGGCTAACTACGTGCC |
| SEQ_ID_NO_ 68 | R_U00027329 | TGGGGAATATTGGGCAATGGGGGAAACCCTGACCCA GCAACGCCGCGTGAGGGAAGAAGGTTTTCGGATCGT AAACCTCTGTCCTTGGTGAAGAGAAGAAGACGGTAG CCAAGGAGGAAGCCCCGGCTAACTACGTGCC |
| SEQ_ID_NO_ 69 | R_U00003420 | TGGGGAATATTGCACAATGGGCGAAAGCCTGATGCA GCAACGCCGCGTGAAGGATGAAGTATTTCGGTATGT AAACTTCTATCAGCAGGGAAGATAACGACGGTACCT GACTAAGAAGCCCCGGCTAACTACGTGCC |
| SEQ_ID_NO_ 70 | R_U00436238 | TGGGGAATATTGCACAATGGGCGCAAGCCTGATGCA GCAACGCCGCGTGAACGAAGAAGGTCTTCGGATTGT AAAGTTCTGTCCTTAGGGAAGAAGAAAGTGACGGTA CCTAAGGAGGAAGCCCCGGCTAACTACGTGCC |
| SEQ_ID_NO_ 71 | R_U00439751 | TGGGGAATATTGCACAATGGGCGAAAGCCTGATGCA GCGACGCCGCGTGAGTGAAGAAGTATTTCGGTATGT AAAGCTCTATCAGCAGGGAAGAAAATGACGGTACCT G |
| SEQ_ID_NO_ 72 | R_U00004741 | TGGGGAATATTGCACAATGGGGGAAACCCTGATGCA GCGACGCCGCGTGAAGGAAGAAGTATTTCGGTATGT AAACTTCTATCAGCAGGGAAGAAAATGACGGTACCT GACTAAGAAGCCCCGGCTAATTACGTGCC |
| SEQ_ID_NO_ 73 | R_U01160251 | TAGGGAATTTTTCGTCAATGGGCGCAAGCCTGAACGA GCAATGCCGCGTGGGCGAAGAAGGTCTTCGGATCGT AAAACTCTGTTGCGGGGGAAAAAGGAAGGGAAGAG GAAATGCTTTTCTTTTGATGGTACCCCGCCAGAAAGT CACGGCTAACTACGTGCC |
| SEQ_ID_NO_ 74 | R_U01166410 | TAGGGAATTTTTCGTCAATGGGCGCAAGCCTGAACGA GCAATGCCGCGTGAGCGAAGAAGGTCTTCGGATCGT AAAACTCTGTTGCGGGGGAAAAAGGAAGGAAAGAG GAAATGCTTTTCTTTTGATGGTACCCCGCCAGAAAGT CACGGCTAACTACGTGCC |
| SEQ_ID_NO_ 75 | R_U01169117 | TAGGGAATTTTTCGTCAATGGGCGCAAGCCTGAACGA GCAATGCCGCGTGGGCGAAGAAGGTCTTCGGATCGT AAAAACTCTGTTGCGGGGGAAAAAAGGAAGGGAAG AGGAAATGCTTTTCTTTTGATGGTACCCCGCCAGAAA GTCACGGCTAACTACGTGCC |
| SEQ_ID_NO_ 76 | R_U01180557 | TAGGGAATTTTCGTCAATGGGCGCAAGCCTGAACGA GCAATGCCGCGTGGGCGAAGAAGGTCTTCGGATCGT AAAACTCTGTTTGCGGGGGAAAAAGGAAGGGAAGA GGAAATGCTTTTCTTTTGATGGTACCCCGCCAGAAAG TCACGGCTAACTACGTGCC |
| SEQ_ID_NO_ 77 | R_U00804007 | TAGGGAATTTTCGTCAATGGGCGCAAGCCTGAACGA GCAATGCCGCGTGGGCGAAGAAGGTCTTCGGATCGT AAAACTCTGTTGCGGGGGAAAAAGGAAGGGAAGAG GAAATGCTTTTCTTTTGATGGTACCCCGCCAGAAAGT CACGGCTAACTACGTGCC |
| SEQ_ID_NO_ 78 | R_U01143008 | TAGGGAATTTTCGTCAATGGGCGCAAGCCTGAACGA GCAATGCCGCGTGAGCGAAGAAGGTCTTCGGATCGT AAAACTCTGTTGCGGGGAAAAGGAAGGGAAGAGGA AATGCTTTTCTTTTGTATGGTACCCCGCCAGAAAGTC ACGGCTAACTACGTGCC |

-continued

| List | OTUName | 16S rRNA Gene V3 Region Sequence |
|---|---|---|
| SEQ_ID_NO_79 | R_U01145549 | TAGGGAATTTTCGTCAATGGGCGCAAGCCTGAACGA GCAATGCCGCGTGGGCGAAGAAGGTCTTCGGATCGT AAAACTCTGTTGCGGGGGAAAAGGAAGGGAAGAGG AAATGCTTTTCTTTTGTATGGTACCCCGCCAGAAAGT CACGGCTAACTACGTGCC |
| SEQ_ID_NO_80 | R_U00808391 | TAGGGAATTTTCGTCAATGGGCGCAAGCCTGAACGA GCAATGCCGCGTGGGCGAAGAAGGTCTTCGGATCGT AAAACTCTGTTGCGGGGGAAAAGGAAGGGAAGAGG AAATGCTTTTCTTTTGATGGTACCCCGCCAGAAAGTC ACGGCTAACTACGTGCC |
| SEQ_ID_NO_81 | R_U01144224 | GGTAATTTTCGTCAATGGGCGCAAGCCTGAACGAGC AATGCCGCGTGGGCGAAGAAGGTCTTCGGATACGTA AACTCTGTTGCGGGGGAAAAGGAAGGGAAGAGGA AATGCTTTCTTTTGATGGTACCCCGCCAGAAAGTCAC GGCTAACTACGTGCC |
| SEQ_ID_NO_82 | R_U01214804 | TAGGGAATTTTCGTCAATGGGCGCAAGCCTGAACGA GCAATGCCGCGTGAGCGAAGAAGGTCTTCGGATCGT AAAACTCTGTTGCGGGGGAAAAGGAAGGGAAGAG GAAATGCTTTTCTTTTGATGGTACCCCGCCCAGAAAG TCACGGCTAACTACGTGCC |
| SEQ_ID_NO_83 | R_U01173110 | TAGGGAATTTTCGTCAATGGGCGCAAGCCTGAACGA GCAATGCCGCGTGAGCGAAGAAGGTCTTCGGATCGT AAAACTCTGTTGCGGGGGAAAAAAGGAAGGGAAGA GGAAATGCTTTTCTTTTGATGGTACCCCGCCAGAAAG TCACGGCTAACTACGTGCC |
| SEQ_ID_NO_84 | R_U00305232 | TAGGGAATTTTCGTCAATGGGCGCAAGCCTGAACGA GCAATGCCGCGTGAGCGAAGAAGGTCTTCGGATCGT AAAACTCTGTTGCGGGGGAAAAGGAAGGGAAGAG GAAATGCTTTTCTTTTGATGGTACCCCGCCAGAAAGT CACGGCTAACTACGTGCC |
| SEQ_ID_NO_85 | R_U00043735 | TAGGGAATTTTTCGTCAATGGGCGCAAGCCTGAACGA GCAATGCCGCGTGAACGAGGAAGGTCTTCGGATCGT AAAGTTCTGTTGAGAGGGAAAAAGGGTCACCAGAGG AAATGCTGGTGAAGTGATATTACCTTTCGAGGAAGTC ACGGCTAACTACGTGCC |
| SEQ_ID_NO_86 | R_U00000409 | TAGGGAATTTTCGTCAATGGGCGCAAGCCTGAACGA GCAATGCCGCGTGAACGAGGAAGGTCTTCGGATCGT AAAGTTCTGTTGAGAGGGAAAAAGGGTCACCAGAGG AAATGCTGGTGAAGTGATATTACCTTTCGAGGAAGTC ACGGCTAACTACGTGCC |
| SEQ_ID_NO_87 | R_U00029718 | GGTAATTTTCGTCAATGGGCGCAAGCCTGAACGAGC AATGCCGCGTGAACGAGGAAGGTCTTCGGATCGTAA AGTTCTGTTGAGAGGGAAAAAGGGTCACCAGAGGAA ATGCTGGTGAAGTGATATTACCTTTCGAGGAAGTCAC GGCTAACTACGTGCC |
| SEQ_ID_NO_88 | R_U00007185 | TAGGGAATTTTCGTCAATGGGCGCAAGCCTGAACGA GCAATGCCGCGTGAACGAGGAAGGTCTTCGGATCGT AAAGTTCTGTTGAGAGGGAAAAAAGGGTCACCAGAG GAAATGCTGGTGAAGTGATATTACCTTTCGAGGAAGT CACGGCTAACTACGTGCC |
| SEQ_ID_NO_89 | R_U00011248 | TAGGGAATTTTCGTCAATGGGCGCAAGCCTGAACGA GCAATGCCGCGTGAACGAGGAAGGTCTTCGGATCGT AAAGTTCTGTTGAGAGGGAAAAGGGTCACCAGAGGA AATGCTGGTGAAGTGATATTACCTTTCGAGGAAGTCA CGGCTAACTACGTGCC |
| SEQ_ID_NO_90 | R_U01156257 | TAGGGAATTTTCGTCAAGTGGGCGCAAGCCTGAACG AGCAATGCCGCGTGAACGAGGAAGGTCTTCGGATAC GTAAAGTTCTGTTGAGAGGAAAAAGGGTCACCAGAG GAAATGCTGGTGAAGTGATATTACCTTTCGAGGAAGT CACGGCTAACTACGTGCC |
| SEQ_ID_NO_91 | R_U00808203 | TAGGGAATTTTCGTCAATGGGCGCAAGCCTGAACGA GCAATGCCGCGTGAGCGAAGAAGGTCTTCGGATCGT AAAACTCTGTTGCGGGGGAAAAGGAAGGGAAGAGG AAATGCTTTTCTTTTGATGGTACCCCGCCAGAAAGTC ACGGCTAACTACGTGCC |

-continued

| List | OTUName | 16S rRNA Gene V3 Region Sequence |
|---|---|---|
| SEQ_ID_NO_ 92 | R_U00003073 | TAGGGAATTTTCGGCAATGGGCGAAAGCCTGACCGA GCAACGCCGCGTGAGTGAAGAAGGCCTTCGGGTTGT AAAGCTCTGTTGTGAAGGAAGAACGGCTCATAGAGG GAATGCTATGGGAGTGACGGTACTTTACCAGAAAGC CACGGCTAACTACGTGCC |
| SEQ_ID_NO_ 93 | R_U00000235 | TGGGGAATCTTCCGCAATGGACGAAAGTCTGACGGA GCAACGCCGCGTGAGTGATGAAGGATTTCGGTCTGTA AAGCTCTGTTGTTTATGACGAACGTGCAGTGTGTGAA CAATGCATTGCAATGACGGTAGTAAACGAGGAAGCC ACGGCTAACTACGTGCC |

TABLE 2

16S rRNA gene V3 region sequence of those bacteria suppressed/eliminated by berberine.

| List | OTUName | 16S rRNA Gene V3 Region Sequence |
|---|---|---|
| SEQ_ID_NO_ 94 | R_U0004361 9 5 | TGAGGAATATTGGGCAATGGGGGCAACCCTGACCCAG CCATGCCGCGTGAGTGAAGAAGGTTTTCGGATTGTAA AGCTCTTTCGGATGTGACGATGATGACGGTAGCATCT AAAGAAGCCCCGGCAAACTTCGTGCC |
| SEQ_ID_NO_ 95 | R_U0010141 6 | GNGGGAAACCCTGAAGCAGCAACGCCGCGTGGAGGA TGAAGGTTTCGGATTGTAAACTCCTTTGTTAGAGAAG ATAATGACGGTATCTAACGAATAAGCACCGGCTAACT CCGTGCC |
| SEQ_ID_NO_ 96 | R_U0000040 7 | TAGGGAATATTGCTCAATGGGGGAAACCCTGAAGCAG CAACGCCGCGTGGAGGATGAAGGTTTTCGGATTGTAA ACTCCTTTTGTTAGAGAAGATAATGACGGTATCTAAC GAATAAGCACCGGCTAACTCCGTGCC |
| SEQ_ID_NO_ 97 | R_U0080096 6 | TGAGGAATATTGGTCAATGGGCGGAAGCCTGAACCAG CCAAGTAGCGTGCAGGAAGACGGCCCTACGGGTTGTA AACTGCTTTTATGCGGGGATAAAGTGCAATACGTGTA TTGCTTTGCAGGTACCGCATGAATAAGGACCGGCTAA TTCCGTGCC |
| SEQ_ID_NO_ 98 | R_U0113198 2 | TGAGGAATATTGGTCAATGGGCGGAAGCCTGAACCAG CCAAGTAGCGTGCAGGATGACGGCCCTACGGGTTGTA AACTGCTTTTTTGCGGGAATAAAGCGGCTCACGTGTG AGCCTTTGCATGTACCGCACGAATAAGGACCGGCTAA TTCCGTGCC |
| SEQ_ID_NO_ 99 | R_U0079783 9 | TGAGGAATATTGGTCAATGGGCGAGAGCCTGAACCAG CCAAGTAGCGTGCAGGATGACGGCCCTATGGGTTGTA AACTGCTTTTATACGGGGATAAAGTTGGGACGTGTC CCCATTTGTAGGTACCGTATGAATAAGGACCGGCTAA TTCCGTGCC |
| SEQ_ID_NO_ 100 | R_U0000398 1 | TGAGGAATATTGGTCAATGGTCGTGAGACTGAACCAG CCAAGTAGCGTGCGGGATGAAGGCCCTCCGGGTCGTA AACCGCTTTTAGACGGGGATAAAAGGGCATACGTGTA TGCCGTATTGCATGTACCGTCAGAAAAAGGACCGGCT AATTCCGTGCC |
| SEQ_ID_NO_ 101 | R_U0000140 4 | TGAGGAATATTGGTCAATGGGCGAGAGCCTGAACCAG CCAAGTAGCGTGAAGGAAGACTGCCCTATGGGTTGTA AACTTCTTTTATAAGGGAATAAAGAGCGCCACGTGTG GTGTGTTGTATGTACCTTATGAATAAGCATCGGCTAAT TCCGTGCC |
| SEQ_ID_NO_ 102 | R_U0000005 2 | TGAGGAATATTGGTCAATGGGCGTGAGCCTGAACCAG CCAAGCCGCGTGAGGGAAGAAGGCGCCAGGCGTCGT AAACCTCTTTTGCCGGGGAACAAAGGGCGCCACGTGT GGCGTTGTGAGTGTACCCGGAGAAAAAGCATCGGCTA ACTCCGTGCC |
| SEQ_ID_NO_ 103 | R_U0000096 4 | TGAGGAATATTGGTCAATGGGCGTGAGCCTGAACCAG CCAAGCCGCGTGAGGGAGGAAGGCGCCAGGCGTCGT AAACCTCTTTTGCCGGGGAACAAAGGGCGCCACGTGT GGCGTTGTGAGTGTACCCGGAGAAAAAGCATCGGCTA ACTCCGTGCC |

TABLE 2-continued 16S rRNA gene V3 region sequence of those bacteria suppressed/eliminated by berberine.

| List | OTUName | 16S rRNA Gene V3 Region Sequence |
|---|---|---|
| SEQ_ID_NO_ 104 | R_U0004069 0 | TGAGGAATATTGGTCAATGGGCGTGAGCCTGAACCAG CCAAGCCGCGTGAGGGAGGAAGGCGCCAGGCGTCGT AAACCTCTTTTGCCGGGGAACAAAGGGCGCCACGTGT GGCGTTGTGAGTGTACCCGGAGAAAAGCATCGGCTAA CTCCGTGCC |
| SEQ_ID_NO_ 105 | R_U0082399 1 | TGAGGAATATTGGTCAATGGGCGTGAGCCTGAACCAG CCAAGCCGCGTGAGGGAGGAAGGCGCCAGGCGTCGT AAACCTCTTTTGCCGGGGAACAAAGGGCGCCACGTGT GGCGTTGTGAGTGTACCCGGAGAAAAAAGCATCGGCT AACTCCGTGCC |
| SEQ_ID_NO_ 106 | R_U0000080 4 | TGAGGAATATTGGTCAATGGGCGGGAGCCTGAACCAG CCAAGCCGCGTGAGGGAATAAGGCGCCAAGCGTCGTA AACCTCTTTTGTCAGGGAACAAAAGCGGGCACGCGTG CCCGTCCGAGTGTACCTGAAGAAAAAGCATCGGCTAA CTCCGTGCC |
| SEQ_ID_NO_ 107 | R_U0115591 5 | TGAGGAATATTGGTCAATGGGCGAGAGCCTGAACCAG CCAAGCCGCGTGAAGGAAGAAGGTGCTAAGCATTGTA AACTTCTTTTGTCAGGGAACAAAGAGCGCGACGAGTC GCGCCGTGAGTGTACCTGAAGAAAAAGACATCGGCTA ACTCCGTGCC |
| SEQ_ID_NO_ 108 | R_U0045985 0 | TGAGGAATATTGGTCAATGGGCGAGAGCCTGAACCAG CCAAGCCGCGTGAAGGAAGAAGGTGCTAAGCATTGTA AACTTCTTTTGTCAGGGAACAAAGAGCGCGACGAGTC GCGCCGTGAGTGTACCTGAAGAAAAAGCATCGGCTAA CTCCGTGCC |
| SEQ_ID_NO_ 109 | R_U0079809 8 | TGAGGAATATTGGTCAATGGGCGAGAGCCTGAACCAG CCAAGCCGCGTGAAGGAAGAAGGTGCTAAGCATTGTA AACTTCTTTTGTCAGGGAACAAAGAGCGCGACGAGTC GCGCCGTGAGTGTACCTGAAGAAAAAGCATCGGCTAAC TCCGTGCC |
| SEQ_ID_NO_ 110 | R_U0000917 0 | TGAGGAATATTGGTCAATGGTCGGAAGACTGAACCAG CCAAGCCGCGTGAAGGAAGAAGGTGCTCGGCATCGTA AACTTCTTTTGTCAGGGAACAAAGGGCGGTACGTGTA CCGCTGTGAGTGTACCTGAAGAAAAAGCATCGGCTAA CTCCGTGCC |
| SEQ_ID_NO_ 111 | R_U0110215 3 | TGAGGAATATTGGTCAATGGTCGGAAGACTGAACCAG CCAAGCCGCGTGAAGGAAGAAGGTGCTCGGCATCGTA AACTTCTTTTGTCAGGGAACAAAGGGCGGTACGTGTA CCGCTGTGAGTGTACCTGAAGAAAAAGCATCGGCTA ACTCCGTGCC |
| SEQ_ID_NO_ 112 | R_U0000623 0 | TGAGGAATATTGGTCAATGGGCGTGAGCCTGAACCAG CCAAGCCGCGTGAAGGAAGAAGGTGCAGGGCATCGT AAACTTCTTTTGCCGGGGAACAATAAGCGGGACTAGT CCCGCGACGAGTGTACCCGGAGAAAAAGCATCGGCTA ACTCCGTGCC |
| SEQ_ID_NO_ 113 | R_U0046534 4 | TGAGGAATATTGGTCAATGGGCGTGAGCCTGAACCAG CCAAGCCGCGTGAAGGAAGAAGGTGCAGGGCATCGT AAACTTCTTTTGCCGGGGAACAATAAGCGGGACTAGT CCCGCGACGAGTGTACCCGGAGAAAAGACATCGGCTA ACTCCGTGCC |
| SEQ_ID_NO_ 114 | R_U0000120 2 | TGAGGAATATTGGTCAATGGTCGGGAGACTGAACCAG CCAAGCCGCGTGAGGGATGGAGGTACAGAGTATCGTA AACCTCTTTTGTCAGGGAACAAAGGGCGCCACGTGTG GCGCTATGAGGGTACCTGAAGAAAAAGCATCGGCTAA CTCCGTGCC |
| SEQ_ID_NO_ 115 | R_U0000138 4 | TGAGGAATATTGGTCAATGGGAGAGATCCTGAACCAG CCAAGCCGCGTGAGGGAAGACGGCACTACGTGTTGTA AACCTCTTTTGCCGGGGAACAAAGCGGGGACGCGTC CCGTCCGCGTGTACCCGGAGAAAAAGCATCGGCTAA CTCCGTGCC |

TABLE 2-continued 16S rRNA gene V3 region sequence of those bacteria suppressed/eliminated by berberine.

| List | OTUName | 16S rRNA Gene V3 Region Sequence |
|---|---|---|
| SEQ_ID_NO_ 116 | R_U00802799 | TGAGGAATATTGGTCAATGGGCGGGAGCCTGAACCAG CCAAGTCGCGTGAGGGAAGACGGCCCTACGGGTTGTA AACCTCTTTTGTCGGGGAGCAAAGAGCGCCACGCGTG GCGAGATGAGAGTACCCGAAGAAAAAGCATCGGCTA ACTCCGTGCC |
| SEQ_ID_NO_ 117 | R_U00808453 | TGAGGAATATTGGTCAATGGGCGGGAGCCTGAACCAG CCAAGTCGCGTGAGGGAAGACGGCCCTACGGGTTGTA AACCTCTTTTGTCGGGGAGCAAAGAGCGCCACGCGTG GCGAGATGAGAGTACCCGAAGAAAAAGACATCGGCT AACTCCGTGCC |
| SEQ_ID_NO_ 118 | R_U00026711 | TGAGGAATATTGGTCAATGGGCGGGAGCCTGAACCAG CCAAGCCGCGTGAAGGAAGACGGCCCTACGGGTTGTA AACTTCTTTTGTTGCAGGACAACACCCCGGACGCGTCC GGGCATGAGTGTATGCAAAGAAAAAGCATCGGCTAAC TCCGTGCC |
| SEQ_ID_NO_ 119 | R_U00000650 | TGAGGAATATTGGTCAATGGGCGGGAGCCTGAACCAG CCAAGCCGCGTGAGGGAATAAGGCCCTACGGGTCGTA AACCTCTTTTGTCGGGGAACAAAACCGGAGACGAGTC TCCGGCTGCGTGTACCCGAAGAAAAAGCATCGGCTAA CTCCGTGCC |
| SEQ_ID_NO_ 120 | R_U00000839 | TGAGGAATATTGGTCAATGGGCGGGAGCCTGAACCAG CCAAGCCGCGTGAGGGAAGAAGGCGCTCAGCGTCGTA AACCTCTTTAGCCGGGGAACAAAGAGCTGCTCGGGAA GCAGCGTTGAGCGTACCCGGAGAATAAGCATCGGCTA ACTCCGTGCC |
| SEQ_ID_NO_ 121 | R_U01157930 | TGAGGAATATTGGTCAATGGGCGGAAGCCTGAACCAG CCAAGTCGCGTGAGGGACGACGGTCCTACGGATTGTA AACCTCTTTTGCCGGGGAGCAATGCGCGGTACGCGTA CCGCGACGGAGAGTACCCGGAGAAAAAGCATCGGCT AACTCCGTGCC |
| SEQ_ID_NO_ 122 | R_U00798420 | TGAGGAATATTGGTCAATGGGCGAGAGCCTGAACCAG CCAAGTCGCGTGAGGGAAGACGGCCCTACGGGTTGTA AACCTCTTTTGTCGGGGAGCAAAGAGCGCCACGCGTG GCGAGATGAGAGTACCCGAAGAAAAAGACATCGGCTA ACTCCGTGCC |
| SEQ_ID_NO_ 123 | R_U00001933 | TGAGGAATATTGGTCAATGGGCGCGAGCCTGAACCAG CCAAGTCGCGTGAGGGAAGACGGCCCTACGGGTTGTA AACCTCTTTTGTCGGGGAGCAAGGACTGCCACGAGTG GCAGGGCGAGAGTACCCGAAGAAAAAGCATCGGCTA ACTCCGTGCC |
| SEQ_ID_NO_ 124 | R_U00001491 | TGAGGAATATTGGTCAATGGGCGGGAGCCTGAACCAG CCAAGTCGCGTGAGGGAAGACGGTCTTACGGATTGTA AACCTCTTTTGCCGGGGAGCAAAGGGCGCCACGCGTG GCGTTTCGAGAGTACCCGGAGAAAAAGCATCGGCTAA CTCCGTGCC |
| SEQ_ID_NO_ 125 | R_U00006476 | TGAGGAATATTGGTCAATGGCCGAGAGGCTGAACCAG CCAAGTCGCGTGAGGGAAGACGGTCCTATGGATTGTA AACCTCTTTTGTCGGGGAGCAAAAGGCGTCACGTGTG ACGCTATGAGAGTACCCGAAGAAAAAGCATCGGCTAA CTCCGTGCC |
| SEQ_ID_NO_ 126 | R_U00001502 | TGAGGAATATTGGTCAATGGCCGGAAGGCTGAACCAG CCAAGCCGCGTGAGGGAGGAAGGCGCAGAGCGTCGC AGACCTCTTTTGCCGGGGGACAAAAGGCCGGACTCGT CCGGTCCTGAGGGTACCCGGAGAAAAAGCATCGGCTA ACTCCGTGCC |
| SEQ_ID_NO_ 127 | R_U00001504 | TGAGGAATATTGGTCAATGGGCGCGAGCCTGAACCAG CCAAGTCGCGTGAGGGATGACGGCCCTACGGGTTGTA AACCTCTTTTGTCGGGGAGCAAATTCCGTTACGTGTAA CGGAGTCGAGAGTACCCGAAGAAAAAGCATCGGCTA ACTCCGTGCC |

TABLE 2-continued 16S rRNA gene V3 region sequence of those bacteria suppressed/eliminated by berberine.

| List | OTUName | 16S rRNA Gene V3 Region Sequence |
|---|---|---|
| SEQ_ID_NO_ 128 | R_U00000609 | TGAGGAATATTGGTCAATGGGCGGAAGCCTGAACCAG CCAAGTCGCGTGAGGGAAGACGGTCCTATGGATTGTA AACCTCTTTTGCAGGGGAGCAAGGCACGGTACGTGTA CCGTGAAGGAGAGTACCCTGAGAAAAAGCATCGGCTA ACTCCGTGCC |
| SEQ_ID_NO_ 129 | R_U00009261 | TGAGGAATATTGGTCAATGGGCGGAAGCCTGAACCAG CCAAGTCGCGTGAGGGAAGACGGTCCTATGGATTGTA AACCTCTTTTGTCGGGGAGCAAAGCCGCTCACGTGTG AGCGGAAGGAGAGTACCCGAAGAAAAAGCATCGGCT AACTCCGTGCC |
| SEQ_ID_NO_ 130 | R_U01136992 | TGAGGAATATTGGTCAATGGGCGGAAGCCTGAACCAG CCAAGTCGCGTGAGGGAGGACGGTCCTATGGATTGTA AACCTCTTTTGTCGGGGAGCAAAGCCGCTCACGTGTG AGCGGAAGGAGAGTACCCGAAGAAAAAGCATCGGCT AACTCCGTGCC |
| SEQ_ID_NO_ 131 | R_U00000497 | TGAGGAATATTGGTCAATGGCCGAAGGGCTGAACCAG CCAAGTCGCGTGAGGGAAGACGGCCCTACGGGTTGTA AACCTCTTTTGCCGGGGAGCAAAGGCGGTCACTGGTG ACCGGATGAGAGTACCGGAGAAAAAGCATCGGCTA ACTCCGTGCC |
| SEQ_ID_NO_ 132 | R_U00000886 | TGAGGAATATTGGTCAATGGGCGAGAGCCTGAACCAG CCAAGTCGCGTGAGGGAAGACGGTCCTATGGATTGTA AACCTCTTTTGTCAGGGAGCAAGGAGGGCCACGAGTG GCGCTTCGGAGAGTACCTGAAGAAAAAGCATCGGCTA ACTCCGTGCC |
| SEQ_ID_NO_ 133 | R_U01143292 | TGAGGAATATTGGTCAATGGCCGAGAGGCTGAACCAG CCAAGTCGCGTGAGGGAAGACGGCCCTACGGGTTGTA AACCTCTTTTGTCGGGGAGCAAACAGCGCAACGCGCT TGCGCATTGAGAGTACCCGAAGAAAAAGCATCGGCTA ACTCCGTGCC |
| SEQ_ID_NO_ 134 | R_U00803188 | TGAGGAATATTGGTCAATGGGCGAGAGCCTGAACCAG CCAAGTCGCGTGAGGGAAGACGGCCCTACGGGTTGTA AACCTCTTTTGTCGGGGAGCAAAGAGCGCCACGCGTG GCGAGATGAGAGTACCCGAAGAAAAAGCATCGGCTA ACTCCGTGCC |
| SEQ_ID_NO_ 135 | R_U00008782 | TGAGGAATATTGGTCAATGGGCGAGAGCCTGAACCAG CCAAGTCGCGTGAGGGAAGACGGCCCTATGGGTTGTA AACCTCTTTTGCCGGGGAGCAAAGAACCGCACGTGTG CGGTCTGGAGAGTACCGGAGAAAAAGCATCGGCTAA CTCCGTGCC |
| SEQ_ID_NO_ 136 | R_U00001406 | TGAGGAATATTGGTCAATGGGCGGAAGCCTGAACCAG CCAAGTCGCGTGAGGGAATAAGGCCCTAAGGGTCGTA AACCTCTTTTGCCGGGGAGCAATGGTTCGCTTGCGAG CGGACAGGGAGAGTACCCGGAGAAAAAGCATCGGCT AACTCCGTGCC |
| SEQ_ID_NO_ 137 | R_U00030880 | TGAGGAATATTGGTCAATGGCCGTAAGGCTGAACCAG CCAAGTCGCGTGAGGGAAGACGGCCCTACGGGTTGTA AACCTCTTTTGCCGGGGAGCAAAAGGCGCCACGCGTG GCGTTTCGAGAGTACCGGAGAAAAAGCATCGGCTAA CTCCGTGCC |
| SEQ_ID_NO_ 138 | R_U00450938 | TGAGGAATATTGGTCAATGGGCGTAAGCCTGAACCAG CCAAGTCGCGTGAGGGAAGACGGCCCTATGGGTTGTA AACCTCTTTTGTCGGGGAGCAAAGCCGCCCACGTGTG GGCGGAAGGAGAGTACCCGAAGAAAAAGCATCGGCT AACTCCGTGCC |
| SEQ_ID_NO_ 139 | R_U00009763 | TGAGGAATATTGGTCAATGGGCGTAAGCCTGAACCAG CCAAGTCGCGTGAGGGAAGACGGCCCTATGGGTTGTA AACCTCTTTTGTCGGGGAGCAAAGCCGCCCACGAGTG GGCGGAAGGAGAGTACCCGAAGAAAAAGCATCGGCT AACTCCGTGCC |

TABLE 2-continued 16S rRNA gene V3 region sequence of those bacteria suppressed/eliminated by berberine.

| List | OTUName | 16S rRNA Gene V3 Region Sequence |
|---|---|---|
| SEQ_ID_NO_ 140 | R_U01155495 | TGAGGAATATTGGTCAATGGGCGTAAGCCTGAACCAGCCAAGTCGCGTGAGGGAAGACGGCCCTATGGGTTGTAAACCTCTTTTGTCGGGGAGCAAAGCCGCCCACGAGTGGGCGGAAGGAGAGTACCCGAAGAAAAGACATCGGCTAACTCCGTGCC |
| SEQ_ID_NO_ 141 | R_U00798694 | TGAGGAATATTGGTCAATGGGCGTAAGCCTGAACCAGCCAAGTCGCGTGAGGGAAGACGGCCCTATGGGTTGTAAACCTCTTTTGTCGGGGAGCAAAGCCGCCCACGAGTGGGCGGAAGGAGAGTACCCGAAGAAAAGACATCGGCTAACTCCGTGCC |
| SEQ_ID_NO_ 142 | R_U00802360 | TGAGGAATATTGGTCAATGGGCGGTAGCCTGAACCAGCCAAGTCGCGTGAGGGAAGACGGTCCTATGGATTGTAAACCTCTTTTGCCGGGGAGCAAGGCCATGTACGTGTACGTGGCCTGAGAGTACCCGGAGAAAAGCATCGGCTAACTCCGTGCC |
| SEQ_ID_NO_ 143 | R_U01162782 | TGAGGAATATTGGTCAATGGGCGCGAGCCTGAACCAGCCAAGTCGCGTGAGGGAAGACGGTCCTAAGGATTGTAAACCTCTTTTGTCAGGGAGCAAGGAGCGCCACGTGTGGCGCGGCGAGAGTACCTGAAGAAAAGACATCGGCTAACTCCGTGCC |
| SEQ_ID_NO_ 144 | R_U00002709 | TGAGGAATATTGGTCAATGGGCGCGAGCCTGAACCAGCCAAGTCGCGTGAGGGAAGACGGTCCTAAGGATTGTAAACCTCTTTTGTCAGGGAGCAAGGAGCGCCACGTGTGGCGCGGCGAGAGTACCTGAAGAAAAGCATCGGCTAACTCCGTGCC |
| SEQ_ID_NO_ 145 | R_U00005232 | TGAGGAATATTGGTCAATGGGCGAGAGCCTGAACCAGCCAAGTCGCGTGAGGGAAGACAGTCCTATGGATTGTAAACCTCTTTTGCCGGGGAGCAAAGAGCGGCACGTGTGCCGCGCCGAGAGTACCCGGAGAAAAGCATCGGCTAACTCCGTGCC |
| SEQ_ID_NO_ 146 | R_U00000305 | TGAGGAATATTGGTCAATGGGCGAGAGCCTGAACCAGCCAAGTCGCGTGAGGGAAGACGGTCCTATGGATTGTAAACCTCTTTTGCCGGGGAGCAAAGAGCGGCACGTGTGCCGCGCCGAGAGTACCCGGAGAAAAGCATCGGCTAACTCCGTGCC |
| SEQ_ID_NO_ 147 | R_U00006821 | TGAGGAATATTGGTCAATGGGCGAGAGCCTGAACCAGCCAAGTCGCGTGAGGGAAGACGGTCCTATGGATTGTAAACCTCTTTTGTCGGGGAGCAACGAAGGCACGTGTGCCAGAAGCGAGATTACCCGAAGAAAAGCATCGGCTAACTCCGTGCC |
| SEQ_ID_NO_ 148 | R_U01199405 | TGAGGAATATTGGTCAATGGGCGAGAGCCTGAACCAGCCAAGTCGCGTGAGGGAAGACGGTCCTATGGATTGTAAACCTCTTTTGTCGGGGAGCAACGAAGGCACGTGTGCCAGAAGCGAGATTACCCGAAGAAAAGACATCGGCTAACTCCGTGCC |
| SEQ_ID_NO_ 149 | R_U00006150 | TGAGGAATATTGGTCAATGGGCGAGAGCCTGAACCAGCCAAGTCGCGTGAGGGAAGACGGTCCTATGGATTGTAAACCTCTTTTGTCGGGGAGCAACGAAGGCACGTGTGCCTGAAGCGAGATTACCCGAAGAAAAGCATCGGCTAACTCCGTGCC |
| SEQ_ID_NO_ 150 | R_U00000206 | TGAGGAATATTGGTCAATGGGCGGGAGCCTGAACCAGCCAAGTCGCGTGAGGGAAGACGGTCCTATGGATTGTAAACCTCTTTTGTCGGGGAGCAAAGAGGCCACGTGTGGTCAAAAGCGAGAGTACCCGAAGAAAAGCATCGGCTAACTCCGTGCC |
| SEQ_ID_NO_ 151 | R_U01150673 | TGAGGAATATTGGTCAATGGGCGGGAGCCTGAACCAGCCAAGTCGCGTGAGGGAAGACGGTCCTATGGATTGTAAACCTCTTTTGTCGGGGAGCAAAGAGGCCACGTGTGGTCAAAAGCGAGAGTACCCGAAGAAAAAGACATCGGCTAACTCCGTGCC |

TABLE 2-continued 16S rRNA gene V3 region sequence of those bacteria suppressed/eliminated by berberine.

| List | OTUName | 16S rRNA Gene V3 Region Sequence |
|---|---|---|
| SEQ_ID_NO_ 152 | R_U0080581 1 | TGAGGAATATTGGTCAATGGGCGGAAGCCTGAACCAG CCAAGTCGCGTGAGGGAAGACGGTCCTATGGATTGTA AACCTCTTTTGTCGGGGAGCAAGGATCCGCACGAGTG CGGAGGCGAGAGTACCCGAAGAAAAAGCATCGGCTA ACTCCGTGCC |
| SEQ_ID_NO_ 153 | R_U0119947 1 | TGAGGAATATTGGTCAATGGGCGGAAGCCTGAACCAG CCAAGTCGCGTGAGGGAAGACGGTCCTATGGATTGTA AACCTCTTTTGTCGGGGAGCAAGGATCCGCACGAGTG CGGAGGCGAGAGTACCCGAAGAAAAAGACATCGGCT AACTCCGTGCC |
| SEQ_ID_NO_ 154 | R_U0000006 8 | TGAGGAATATTGGTCAATGGGCGAGAGCCTGAACCAG CCAAGTCGCGTGAGGGAAGAATGGTCTATGGCCTGTA AACCTCTTTTGTCAGGGAAGAATAAGGATGACGAGTC ATTCGATGCCAGTACTTGACGAATAAGCATCGGCTAA CTCCGTGCC |
| SEQ_ID_NO_ 155 | R_U0000555 9 | TGAGGAATATTGGTCAATGGACGCAAGTCTGAACCAG CCATGCCGCGTGCAGGAAGACGGCTCTATGAGTTGTA AACTGCTTTTGTACGAGGGTAAACCCGGATACGTGTA TCCGGCTGAAAGTATCGTACGAATAAGGATCGGCTAA CTCCGTGCC |
| SEQ_ID_NO_ 156 | R_U0080196 1 | CTAAGGATATTCCGCAACGGGCGGAAGCCCGGCGGAG CGACGCCGCGTGGACGAGGAAGGCCGGAAGGTTGCA GAGTCCTTTTGCGGGGGAAGAAGGAGCCGCGGAGGG AATGCCGCGGCGGCGACCGAACCCCGCGAATAAGGG GCGGCTAATTACGTGCC |
| SEQ_ID_NO_ 157 | R_U0000012 6 | TGGGGAATATTGCACAATGGGCGCAAGCCTGATGCAG CGACGCCGCGTGCGGGATGGAGGCCTTCGGGTTGTAA ACCGCTTTTGTTCAAGGGCAAGGCACGGCTTCGGGCC GTGTTGAGTGGATTGTTCGAATAAGCACCGGCTAACT ACGTGCC |
| SEQ_ID_NO_ 158 | R_U0016410 5 | TGGGGAATATTGCACAATGGGGGAACCCTGATGCAG CGACGCCGCGTGGGTGAAGAAGTATTTCGGTATGTAA AGCCCTATCAGCAGGGAAGAAAAAGACGGTACCTGA CTAAGAAGCCCCGGCTAACTACGTGCC |
| SEQ_ID_NO_ 159 | R_U0011807 8 | TGGGGAATATTGCACAATGGGGGAAACCCTGATGCAG CGACGCCGCGTGAAGGAAGAAGTATTTCGGTATGTAA ACTTCTATCAGCAGGGAAGAAAATGACGGTATCTGAC TAAGAAGCCCCGGCTAACTACGTGCC |
| SEQ_ID_NO_ 160 | R_U0114837 6 | TGGGGGATATTGCACAATGGGGGAAACCCTGATGCAG CGACGCCGCGTGGGTGAAGAAGTATTTCGGTATGTAA AGCCCTATCAGCAGGGAAGAAAATGACAGTACCTGAA TAAGAAGCCCCGGCTAACTACGTGCC |
| SEQ_ID_NO_ 161 | R_U0044400 2 | TGGGGGATATTGCACAATGGGGGAACCCTGATGCAG CGACGCCGCGTGGGTGAAGAAGTATTTCGGTATGTAA AGCCCTATCAGCAGGGAAGAAAGAAGACGGTACCTG AGTAAGAAGCCCCGGCTAACTACGTGCC |
| SEQ_ID_NO_ 162 | R_U0113039 6 | TGGGGAGTATTGCACAATGGGGGAAACCCGTGATGCA GCGACGCCGCGTGAGTGAAGAAGTATTTCGGTATGTA AAGCTCTATCAGCAGGGAAGAAAATAGACGGTACCTG ACTAAGAAGCCCCGGCTAACTACGTGCC |
| SEQ_ID_NO_ 163 | R_U0001158 2 | TGGGGATATTGGACAATGGGGGAACCCTGATCCAG CGACGCCGCGTGAGTGAAGAAGTATTTCGGTATGTAA AGCTCTATCAGCAGGGAAGAAAGAAATGACGGTACCT GACCAAGAAGCCCCGGCTAACTACGTGCC |
| SEQ_ID_NO_ 164 | R_U0043988 8 | TGGGGAATATTGCACAATGGGGGAAACCCTGATGCAG CGACGCCGCGTGAGTGAAGAAGTAATTCGTTACGTAA AGCTCTATCAGCAGGGAAGAAAAAGAAATGACGGTA CCTGATTAAGAAGCCCCGGCTAACTACGTGCC |
| SEQ_ID_NO_ 165 | R_U0116361 7 | TGGGGAATATTGCACAATGGGGGAACCCTGATGCAG CAATGCCGCGTGAGTGAAGAAGTATTTCGGTATGTAA AGCTCTATCAGCAGGGAAGAAAAAAGACGGTACCTG ACTAAGAAGCCCCGGCTAACTACGTGCC |

TABLE 2-continued 16S rRNA gene V3 region sequence of those bacteria suppressed/eliminated by berberine.

| List | OTUName | 16S rRNA Gene V3 Region Sequence |
|---|---|---|
| SEQ_ID_NO_ 166 | R_U0002930 6 | TGGGGAATATTGCACAATGGGGGAAACCCTGATGCAG CAATGCCGCGTGAGTGAAGAAGTATTTCGGTATGTAA AGCTCTATCAGCAGGGAAGAAAAAAGACGGTACCTG ACTAAGAAGCCCCGGCTAACTACGTGCC |
| SEQ_ID_NO_ 167 | R_U0079798 5 | TGGGGAATATTGCACAATGGAGGAAACTCTGATGCAG CGACGCCGCGTGAGTGAAGAAGTAATTCGTTACGTAA AGCTCTATCAGCAGGGAAGAAAAAATGACGGTACCTG ACTAAGAAGCACCGGCTAAATACGTGCC |
| SEQ_ID_NO_ 168 | R_U0117359 4 | TGGGGAATATTGCACAATGGAGGAAACTCTGATGCAG CGACGCCGCGTGAGTGAAGAAGTAATTCGTTACGTAA AGCTCTATCAGCAGGGAGAAAAAAATGACGGTACCTG ACTAAGAAGCACCGGCTAAATACGTGCC |
| SEQ_ID_NO_ 169 | R_U0000928 2 | TGGGGGATATTGCACAATGGGGGAAACCCTGATGCAG CGACGCCGCGTGAGTGAAGAAGTATTTCGGTATGTAA AGCTCTATCAGCAGGGAAGAAGATGACAGTACCTGAC TAAGAAGCCCCGGCTAACTACGTGCC |
| SEQ_ID_NO_ 170 | R_U0016528 8 | TGGGGAATATTGCACAATGGGGGGAAACCCTGATGCAG CAACGCCGCGTGAGTGAAGAAGTATTTCGGTATGTAA AGCTCTATCAGCAGGGAAGAAAATGACGGTACCTGAC TAAGAAGCTCCGGCTAAATACGTGCC |
| SEQ_ID_NO_ 171 | R_U0000348 1 | TGGGGAATATTGCACAATGGGGGAAACCCTGATGCAG CGATGCCGCGTGGAGGAAGAAGGTTTTCGGATTGTAA ACTCCTGTCTTAAAGGACGATAATGACGGTACTTTAG GAGGAAGCTCCGGCTAACTACGTGCC |
| SEQ_ID_NO_ 172 | R_U0000354 8 | TGGGGAATATTGCACAATGGGCGCAAGCCTGATGCAG CGACGCCGCGTGAGTGAAGAAGTATTTCGGTATGTAA AGCTCTATCAGCAGGGAAGAAGAATGACGGTACCTGA CTAAGAAGCACCGGCTAAATACGTGCC |
| SEQ_ID_NO_ 173 | R_U0079847 2 | TGGGGAATATTGCACAATGGAGGGAACTCTGATGCAG CGACGCCGCGTGAGTGAAGAAGTAATTCGTTATGTAA AGCTCTGTCAGCAGGGAAGAAAGTGACGGTACCTGAA AAAGAAGCTCCGGCTAAATACGTGCC |
| SEQ_ID_NO_ 174 | R_U0080400 5 | TGGGGAATATTGCACAATGGGGGAAACCCTGATGCAG CGACGCCGCGTGAGTGAAGAAATATTTCGGTATGTAA AGCTCTATCAGCAGGGAAGAAAATGACGGTACCTGAG TAAGAAGCCCCGGCTAACTACGTGCC |
| SEQ_ID_NO_ 175 | R_U0016481 4 | TGGGGAATATTGCACAATGGGGGAAACCCTGATGCAG CGACGCCGCGTGAGTGAAGAAGTAATTCGTTATGTAA AGCTCTATCAGCAAGGAAGAAAAAAGACGGTACTTGA CTAAGAAGCCCCGGCTAAATACGTGCC |
| SEQ_ID_NO_ 176 | R_U0050740 9 | TGGGGATATTGCACAATGGGGGAAACCCTGATGCAG CGACGCCGCGTGGGTGAAGAAGTATTTCGGTATGTAA AGCCCTATCAGCAGGGAAGAAGATGACAGTACCTGAC TAAGAAGCCCCGGCTAACTACGTGCC |
| SEQ_ID_NO_ 177 | R_U0000995 2 | TGGGGGATATTGCACAATGGGGGGAACCCTGATGCAG CGACGCCGCGTGGGTGAAGGAGTACTCCGGTATGTAA AGCCCTATCGGCAGGGAAGAAGATGACGGTACCTGAC TAAGAAGCTCCGGCTAAATACGTGCC |
| SEQ_ID_NO_ 178 | R_U0083254 9 | TGGGGGATATTGCACAATGGGGGAAACCCTGATGCAG CGACGCCGCGTGAGTGAAGAAGTATTTCGGTATGTAA AGCTCTATCAGCAGGGAAGAAAGTGACAGTACCTGAG TAAGAAGCCCCGGCTAACTACGTGCC |
| SEQ_ID_NO_ 179 | R_U0001347 6 | TGGGGGATATTGGACAATGGGGGGAACCCTGATCCAG CGACGCCGCGTGAGTGAAGAAGTATCTCGGTATGTAA AGCTCTATCAGCAGGGAAGAAAGAAATGACGGTACCT GAGTAAGAAGCCCCGGCTAACTACGTGCC |
| SEQ_ID_NO_ 180 | R_U0000001 2 | TGGGGGATATTGGACAATGGGGGGAACCCTGATCCAG CGACGCCGCGTGAGTGAAGAAGTATCTCGGTATGTAA AGCTCTGTCAGCAGGGAAGAAAGAAATGACGGTACCT GACCAAGAAGCCCCGGCTAACTACGTGCC |

TABLE 2-continued 16S rRNA gene V3 region sequence of those bacteria suppressed/eliminated by berberine.

| List | OTUName | 16S rRNA Gene V3 Region Sequence |
|---|---|---|
| SEQ_ID_NO_ 181 | R_U0080806 5 | TGGGGGATATTGGACAATGGGGGGAACCCTGATCCAG CGACGCCGCGTGAGTGAAGAAGTATTTCGGTATGTAA AGCTCTGTCAGCAGGGAAGAAAGAAATGACGGTACCT GAAGAAGAAGCCCCGGCTAACTACGTGCC |
| SEQ_ID_NO_ 182 | R_U0081662 5 | TGGGGGATATTGCACAATGGGGGGAACCCTGATGCAG CGACGCCGCGTGGGTGAAGGAGTGCTTCGGCATGTAA AGCCCTATCGGCAGGGAAGAAGAAGGACGGTACCTG ACTAAGAAGCCCCGGCTAACTACGTGCC |
| SEQ_ID_NO_ 183 | R_U0016460 5 | TGGGGGATATTGCACAATGGGGGGAACCCTGATGCAG CGACGCCGCGTGGGTGAAGAAGCGCCCCGGCGCGTAA AGCCCTATCGGCAGGGAAGAAGATGACGGTACCTGGC TAAGAAGCCCCGGCTAACTACGTGCC |
| SEQ_ID_NO_ 184 | R_U0023209 6 | GGGGATATTGCACAATGGGGGAACCCGTGATGCAGCG ACGCCGCGTGGGTGAAGAAGCGCCCCGGCGCGTAAA GCCCTATCGGCAGGGAAGAAGATGACGGTACCTGGCT AAGAAGCCCCGGCTAACTACGTGCC |
| SEQ_ID_NO_ 185 | R_U0003150 2 | TGGGGAATATTGCACAATGGGGGGAACCCTGATGCAG CGACGCCGCGTGAGTGAAGAAGTATTTCGGTATGTAA AGCTCTATCAGCAGGAACGAAGAAGACGGTACCTGAC TAAGAAGCCCCGGCTAACTACGTGCC |
| SEQ_ID_NO_ 186 | R_U0113068 3 | TGGGGAATATTGCACAATGGGGGGAACCCTGATGCAG CGACGCCGCGTGAGTGAAGAAGTAATTCGTTACGTAA AGCTCTATCAGCAGGAAAGAAAGAAGACGGTACCTG ACTAAGAAGCCCCGGCTAACTACGTGCC |
| SEQ_ID_NO_ 187 | R_U0113935 5 | TGGGGGATATTGCACAATGGGGGAAACCCTGATGCAG CGACGCCGCGTGAGCGAAGAAGTATTTCGGTATGTAA AGCTCTATCAGCGGGGAAGAGAATGACGGTACCCGAC TAAGAAGCTCCGGCTAAATACGTGCC |
| SEQ_ID_NO_ 188 | R_U0085159 9 | TGGGGGATATTGCACAATGGGGGAAACCCTGATGCAG CGACGCCGCGTGAGTGAAGAAGTATTTCGGTATGTAA AGCTCTATCAGCAGGGAAGAAGATGACAGTACCTGAA TAAGAAGCCCCGGCTAACTACGTGCC |
| SEQ_ID_NO_ 189 | R_U0001004 7 | TGGGGAATATTGCACAATGGGGGGAACCCTGATGCAG CGACGCCGCGTGAGCGAAGAAGTATTTCGGTATGTAA AGCTCTATCAGCAGGGAAGAAAATGACGGTACCTGAC TAAGAAGCCCCGGCTAACTACGTGCC |
| SEQ_ID_NO_ 190 | R_U0016413 5 | TGGGGAATATTGGGCAATGGGCGCAAGCCTGACCCAG CAACGCCGCGTGAGCGATGAAGGTCTTCGGATTGTAA AGCTCTGTCGCAGGGGACGAAGTATGACGGTACCCTG TAAGAAAGCCCCGGCAAACTACGTGCC |
| SEQ_ID_NO_ 191 | R_U0003405 0 | TGGGGAATATTGCACAATGGGGGAAACCCTGATGCAG CGACGCCGCGTGAGCGAAGAAGTATCTCGGTATGTAA AGCTCTATCAGCAGGGAAGAAGAATGACGGTACCTGA GTAAGAAGCACCGGCTAAATACGTGCC |
| SEQ_ID_NO_ 192 | R_U0113967 0 | TGGGGGATATTGCACAATGGGGGAAACCCTGATGCAG CGACGCCGCGTGAGCGAAGAAGTATTTCGGTATGTAA AGCTCTATCAGCAGGGAAGAAAATGACGGTACCTGAA CAAGAAGCTCCGGCTAAATACGTGCC |
| SEQ_ID_NO_ 193 | R_U0003367 0 | TGGGGAATATTGCACAATGGGGGGAACCCTGATGCAG CAACGCCGCGTGAGTGAAGAAGTATTTCGGTATGTAA AGCTCTATCAGCAGGGAAGAAAATGACGGTACCTGAC TAAGAAGCACCGGCTAAATACGTGCC |
| SEQ_ID_NO_ 194 | R_U0003369 3 | TGGGGGATATTGCACAATGGGGGGAACCCTGATGCAG CGACGCCGCGTGAGTGAAGGAGTACTTCGGTATGTAA AGCTCTATCAGCAGGGAAGAAGCAAGACGGTACCTGA CCAAGAAGCCCCGGCTAACTACGTGCC |
| SEQ_ID_NO_ 195 | R_U0000258 3 | TGGGGAATATTGCACAATGGGGGGAACCCTGATGCAG CGACGCCGCGTGAGCGAAGAAGTATTTCGGTATGTAA AGCTCTATCAGCAGGGAAGAAAATGACGGTACCTGAC TAAGAAGCCCCGGCTAACTACGTGCC |

TABLE 2-continued 16S rRNA gene V3 region sequence of those bacteria suppressed/eliminated by berberine.

| List | OTUName | 16S rRNA Gene V3 Region Sequence |
|---|---|---|
| SEQ_ID_NO_ 196 | R_U000441<br>9 | 2TGGGGAATATTGGGCAATGGAGGCAACTCTGACCCAG<br>CAACGCCGCGTGAGCGATGAAGGTCTTCGGATTGTAA<br>AGCTCTTTAAGTGGGGACGAAGAAAGTGACTGTACCC<br>ACAGAATAAGCCTCGGCTAACTACGTGCC |
| SEQ_ID_NO_ 197 | R_U000426<br>3 | 5TGGGGAATATTGGGCAATGGAGGAAACTCTGACCCAG<br>CAACGCCGCGTGAATGATGAAGGTCTTCGGATTGTAA<br>AGTTCTTTTCTAAGGGAAGAAGAAAGTGACGGTACCT<br>TAGGAATAAGCCTCGGCTAACTACGTGCC |
| SEQ_ID_NO_ 198 | R_U008553<br>8 | 2TGGGGAATATTGCACAATGGGGGAACCCTGATGCAG<br>CAATGCCGCGTGGGTGAAGAAGTACCCCGGTATGTAA<br>AGCCCTATCAGCAGGGAAGAAAATGACGGTACCTGGC<br>TAAGAAGCCCCGGCTAACTACGTGCC |
| SEQ_ID_NO_ 199 | R_U001641<br>6 | 9TGGGGAATATTGCACAATGGGGGAAACCCTGATGCAG<br>CGACGCCGCGTGAGCGAAGAAGTATTTCGGTATGTAA<br>AGCTCTATCAGCAAGGAAGATAATGACGGTACTTGAC<br>TAAGAAGCTCCGGCTAAATACGTGCC |
| SEQ_ID_NO_ 200 | R_U001642<br>6 | 5TGGGGAATATTGCACAATGGGCGAAAGCCTGATGCAG<br>CAACGCCGCGTGAAGGAAGAAGGGTTTCGGCTCGTAA<br>ACTTCTATCAACAGGGACGAAGGAAGTGACGGTACCT<br>GAATAAGAAGCCCCGGCTAACTACGTGCC |
| SEQ_ID_NO_ 201 | R_U000030<br>9 | 7TGGGGAATATTGCACAATGGGGGAAACCCTGATGCAG<br>CAACGCCGCGTGAGTGAAGAAGTATTTCGGTATGTAA<br>AGCTCTATCAGCAGGGAAGAAAATGACGGTACCTGAC<br>TAAGAAGCTCCGGCTAAATACGTGCC |
| SEQ_ID_NO_ 202 | R_U000024<br>4 | 0TGGGGAATATTGCACAATGGGGGAAACCCTGATGCAG<br>CGACGCCGCGTGGAGGAAGAAGGCCCTCGGGTTGTAA<br>ACTCCTGTCTTTGGGGACGATAATGACGGTACCCAAG<br>GAGGAAGCCACGGCTAACTACGTGCC |
| SEQ_ID_NO_ 203 | R_U008043<br>5 | 7TGGGGAATATTGCACAATGGGGGAAACCCTGATGCAG<br>CGACGCCGCGTGGAGGAAGAAGGCCCTCGGGTTGTAA<br>ACTCCTGTCTTCGGGGACGATAATGACGGTACCCGAG<br>GAGGAAGCCACGGCTAACTACGTGCC |
| SEQ_ID_NO_ 204 | R_U004438<br>2 | 7TGGGGGATATTGCACAATGGGGGGAACCCTGATGCAG<br>CGACGCCGCGTGAGCGAAGAAGATCTTCGGATTGTAA<br>AGCTCTGTCTTAGGGGACGATGATGACGGTACCCTGA<br>GAGGAAGCCACGGCTAACTACGTGCC |
| SEQ_ID_NO_ 205 | R_U000001<br>8 | 2TGGGGGATATTGCGCAATGGGGGCAACCCTGACGCAG<br>CAACGCCGCGTGAAGGATGAAGGTTTTCGGATTGTAA<br>ACTTCTTTTCTTAAGGACGAAATTTGACGGTACTTAAG<br>GAATAAGCTCCGGCTAACTACGTGCC |
| SEQ_ID_NO_ 206 | R_U000027<br>7 | 7TGGGAATATTGGGCAATGGGCGCAAGCCTGACCCAG<br>CAACGCCGCGTGAAGGAAGAAGGCTTTCGGGTTGTAA<br>ACTTCTTTTAAGAGGGACGAAGGAAGTGACGGTACCT<br>CTTGAATAAGCCACGGCTAACTACGTGCC |
| SEQ_ID_NO_ 207 | R_U000011<br>6 | 6TGAGGGATATTGGTCAATGGGGGAAACCCTGAACCAG<br>CAACGCCGCGTGAGGGAAGACGGTCTTCGGATTGTAA<br>ACCTTTGTCCTCTGTGAAGATAATGACGGTAGCAGAG<br>GAGGAAGCTCCGGCTAACTACGTGCC |
| SEQ_ID_NO_ 208 | R_U000020<br>7 | 8TGGGGGATATTGCACAATGGGGGAAACCCTGATGCAG<br>CAACGCCGCGTGAAGGAAGAAGGTCTTCGGATTGTAA<br>ACTTTTGTCCTTGGTGAAGATAATGACGGTAGCCAAG<br>GAGGAAGCTCCGGCTAACTACGTGCC |
| SEQ_ID_NO_ 209 | R_U000080<br>8 | 9TGGGGAATATTGGGCAATGGGCGCAAGCCTGACCCAG<br>CAACGCCGCGTGAAGGAAGAAGGCTTTCGGGTTGTAA<br>ACTTCTTTTGTCAGGGAAGAGCAGAAGACGGTACCTG<br>ACGAATAAGCCACGGCTAACTACGTGCC |
| SEQ_ID_NO_ 210 | R_U000009<br>1 | 8TGGGGGATATTGCACAATGGGGGAAACCCTGATGCAG<br>CGACGCCGCGTGTGGGAAGACGGTCCTCTGGATTGTA<br>AACCACTGTCCCCAGGGACGAAGATGACGGTACCTGG<br>GGAGGAAGCTCCGGCTAACTACGTGCC |

TABLE 2-continued 16S rRNA gene V3 region sequence of those bacteria suppressed/eliminated by berberine.

| List | OTUName | 16S rRNA Gene V3 Region Sequence |
|---|---|---|
| SEQ_ID_NO_ 211 | R_U0043629 2 | TGGGGAATATTGCACAATGGGGGAACCCTGATGCAG CGATGCCGCGTGGAGGAAGAAGGTTTTCGGATTGTAA ACTCCTGTCGACAGGAAAGAAAAAGGACTGTACCTGT CAAGAAAGCTCCGGCTAACTACGTGCC |
| SEQ_ID_NO_ 212 | R_U0000255 1 | TGGGGAATATTGCACAATGGGGGAACCCTGATGCAG CGATGCCGCGTGGAGGAAGAAGGTTTTCGGATTGTAA ACTCCTGTCTTAAAGGACGATAATGACGGTACTTTAG GAGGAAGCTCCGGCTAACTACGTGCC |
| SEQ_ID_NO_ 213 | R_U0016429 7 | TGGGGAATATTGCACAATGGAGGAAACTCTGATGCAG CGATGCCGCGTGAGGGAAGAAGGTTTTCGGATTGTAA ACCTCTGTCTTAAGGGACGATAATGACGGTACCTTAG GAGGAAGCTCCGGCTAACTACGTGCC |
| SEQ_ID_NO_ 214 | R_U0080693 7 | TGGGGGATATTGCACAATGGAGGGAACTCTGATGCAG CGATGCCGCGTGAGGGAAGAAGGTTTTCGGATTGTAA ACCTCTGTGGACAGAGACGATAATGACGGTATCTGTC AAGGAAGCCACGGCTAACTACGTGCC |
| SEQ_ID_NO_ 215 | R_U0000272 3 | TGGGGGATATTGCACAATGGGGGAAACCCTGATGCAG CGATGCCGCGTGAGGGAAGAAGGTTTTCGGATTGTAA ACCTCTGTGGAGGGGACGATAATGACGGTACCCCTT AAGGAAGCCACGGCTAACTACGTGCC |
| SEQ_ID_NO_ 216 | R_U0000487 8 | TGGGGGATATTGGACAATGGGGGAAACCCTTATCCAG CGACGCCGCGTGAGGGAAGAAGGTTTTCGGATTGTAA ACCTCTGTCAGCGGGGACGATAATGACGGTACCCGCG GAGGAAGCCACGGCTAACTACGTGCC |
| SEQ_ID_NO_ 217 | R_U0114298 2 | TGGGGAATATTGGGCAATGGGCGAAAGCCTGACCCAG CGACGCCGCGTGAAGGAAGACGGTCTTCGGATTGTAA ACTTTAGTACTCAGGGACGAAGAAATGACGGTACCTG AGGTTAAGCCACGGCTAACTACGTGCC |
| SEQ_ID_NO_ 218 | R_U0080688 4 | TGGGGGATATTGCGCAATGGGGGAAACCCTGACGCAG CAACGCCGCGTGAAGGAAGAAGGTTTTCGGATTGTAA ACTTCTTTTATTAAGGACGAAAGATGACGGTACTTAAT GAATAAGCTCCGGCTAACTACGTGCC |
| SEQ_ID_NO_ 219 | R_U0081053 1 | TGGGGAATATTGGGCAATGGACGCAAGTCTGACCCAG CAACGCCGCGTGAAGGAAGAAGGCTTTCGGGTTGTAA ACTTCTTTTGTCAGGGAAGAGAAGAAGACGGTACCTG ACGAACAAGCCACGGCTAACTACGTGCC |
| SEQ_ID_NO_ 220 | R_U0000014 9 | TGGGGAATATTGGGCAATGGGCGCAAGCCTGACCCAG CAACGCCGCGTGAAGGAAGAAGGCTTTCGGGTTGTAA ACTTCTTTTGACAGGGAAGAGCAGAAGACGGTACCTG TCGAATAAGCCACGGCTAACTACGTGCC |
| SEQ_ID_NO_ 221 | R_U0000450 1 | TGGGGGATATTGCGCAATGGGGGCAACCCTGACGCAG CAACGCCGCGTGAAGGATGAAGGTTTTCGGATTGTAA ACTTCTTTTATTAAGGACGAATTTTGACGGTACTTAAT GAATAAGCTCCGGCTAACTACGTGCC |
| SEQ_ID_NO_ 222 | R_U0013288 2 | TGGGGAATATTGGGCAATGGGCGCAAGCCTGACCCAG CAACGCCGCGTGAAGGAAGAAGGCTTTCGGGTTGTAA ACTTCTTTTAAGAGGGAAGAGCAGAAGACGGTACCTC TTGAATAAGCTCCGGCTAACTACGTGCC |
| SEQ_ID_NO_ 223 | R_U0080038 7 | TGGGGAATATTGGGCAATGGGGGAAACCCTGACCCAG CAACGCCGCGTGAGGGAAGAAGGCTTTCGGGTTGTAA ACCTCTTTTACCAGGGACGAAGGACGTGACGGTACCT GGAGAAAAGCAACGGCTAACTACGTGCC |
| SEQ_ID_NO_ 224 | R_U0000090 8 | TGGGGAATATTGGGCAATGGGGGAAACCCTGACCCAG CAACGCCGCGTGAAGGAAGAAGGCCTTCGGGTTGTAA ACTTCTTTTACCAGGGACGAAGGACGTGACGGTACCT GGAGAAAAGCAACGGCTAACTACGTGCC |
| SEQ_ID_NO_ 225 | R_U0020438 6 | TGGGGAATATTGGGCAATGGGCGAAAGCCTGACCCAG CAACGCCGCGTGAAGGAAGAAGGCCTTCGGGTTGTAA ACTTCTTTTAAGAGGGACGAAGAAAGTGACGGTACCT CTTGAATAAGCCACGGCTAACTACGTGCC |

TABLE 2-continued 16S rRNA gene V3 region sequence of those bacteria suppressed/eliminated by berberine.

| List | OTUName | 16S rRNA Gene V3 Region Sequence |
|---|---|---|
| SEQ_ID_NO_ 226 | R_U0079945 3 | TGGGGAATATTGGGCAATGGGCGCAAGCCTGACCCAGCAACGCCGCGTGAAGGAAGAAGGCTTTCGGGTTGTAAACTTCTTTTGAGAGGGACGAAACAAATGACGGTACCTCTTGAATAAGCCACGGCTAACTACGTGCC |
| SEQ_ID_NO_ 227 | R_U0080607 1 | TGGGGAATATTGGGCAATGGGCGGAAGCCTGACCCAGCAACGCCGCGTGAAGGAAGAAGGCTTTCGGGTTGTAAACTTCTTTTCTTGGGGACGAAGAAAGTGACGGTACCCAAGGAATAAGCCACGGCTAACTACGTGCC |
| SEQ_ID_NO_ 228 | R_U0113290 7 | TGGGGAATATTGGGCAATGGGCGCAAGCCTGACCCAGCAACGCCGCGTGAAGGAAGAAGGCTTTCGGGTTGTAAACTTCTTTTGAGGGGACGAAGGATGTGACGGTACCCCTTGAATAAGCCACGGCTAACTACGTGCC |
| SEQ_ID_NO_ 229 | R_U0046333 7 | TGGGGAATATTGGGCAATGGGCGCAAGCCTGACCCAGCAACGCCGCGTGAAGGAAGAAGGCTTTCGGGTTGTAAACTTCTTTTCTTGGGGACGAAGAAAGTGACGGTACCCGAGGAATAAGCCACGGCTAACTACGTGCC |
| SEQ_ID_NO_ 230 | R_U0081299 4 | TGGGGAATATTGCACAATGGGGGAAACCCTGATGCAGCGACGCCGCGTGGGTGAAGAAGTATTTCGGTATGTAAAGCCCTATCAGCAGGGAAGATCATGACGGTACCTGACTAAGAAGCCCCGGCTAACTACGTGCC |
| SEQ_ID_NO_ 231 | R_U0001001 8 | TGGGGAATATTGGGCAATGGGCGCAAGCCTGACCCAGCAACGCCGCGTGAAGGAAGAAGGCTTTCGGGTTGTAAACTTCTTTTCTGAGGGACGAAGCAAGTGACGGTACCTTAGGAATAAGCCACGGCTAACTACGTGCC |
| SEQ_ID_NO_ 232 | R_U0016472 0 | TGGGGAATATTGGGCAATGGGCGCAAGCCTGACCCAGCAACGCCGCGTGAAGGAAGAAGGCTTTCGGGTTGTAAACTTCTTTTGACAGGGAAGAGGAGAAGACGGTACCTGTCGAATAAGCTCCGGCTAACTACGTGCC |
| SEQ_ID_NO_ 233 | R_U0000441 8 | TGGGGAATATTGGGCAATGGGCGCAAGCCTGACCCAGCAACGCCGCGTGAAGGAAGAAGGCCCTCGGGTTGTAAACTTCTTTTATCAGGGACGAAGAAGTGACGGTACCTGATGAATAAGCCACGGCTAACTACGTGCC |
| SEQ_ID_NO_ 234 | R_U0020815 3 | TGGGGAATATTGCGCAATGGGGGAAACCCTGACGCAGCAACGCCGCGTGATTGAAGAAGGCCTTCGGGTTGTAAAGATCTTTAATCGGGGACGAATTTTGACGGTACCCGAAGAATAAGCTCCGGCTAACTACGTGCC |
| SEQ_ID_NO_ 235 | R_U0003087 0 | TGGGGAATATTGCGCAATGGGGGAAACCCTGACGCAGCAACGCCGCGTGATTGAAGAAGGCCCTCGGGTTGTAAAGATCTTTAATCGGGGACGAAGAATGACGGTACCCGAAGAATAAGCTCCGGCTAACTACGTGCC |
| SEQ_ID_NO_ 236 | R_U0083779 7 | TGGGGAATATTGCGCAATGGGGGAAACCCTGACGCAGCAACGCCGCGTGAGTGAAGAAGGCCTTCGGGTTGTAAAGCTCTTTAATCAGGGACGAAGAACGACGGTACCTGAAGAATAAGCTCCGGCTAACTACGTGCC |
| SEQ_ID_NO_ 237 | R_U0044980 4 | TGGGGAATATTGGGCAATGGGCGAAAGCCTGACCCAGCAACGCCGCGTGAAGGAAGAAGGTCTTCGGATTGTAAACTTCTTTTATCAGGGACGAAGGAAGTGACGGTACCTGATGAATAAGCCACGGCTAACTACGTGCC |
| SEQ_ID_NO_ 238 | R_U0043633 2 | TCGGGAATATTGCGCAATGGAGGCAACTCTGACGCAGTGACGCCGCGTATAGGAAGAAGGTTTTCGGATTGTAAACTATTGTCCACAGGGAAGAAAAGGACTGTACCTGTGAAGAAAGCTCCGGCTAACTACGTGCC |
| SEQ_ID_NO_ 239 | R_U0000343 5 | TCGGGAATATTGCGCAATGGAGGAAACTCTGACGCAGTGACGCCGCGTATAGGAAGAAGGTTTTCGGATTGTAAACTATTGTCCACAGGGAAGATAAAAGACTGTACCTGTGAAGAAAGCTCCGGCTAACTACGTGCC |
| SEQ_ID_NO_ 240 | R_U0019867 3 | TCGGGAATATTGCGCAATGGAGGAAACTCTGACGCAGTGACGCCGCGTATAGGAAGAAGGTTTTCGGATTGTAAACTATTGTCGATAGGGAAGAAAAAAGACTGTACCTATCAAGAAAGCTCCGGCTAACTACGTGCC |

TABLE 2-continued 16S rRNA gene V3 region sequence of those bacteria suppressed/eliminated by berberine.

| List | OTUName | 16S rRNA Gene V3 Region Sequence |
|---|---|---|
| SEQ_ID_NO_ 241 | R_U00002720 | TCGGGAATATTGCGCAATGGAGGGAACTCTGACGCAG<br>TGACGCCGCGTATAGGAAGAAGGTTTTCGGATTGTAA<br>ACTATTTTAGTCAGGGAAGAAAGCAGACGGTACCTGA<br>AGAATAAGCTCCGGCTAACTACGTGCC |
| SEQ_ID_NO_ 242 | R_U0019570_7 | TCGGGAATATTGCACAATGGAGGAAACTCTGATGCAG<br>TGACGCCGCGTGCAGGAAGAAGGTTTTCGGATTGTAA<br>ACTGCTTTAGACAGGGAAGAAAAAAGACAGTACCTGT<br>AGAATAAGCTCCGGCTAACTACGTGCC |
| SEQ_ID_NO_ 243 | R_U0000268_6 | TCGGGAATATTGCGCAATGGAGGAAACTCTGACGCAG<br>TGACGCCGCGTATAGGAAGAAGTTTTTCGGAATGTAA<br>ACTATTGTCGTTAGGGAAGAGAAAGGACAGTACCTAA<br>GGAGGAAGCTCCGGCTAACTACGTGCC |
| SEQ_ID_NO_ 244 | R_U0000895_9 | TCGGGAATATTGCGCAATGGAGGGAACTCTGACGCAG<br>TGACGCCGCGTATAGGAAGAAGGTTTTCGGATTGTAA<br>ACTATTGTCGTTAGGGAAGAAAAAAGACAGTACCTAA<br>GGAGGAAGCCCCGGCTAACTATGTGCC |
| SEQ_ID_NO_ 245 | R_U0003435_1 | TCGGGAATATTGCGCAATGGAGGAAACTCTGACGCAG<br>TGACGCCGCGTATAGGAAGAAGGTCTTCGGATTGTAA<br>ACTATTGTCGTTAGGGAAGAGAAAGGACAGTACCTAA<br>GGAGGAAGCTCCGGCTAACTACGTGCC |
| SEQ_ID_NO_ 246 | R_U0043700_9 | TCGGGAATATTGCGCAATGGAGGAAACTCTGACGCAG<br>TGACGCCGCGTGCAGGAAGAAGGTTTTCGGATTGTAA<br>ACTGCTTTAGACAGGGAAGAAACAAATGACAGTACCT<br>GTAGAATAAGCTCCGGCTAACTACGTGCC |
| SEQ_ID_NO_ 247 | R_U0003248_6 | TCGGGAATATTGCGCAATGGAGGAAACTCTGACGCAG<br>TGACGCCGCGTATAGGAAGAAGGTTTTCGGATTGTAA<br>ACTATTGTCGTGAGGGAAGAAATTGACAGTACCTCAG<br>GAGGAAGCTCCGGCTAACTATGTGCC |
| SEQ_ID_NO_ 248 | R_U0000099_9 | TCGGGAATATTGCGCAATGGAGGAAACTCTGACGCAG<br>TGACGCCGCGTATAGGAAGAAGGTTTTCGGATTGTAA<br>ACTATTGTCGTTAGGGAAGAGAAAGGACAGTACCTAA<br>GGAGGAAGCTCCGGCTAACTACGTGCC |
| SEQ_ID_NO_ 249 | R_U0000220_1 | TCGGGAATATTGCGCAATGGAGGAAACTCTGACGCAG<br>TGACGCCGCGTGCAGGAAGAAGGTTTTCGGATTGTAA<br>ACTGCTTTAGACAGGGAAGAAAGAAATGACGGTACCT<br>GTAGAATAAGCTCCGGCTAACTACGTGCC |
| SEQ_ID_NO_ 250 | R_U0000189_1 | TCGGGAATATTGCGCAATGGAGGAAACTCTGACGCAG<br>TGACGCCGCGTATAGGAAGAAGGTTTTCGGATTGTAA<br>ACTATTGTCGTTAGGGAAGATAAAAGACTGTACCTAA<br>GGAGGAAGCCCCGGCTAACTATGTGCC |
| SEQ_ID_NO_ 251 | R_U0080366_5 | TCGGGAATATTGCGCAATGGAGGAAACTCTGACGCAG<br>TGACGCCGCGTATAGGAAGAAGTTTTTCGGAATGTAA<br>ACTATTGTCATTAGGGAAGAGAAAGGACGGTACCTAA<br>GGAGGAAGCCCCGGCTAACTATGTGCC |
| SEQ_ID_NO_ 252 | R_U0002711_1 | TCGGGAATATTGCGCAATGGAGGAAACTCTGACGCAG<br>TGACGCCGCGTATAGGAAGAAGGTTTTCGGATTGTAA<br>ACTATTGTCGTTAGGGAAGAAAAAAGACAGTACCTAA<br>GGAGGAAGCCCCGGCTAACTATGTGCC |
| SEQ_ID_NO_ 253 | R_U0045415_7 | TTGGGAATATTGGACAATGGAGGAAACTCTGATCCAG<br>TGACGCCGCGTGAAGGAAGAAGGTCTTCGGATTGTAA<br>ACTTATTTTGTCAGGGAAGAATAAATGACTGTACCTG<br>AAGAAAAAGCACCGGCTAACTACGTGCC |
| SEQ_ID_NO_ 254 | R_U0008017_4 | TGGGGAATATTGCGCAATGGGGGAAACCCTGACGCAG<br>CAACGCCGCGTGCAGGAAGAAGGTCTTCGGATTGTAA<br>ACTGTTGTCGCAGGGGAAGAAGACAGTGACGGTACCC<br>TGTGAGAAAGTCACGGCTAACTACGTGCC |
| SEQ_ID_NO_ 255 | R_U0080330_2 | TGGGGAATATTGGGCAATGGGCGAAAGCCTGACCCAG<br>CAACGCCGCGTGGAGGAAGAAGGTTTTCGGATCGTAA<br>ACTCCTGTCCTAAGAGACGAGGAAGAGACGGTATCTT<br>AGGAGGAAGCCCCGGCTAACTACGTGCC |

TABLE 2-continued 16S rRNA gene V3 region sequence of those bacteria suppressed/eliminated by berberine.

| List | OTUName | 16S rRNA Gene V3 Region Sequence |
|---|---|---|
| SEQ_ID_NO_<br>256 | R_U0003220<br>8 | TGGGGAATATTGGGCAATGGGCGAAAGCCTGACCCAG<br>CAACGCCGCGTGAGGGAAGAAGGTTTTCGGATTGTAA<br>ACCTCTGTCCTAAGTGACGAAGGAAGTGACGGTAGCT<br>TAGGAGGAAGCCCCGGCTAACTACGTGCC |
| SEQ_ID_NO_<br>257 | R_U0000111<br>6 | TGGGGAATATTGGGCAATGGGCGAAAGCCTTACCCAG<br>CAACGCCGCGTGAGGGAAGAAGGTTTTCGGATTGTAA<br>ACCTCTGTCCTGGGGGACGAAGGAAGTGACGGTACCC<br>CGGGAGGAAGCCCCGGCTAACTACGTGCC |
| SEQ_ID_NO_<br>258 | R_U0080770<br>4 | TGGGGAATATTGGGCAATGGGGGAAACCCTGACCCAG<br>CAACGCCGCGTGAAGGAAGAAGGTTTTCGGATCGTAA<br>ACTTCTATCCTTGGTGAAAATGATGATGGTAGCCAAG<br>AAGGAAGCCCCGGCTAACTACGTGCC |
| SEQ_ID_NO_<br>259 | R_U0000027<br>2 | TGGGGAATATTGGGCAATGGGCGAAAGCCTGACCCAG<br>CAACGCCGCGTGAGGGAAGAAGGGTTTCGGCTCGTAA<br>ACCTCTGTCCTATGGGACGAAGGAAGTGACGGTACCA<br>TAGGAGGAAGCCCCGGCTAACTACGTGCC |
| SEQ_ID_NO_<br>260 | R_U0080527<br>7 | TGGGGAATATTGCACAATGGGCGAAAGCCTGATGCAG<br>CAACGCCGCGTGAGCGAAGAAGGTCTTCGGATCGTAA<br>AGCTCTGTCCTTGGGGAAGATAATGACGGTACCCAAG<br>GAGGAAGCCCCGGCTAACTACGTGCC |
| SEQ_ID_NO_<br>261 | R_U0113623<br>8 | TGGGGAATATTGGGCAATGGAGGCAACTCTGACCCAG<br>CAACGCCGCGTGAATGAAGAAGGTCCTAGGATTGTAA<br>AGTTCTTTTATGATAGACGAATAAAATGACGGTATAT<br>CATGAATAAGCCACGGCTAACTACGTGCC |
| SEQ_ID_NO_<br>262 | R_U0084863<br>9 | TGGGGAATATTGGGCAATGGAGGCAACTCTGACCCAG<br>CAACGCCGCGTGAATGAAGAAGGCCTTCGGGTTGTAA<br>AGTTCTTTAATGGGGGACGAAGAAAGTGACGGTACCC<br>CAAGAATAAGCCACGGCTAACTACGTGCC |
| SEQ_ID_NO_<br>263 | R_U0000424<br>9 | TGGGGGATATTGCACAATGGGGGAAACCCTGATGCAG<br>CGACGCCGCGTGAGTGAAGAAGTATTTCGGTATGTAA<br>AGCTCTATCAGCAGGGAAGAAAATGACGGTACCTGAC<br>TAAGAAGCCCCGGCTAACTACGTGCC |
| SEQ_ID_NO_<br>264 | R_U0001209<br>6 | TTAGGAATATTCGTCAATGGGGGAAACCCTGAACGAG<br>CAATGCCGCGTGAGTGATGACGGTCTTTATGATTGTA<br>AAACTCTGTTGTAAGGAAAGAACCCTTATCATAGGAA<br>ATGATGATAAGTTGACGGTACCTTACCAGAAAGCCCC<br>GGCTAACTACGTGCC |
| SEQ_ID_NO_<br>265 | R_U0115212<br>2 | TAGGGAATTTTCGGCAATGGGGGGAACCCTGACCGAG<br>CAACGCCGCGTGAACGAAGAAGTTATTCGTAATGTAA<br>AGTTCTTTTATCAGGGAAGAAAAGAAGGGAATTGACG<br>GTACCTGATGAATAAGCTCCGGCTAACTACGTGCC |
| SEQ_ID_NO_<br>266 | R_U0112319<br>9 | TGGGGAATCTTCCGCAATGGGCGAAAGCCTGACGGAG<br>CGACGCCGCGTGAGTGAAGAAGGTCTTCGGACCGTAA<br>AGCTCTTTTGTTGCAGGCGAAAGGACTTAAGAGGAAA<br>TGCTTAAGTTAAGACGGTATGGAACGAATAAGCCACG<br>GCTAACTACGTGCC |
| SEQ_ID_NO_<br>267 | R_U0000073<br>7 | TAGGGAATCTTTCACAATGGGCGAAAGCCTGATGGAG<br>CAACGCCGCGTGCAGGATGAAGGCCTTCGGGTTGTAA<br>ACTGCTTTTATAAGCGAGAAATATGATGGTAACTTAT<br>GAATAAGGATCGGCTAACTACGTGCC |
| SEQ_ID_NO_<br>268 | R_U0082204<br>0 | TGGGGAATTTTGGACAATGGACGGAAGTCTGATCCAG<br>CAACGCAGCGTGAAGGACGAAGGTTCTCGGATTGTAA<br>ACTTCTTTTGCAGGGGAAGAAAAAAATGACGGTACCC<br>TGTGAATAAGCCACGGCTAACTACGTGCC |

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, may be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A method for increasing a first gut microbiota population while simultaneously decreasing a second gut microbiota population in a subject having obesity, diabetes or insulin insensitivity to increase short-chain fatty acid level in the subject or reducing subject insulin sensitivity, comprising administering to the subject berberine at a dosage of from about 50 mg/Kg body weight to about 400 mg/Kg body weight, wherein the first gut microbiota population comprises, *Allobaculum, Bacteroides, Blautia, Butyricicoccus, Dorea, Holdemania, Lawsonia, Parabacteroides, Phascolarctobacterium, Sedimentibacter,* or a combination thereof; wherein the second gut microbiota population comprises *Anaeroplasma, Bifidobacterium, Butyrivibrio, Coprococcus, Fastidiosipila, Marvinbryantia, Oribacterium, Roseburia, Ruminococcus,* TM7_genera_incertae_sedis, or a combination thereof.

2. The method of claim 1, wherein the first gut microbiota population comprises a bacterium whose V3 region of 16S rRNA gene sequence has at least about 95% similarity with a nucleic acid sequence selected from a group consisting of SEQ ID NO: 1-93.

3. The method of claim 1, wherein the second gut microbiota population comprises a bacterium whose V3 region of 16S rRNA gene sequence has at least about 95% similarity with a nucleic acid sequence selected from a group consisting of SEQ ID NO: 94-268.

* * * * *

SEQUENCE LISTING

<160> NUMBER OF SEQ ID NOS: 268

<210> SEQ ID NO 1
<211> LENGTH: 137
<212> TYPE: DNA
<213> ORGANISM: Helicobacter

<400> SEQUENCE: 1
tagggaatat tgctcaatgg gggaaaccct gaagcagcaa cgccgcgtgg aggatgaagg    60
ttttcggatt gtaaactcct tttctaagag aagattatga cggtatctta ggaataagca   120
ccggctaact ccgtgcc                                                  137

<210> SEQ ID NO 2
<211> LENGTH: 116
<212> TYPE: DNA
<213> ORGANISM: Helicobacter

<400> SEQUENCE: 2
ggggaaaccc tgaagcagca acgccgcgtg gaggatgaag gtttcggatt gtaaactcct    60
ttctaagaga agattatgac ggtatcttag gaataagcac cggctaactc cgtgcc       116

<210> SEQ ID NO 3
<211> LENGTH: 163
<212> TYPE: DNA
<213> ORGANISM: Lawsonia

<400> SEQUENCE: 3
tggggaatat tgcgcaatgg gcgaaagcct gacgcagcga cgccgcgtga gggatgaagg    60
tcctcggatc gtaaacctct gtcagggggg aagaagcgcc tgtgagcaaa tagttcatgg   120
gtttgacggt accccaaag gaagcaccgg ctaactccgt gcc                      163

<210> SEQ ID NO 4
<211> LENGTH: 157
<212> TYPE: DNA
<213> ORGANISM: Bacteroides

<400> SEQUENCE: 4
tgaggaatat tggtcaatgg gcgcaggcct gaaccagcca gtagcgtga aggatgactg    60 ccctatgggt tgtaaacttc ttttatatgg gaataaagtt ttccacgtgt ggaattttgt   120
atgtgccata tgaataagga tcggctaact ccgtgcc                            157

<210> SEQ ID NO 5
<211> LENGTH: 157
<212> TYPE: DNA
<213> ORGANISM: Bacteroides

<400> SEQUENCE: 5
tgaggaatat tggtcaatgg acgagagtct gaaccagcca gtagcgtga aggatgactg    60 ccctatgggt tgtaaacttc ttttatatgg gaataaagtg agccacgtgt ggcttttttgt  120 atgtaccata cgaataagga tcggctaact ccgtgcc                            157

<210> SEQ ID NO 6
<211> LENGTH: 157
<212> TYPE: DNA
<213> ORGANISM: Bacteroides

<400> SEQUENCE: 6
tgaggaatat tggtcaatgg gcgcaggcct gaaccagcca gtagcgtga aggatgactg    60 ccctatgggt tgtaaacttc ttttatatgg gaataaagtt ttccacgtgt ggaattttgt   120
atgtaccata tgaataagga tcggctaact ccgtgcc                            157

<210> SEQ ID NO 7
<211> LENGTH: 159

```
<212> TYPE: DNA
<213> ORGANISM: Bacteroides

<400> SEQUENCE: 7
tgaggaatat tggtcaatgg gcgcaggcct gaaccagcca agtagcgtga aggatgactg      60
ccctatgggt tgtaaacttc ttttatatgg aataaagtt ttcctacgtg tggaattttg     120
ttatgtacca tatgaataag gatcggctaa ctccgtgcc                            159

<210> SEQ ID NO 8
<211> LENGTH: 158
<212> TYPE: DNA
<213> ORGANISM: Prevotella

<400> SEQUENCE: 8
tgaggaatat tggtcaatgg gcgcgagcct gaaccagcca agtagcgtgc aggacgacgg      60
ccctatgggt tgtaaactgt cttttatacg ggataaagt atgccacgtg tggtttattg     120
caggtaccgt atgaataagg accggctaat tccgtgcc                             158

<210> SEQ ID NO 9
<211> LENGTH: 157
<212> TYPE: DNA
<213> ORGANISM: Prevotella

<400> SEQUENCE: 9
tgaggaatat tggtcaatgg gcgcgagcct gaaccagcca agtagcgtgc aggacgacgg      60
ccctatgggt tgtaaactgc ttttatacgg gataaagta tgccacgtgt ggtttattgc     120
aggtaccgta tgaataagga ccggctaatt ccgtgcc                              157

<210> SEQ ID NO 10
<211> LENGTH: 161
<212> TYPE: DNA
<213> ORGANISM: Barnesiella

<400> SEQUENCE: 10
tgaggaatat tggtcaatgg gcggaagcct gaaccagcca agtcgcgtga gggaagacgg      60
ccctacgggt tgtaaacctc ttttgccggg gaggcaatgc ccacgctcgc gagctgggaa     120
ggagagtacc cggagaaaaa gacatcggct aactccgtgc c                         161

<210> SEQ ID NO 11
<211> LENGTH: 160
<212> TYPE: DNA
<213> ORGANISM: Barnesiella

<400> SEQUENCE: 11
tgaggaatat tggtcaatgg gcggaagcct gaaccagcca agtcgcgtga gggaagacgg      60
ccctacgggt tgtaaacctc ttttgccggg gagcaatgcc cacgctcgcg agctgggaag    120
gagagtaccc ggagaaaaag acatcggcta actccgtgcc                           160

<210> SEQ ID NO 12
<211> LENGTH: 160
<212> TYPE: DNA
<213> ORGANISM: Barnesiella

<400> SEQUENCE: 12
tgaggaatat tggtcaatgg gcggaagcct gaaccagcca agtcgcgtga gggaagacgg      60
ccctacgggt tgtaaacctc ttttgccggg gagcaaatgc ccagctcgcg agctgggaag    120
```

```
gagagtaccc ggagaaaaag catcggctaa actccgtgcc              160
```

<210> SEQ ID NO 13
<211> LENGTH: 158
<212> TYPE: DNA
<213> ORGANISM: Butyricimonas

<400> SEQUENCE: 13

```
tgaggaatat tggtcaatgg gcgagagcct gaaccagcca agtcgcgtga gggaagacgg    60
ccctacgggt tgtaaaccte tttttgtcagg gagcaagaac aggcacgtgt gcctgactga   120
gagtacctga agaaaaagac atcggctaac tccgtgcc                           158
```

<210> SEQ ID NO 14
<211> LENGTH: 158
<212> TYPE: DNA
<213> ORGANISM: Porphyromonadaceae

<400> SEQUENCE: 14

```
tgaggaatat tggtcaatgg ccggaaggct gaaccagcca agtcgcgtga gggactaagg    60
ccctacgggt cgtaaaccte tttgccggg gagcaatggg gcccttgcga gggcccaggg    120
agagtacccg gagaaaaagc atcggctaac tccgtgcc                           158
```

<210> SEQ ID NO 15
<211> LENGTH: 158
<212> TYPE: DNA
<213> ORGANISM: Barnesiella

<400> SEQUENCE: 15

```
tgaggaatat tggtcaatgg ccgggaggct gaaccagcca agtcgcgtga gggatgacgg    60
ccctacgggt tgtaaaccte tttttgtcggg gagcaaagga cttcacgagt ggagtttcga   120
gagtacccga agaaaaagac atcggctaac tccgtgcc                           158
```

<210> SEQ ID NO 16
<211> LENGTH: 157
<212> TYPE: DNA
<213> ORGANISM: Barnesiella

<400> SEQUENCE: 16

```
tgaggaatat tggtcaatgg ccgggaggct gaaccagcca agtcgcgtga gggatgacgg    60
ccctacgggt tgtaaaccte tttttgtcggg gagcaaagga cttcacgagt ggagtttcga   120
gagtacccga agaaaaagca tcggctaact ccgtgcc                            157
```

<210> SEQ ID NO 17
<211> LENGTH: 155
<212> TYPE: DNA
<213> ORGANISM: Porphyromonadaceae

<400> SEQUENCE: 17

```
tgaggaatat tggtcaatgg ccgggaggct gaaccagcca agtcgcgtga gggatgacgg    60
ccctacgggt tgtaaaccte tttgtcgggg agcaaaggac ttcacgagtg gagtttcgag   120
agtacccgaa gaaagacatc ggctaactcc gtgcc                              155
```

<210> SEQ ID NO 18
<211> LENGTH: 157
<212> TYPE: DNA
<213> ORGANISM: Butyricimonas

<400> SEQUENCE: 18

```
tgaggaatat tggtcaatgg gcgagagcct gaaccagcca agtcgcgtga gggaagacgg        60
ccctacgggt tgtaaacctc ttttgtcagg gagcaagaac aggcacgtgt gcctgactga      120
gagtacctga agaaaaagca tcggctaact ccgtgcc                               157
```

```
<210> SEQ ID NO 19
<211> LENGTH: 157
<212> TYPE: DNA
<213> ORGANISM: Barnesiella

<400> SEQUENCE: 19
tgaggaatat tggtcaatgg ccgagaggct gaaccagcca agtcgcgtga gggatgacgg        60
ccctacgggt tgtaaacctc ttttgtcggg gagcaaagga cttcacgtgt gaagtttcga      120
gagtacccga agaaaaagca tcggctaact ccgtgcc                               157
```

```
<210> SEQ ID NO 20
<211> LENGTH: 158
<212> TYPE: DNA
<213> ORGANISM: Porphyromonadaceae

<400> SEQUENCE: 20
tgaggaatat tggtcaatgg gcggaagcct gaaccagcca agtcgcgtga gggaagacgg        60
tcctatggat tgtaaacctc ttttgccggg gagcaatgcc gctcttgcga gagcggaggg      120
agagtacccg gagaaaaagc atcggctaac tccgtgcc                              158
```

```
<210> SEQ ID NO 21
<211> LENGTH: 158
<212> TYPE: DNA
<213> ORGANISM: Barnesiella

<400> SEQUENCE: 21
tgaggaatat tggtcaatgg ccggaaggct gaaccagcca agtcgcgtga gggaataagg        60
ccctacgggt cgtaaacctc ttttgtcagg gagcaaagct ggctacgcgt agccagaagg      120
agagtacctg aagaaaaagc atcggctaac tccgtgcc                              158
```

```
<210> SEQ ID NO 22
<211> LENGTH: 156
<212> TYPE: DNA
<213> ORGANISM: Porphyromonadaceae

<400> SEQUENCE: 22
tgaggaatat tggtcaatgg gcggaagcct gaaccagcca agtcgcgtga gggaagacgg        60
ccctacgggt tgtaaacctc tttgccggga gcaatgccca gctcgcgagc tgggaaggag      120
agtacccgga gaaaagacat cggctaactc cgtgcc                                156
```

```
<210> SEQ ID NO 23
<211> LENGTH: 157
<212> TYPE: DNA
<213> ORGANISM: Barnesiella

<400> SEQUENCE: 23
tgaggaatat tggtcaatgg gcggaagcct gaaccagcca agtcgcgtga gggaagacgg        60
ccctacgggt tgtaaacctc tttgccgggg agcaatgccc agctcgcgag ctgggaagga      120
gagtacccgg agaaaagaca tcggctaact ccgtgcc                               157
```

```
<210> SEQ ID NO 24
```

```
<211> LENGTH: 158
<212> TYPE: DNA
<213> ORGANISM: Porphyromonadaceae

<400> SEQUENCE: 24
tgaggaatat tggtcaatgg gcggaagcct gaaccagcca agtcgcgtga gggactaagg      60
ccctacgggt cgtaaacctc ttttgccggg gagcaagccg tcccacgtgt gggccggtgg     120
agagtacccg gagaaaaagc atcggctaac tccgtgcc                             158

<210> SEQ ID NO 25
<211> LENGTH: 159
<212> TYPE: DNA
<213> ORGANISM: Porphyromonadaceae

<400> SEQUENCE: 25
tgaggaatat tggtcaatgg gcggaagcct gaaccagcca agtcgcgtga gggactaagg      60
ccctacgggt cgtaaacctc ttttgccggg gagcaagccg tcccacgtgt gggccggtgg     120
agagtacccg gagaaaaaga catcggctaa ctccgtgcc                            159

<210> SEQ ID NO 26
<211> LENGTH: 158
<212> TYPE: DNA
<213> ORGANISM: Barnesiella

<400> SEQUENCE: 26
tgaggaatat tggtcaatgg gcggaagcct gaaccagcca agtcgcgtga gggaagacgg      60
ccctacgggt tgtaaacctc ttttgccggg gagcaatgcc cagctcgcga gctgggaagg    120
agagtacccg gagaaaaagc atcggctaac tccgtgcc                             158

<210> SEQ ID NO 27
<211> LENGTH: 161
<212> TYPE: DNA
<213> ORGANISM: Barnesiella

<400> SEQUENCE: 27
tgaggaatat tggtcaatgg gcggaagcct gaaccagcca agtcgcgtga gggaagacgg      60
ccctacgggt tgtaaacctc ttttttgccgg gggagcaatg cccagctcgc gagctgggaa    120
ggagagtacc ggagaaaaaa agcatcggct aactccgtgc c                         161

<210> SEQ ID NO 28
<211> LENGTH: 157
<212> TYPE: DNA
<213> ORGANISM: Parabacteroides

<400> SEQUENCE: 28
tgaggaatat tggtcaatgg gcgagagcct gaaccagcca agtcgcgtga aggatgaagg      60
atctatggtt tgtaaacttc ttttatatgg gaataaagtg aggaacgtgt tccttttttgt   120 atgtaccata tgaataagca tcggctaact ccgtgcc                              157

<210> SEQ ID NO 29
<211> LENGTH: 157
<212> TYPE: DNA
<213> ORGANISM: Bacteroides

<400> SEQUENCE: 29
tgaggaatat tggtcaatgg acgagagtct gaaccagcca agtagcgtga aggatgactg      60
ccctatgggt tgtaaacttc ttttatacgg gaataaagtg aggcacgtgt gcctttttgt    120
```

```
atgtaccgta tgaataagga tcggctaact ccgtgcc                                    157

<210> SEQ ID NO 30
<211> LENGTH: 158
<212> TYPE: DNA
<213> ORGANISM: Alistipes

<400> SEQUENCE: 30
tgaggaatat tggtcaatgg acgcaagtct gaaccagcca tgccgcgtgc aggaagacgg            60
ctctatgagt tgtaaactgt cttttgtact agggtaaacg ctcttacgtg taggagcctg          120
aaagtatagt acgaataagg atcggctaac tccgtgcc                                  158

<210> SEQ ID NO 31
<211> LENGTH: 157
<212> TYPE: DNA
<213> ORGANISM: Alistipes

<400> SEQUENCE: 31
tgaggaatat tggtcaatgg acgcaagtct gaaccagcca tgccgcgtgc aggaagacgg            60
ctctatgagt tgtaaactgc ttttgtacta gggtaaacgc ttctacgtgt aggagcctga          120
aagtatagta cgaataagga tcggctaact ccgtgcc                                   157

<210> SEQ ID NO 32
<211> LENGTH: 137
<212> TYPE: DNA
<213> ORGANISM: Coriobacteriaceae

<400> SEQUENCE: 32
tggggaattt tgcgcaatgg ggggaaccct gacgcagcaa cgccgcgtgc gggatgacgg            60
ccctcgggtt gtaaaccgct ttcagcaggg aagaccacga cggtacctgc agaagaagct          120
ccggctaact acgtgcc                                                         137

<210> SEQ ID NO 33
<211> LENGTH: 157
<212> TYPE: DNA
<213> ORGANISM: Flavobacteriaceae

<400> SEQUENCE: 33
tgaggaatat tgggcaatgg gcggaagcct gacccagcca tgccgcgtgc aggaagacag            60
ccctatgggt cgtaaactgc ttttttagag gaagaataaa gtctacgtgt agaccgatga          120
cggtacttta agaaaagca tcggctaact ccgtgcc                                    157

<210> SEQ ID NO 34
<211> LENGTH: 138
<212> TYPE: DNA
<213> ORGANISM: Blautia

<400> SEQUENCE: 34
gtagggaata ttgcacaatg ggggaaaccc tgatgcagcg acgccgcgtg aaggaagaag            60
tatctcggta tgtaaacttc tatcagcagg gaagacaatg acggtacctg actaagaagc          120
cccggctaac tacgtgcc                                                        138

<210> SEQ ID NO 35
<211> LENGTH: 137
<212> TYPE: DNA
<213> ORGANISM: Hespellia
```

```
<400> SEQUENCE: 35
tggggaatat tgcacaatgg gggaaaccct gatgcagcga cgccgcgtga aggaagaagt    60
atttcggtat gtaaacttct atcagcaggg aagaaagtga cagtacctga ctaagaagcc   120
ccggctaact acgtgcc                                                  137

<210> SEQ ID NO 36
<211> LENGTH: 140
<212> TYPE: DNA
<213> ORGANISM: Blautia

<400> SEQUENCE: 36
tggggaatat tgcacaatgg gggaaacccg tacgatgcag cgacgccgcg tgaaggaaga    60
agtatctcgg tatgtaaact tctatcagca gggaagataa tgacggtacc tgactaagaa   120
gccccggcta actacgtgcc                                               140

<210> SEQ ID NO 37
<211> LENGTH: 142
<212> TYPE: DNA
<213> ORGANISM: Clostridiales

<400> SEQUENCE: 37
tggggaatat tgcacaatgg gggaaacccg tacgatgcag cgacgccgcg tgaaggaaga    60
agtatctcgg tatgtaaact tactatcagc agggaagata atgacggtac ctgactaaga   120
agccccggcc taactacgtg cc                                            142

<210> SEQ ID NO 38
<211> LENGTH: 114
<212> TYPE: DNA
<213> ORGANISM: Blautia

<400> SEQUENCE: 38
aaaccctgat gcagcgacgc cgcgtgaagg aagaagtatc tcggtatgta aacttctatc    60
agcagggaag acaatgacgg tacctgacta gaacgcccg gctaactacg tgcc          114

<210> SEQ ID NO 39
<211> LENGTH: 137
<212> TYPE: DNA
<213> ORGANISM: Blautia

<400> SEQUENCE: 39
tggggaatat tgcacaatgg gggaaaccct gatgcagcga cgccgcgtga aggaagaagt    60
atctcggtat gtaaacttct atcagcaggg aagataatga cggtacctga ctaagaagcc   120
ccggctaatt acgtgcc                                                  137

<210> SEQ ID NO 40
<211> LENGTH: 137
<212> TYPE: DNA
<213> ORGANISM: Blautia

<400> SEQUENCE: 40
tggggaatat tgcacaatgg gggaaaccct gatgcagcga cgccgcgtga aggaagaagt    60
atctcggtat gtaaacttct atcagcaggg aagataatga cggtacctga ctaagaagcc   120
ccggctaact acgtgcc                                                  137

<210> SEQ ID NO 41
<211> LENGTH: 138
```

```
<212> TYPE: DNA
<213> ORGANISM: Clostridiales

<400> SEQUENCE: 41
tggggaatat tgcacaatgg gggaaaccct gatgcagcaa cgccgcgtgg gtgaaggagc    60
gtttcggcgc gtaaagccct gtcagcgggg aagaaaaaag acgtacccg accaagaagc    120 cccggctaac tacgtgcc                                                  138

<210> SEQ ID NO 42
<211> LENGTH: 137
<212> TYPE: DNA
<213> ORGANISM: Lachnospiraceae

<400> SEQUENCE: 42
tggggaatat tgcacaatgg gcgcaagcct gatgcagcga cgccgcgtga gtgaagaagt    60
atttcggtat gtaaagctct atcagcaggg aagaaaatga cggtacctga ctaagaagcc    120
ccggctaact acgtgcc                                                   137

<210> SEQ ID NO 43
<211> LENGTH: 137
<212> TYPE: DNA
<213> ORGANISM: Lachnospiraceae

<400> SEQUENCE: 43
tggggaatat tgcacaatgg gggaaaccct gatgcagcga cgccgcgtga aagatgaagt    60
atttcggtat gtaaacttct atcagcaggg aagaaaatga cggtacctga ctaagaagcc    120
ccggctaact acgtgcc                                                   137

<210> SEQ ID NO 44
<211> LENGTH: 137
<212> TYPE: DNA
<213> ORGANISM: Lachnospiraceae

<400> SEQUENCE: 44
tggggaatat tgcacaatgg aggaaactct gatgcagcga cgccgcgtga gtgaagaagt    60
atttcggtat gtaaagctct atcagcaggg aagacagtga cggtacctga ctaagaagct    120
ccggctaaat acgtgcc                                                   137

<210> SEQ ID NO 45
<211> LENGTH: 138
<212> TYPE: DNA
<213> ORGANISM: Lachnospiraceae

<400> SEQUENCE: 45
tggggaatat tgcacaatgg ggggaaccct gatgcagcga cgccgcgtga gtgacgaagt    60
atctcggtat gtaaagctct gtcagcaggg aagaagaatg acgtacctg aagaagaagc    120 accggctaaa tacgtgcc                                                  138

<210> SEQ ID NO 46
<211> LENGTH: 137
<212> TYPE: DNA
<213> ORGANISM: Lachnospiraceae

<400> SEQUENCE: 46
tggggaatat tgcacaatgg gcgaaagcct gatgcagcga cgccgcgtga gtgaagaagt    60
atttcggtat gtaaagctct atcagcaggg aagaaaatga cggtacctga ctaagaagcc    120
```

```
ccggctaact acgtgcc                                                    137
```

<210> SEQ ID NO 47
<211> LENGTH: 140
<212> TYPE: DNA
<213> ORGANISM: Clostridiales

<400> SEQUENCE: 47

```
tggggaatat tgcacaatgg gcgaaagcct gatgcagcaa cgccgcgtga aggaagacgg     60
ttttcggatt gtaaacttct atcaataggg aagaagaaa tgacggtacc taaataagaa    120
gccccggcta actacgtgcc                                               140
```

<210> SEQ ID NO 48
<211> LENGTH: 140
<212> TYPE: DNA
<213> ORGANISM: Clostridiales

<400> SEQUENCE: 48

```
tggggaatat tgcacaatgg gggaaaccct gatgcagcaa cgccgcgtga aggaagacgg     60
ttttcggatt gtaaacttct atcaataggg aagaaagaaa tgacggtacc taaataagaa   120
gccccggcta actacgtgcc                                               140
```

<210> SEQ ID NO 49
<211> LENGTH: 137
<212> TYPE: DNA
<213> ORGANISM: Clostridiales

<400> SEQUENCE: 49

```
tggggaatat tgcacaatgg gggaaaccct gatgcagcga cgccgcgtgg aggaagaagg     60
tcttcggatt gtaaactcct gtcccagggg acgataatga cggtaccctg ggaggaagca   120
ccggctaact acgtgcc                                                  137
```

<210> SEQ ID NO 50
<211> LENGTH: 138
<212> TYPE: DNA
<213> ORGANISM: clostridiales

<400> SEQUENCE: 50

```
tggggaatat tgcacaatgg gcgcaagcct gatgcagcaa cgccgcgtga aggaagacgg     60
ttttcggatt gtaaacttct gttcttagtg aagaagaatg acggtagcta aggagcaagc   120
cacggctaac tacgtgcc                                                 138
```

<210> SEQ ID NO 51
<211> LENGTH: 138
<212> TYPE: DNA
<213> ORGANISM: Clostridiales

<400> SEQUENCE: 51

```
tggggaatat tgcacaatgg gcgcaagcct gatgcagcaa cgccgcgtga aggaagacgg     60
ttttcggatt gtaaacttct gttcttagtg aagaataatg acgtaacta aggagcaagc   120
cacggctaac tacgtgcc                                                 138
```

<210> SEQ ID NO 52
<211> LENGTH: 137
<212> TYPE: DNA
<213> ORGANISM: Sedimentibacter

<400> SEQUENCE: 52

```
tggggaatat tgcacaatgg gggaaaccct gatgcagcga cgccgagtga gggaagaagg      60
ttttcggatt gtaaacctct gtccttggtg aagataatga cggtagccaa ggaggaagct    120
acggctaact acgtgcc                                                   137
```

<210> SEQ ID NO 53
<211> LENGTH: 140
<212> TYPE: DNA
<213> ORGANISM: Clostridiales

<400> SEQUENCE: 53

```
tggggggatat tgcacaatgg gggaaaccct gatgcagcga cgccgcgtga gggaagacgg     60
ccttcgggtt gtaaacctct gtcgcagggg acgaaggaag tgacggtacc ctgtgaggaa    120
gccacggcta actacgtgcc                                                140
```

<210> SEQ ID NO 54
<211> LENGTH: 136
<212> TYPE: DNA
<213> ORGANISM: Ruminococcaceae

<400> SEQUENCE: 54

```
gaatattgcg caatggggc aaccctgacg cagcaacgcc gcgtgaagga tgaaggtttt      60
cggattgtaa acttctttta tcaaggacga aggacgtgac ggtacttgat gaataagcca    120
cggctaacta cgtgcc                                                    136
```

<210> SEQ ID NO 55
<211> LENGTH: 141
<212> TYPE: DNA
<213> ORGANISM: Ruminococcaceae

<400> SEQUENCE: 55

```
tggggaatat tgggcaatgg gggaaaccct gacccagcaa cgccgcgtga aggaagaagg     60
ctttcgggtt gtaaacttct tttaccaggg gacgaaggac gtgacggtac ctggagaaaa    120
agcaacggct aactacgtgc c                                              141
```

<210> SEQ ID NO 56
<211> LENGTH: 141
<212> TYPE: DNA
<213> ORGANISM: Ruminococcaceae

<400> SEQUENCE: 56

```
tggggaatat tgggcaatgg gggaaaccct gacccagcaa cgccgcgtga aggaagaagg     60
ctttcgggtt gtaaacttct ttacctaggg acgaaggacg tgacggtacc tggagaaaaa    120
gacaacggct aactacgtgc c                                              141
```

<210> SEQ ID NO 57
<211> LENGTH: 140
<212> TYPE: DNA
<213> ORGANISM: Ruminococcaceae

<400> SEQUENCE: 57

```
tggggaatat tgggcaatgg gggaaaccct gacccagcaa cgccgcgtga aggaagaagg     60
ttttcgggtt gtaaacttct tttaccaggg acgaaggacg tgacggtacc tggagaaaaa    120
gcaacggcta actacgtgcc                                                140
```

<210> SEQ ID NO 58

```
<211> LENGTH: 114
<212> TYPE: DNA
<213> ORGANISM: Clostridiales

<400> SEQUENCE: 58
gacccagcaa cgccgcgtga aggaagaagg tcgtttcggg ttagtaaact tcttttaccg     60
agggacgaag gacgtgacgg tacctggaga aaaagcaacg gctaactacg tgcc          114

<210> SEQ ID NO 59
<211> LENGTH: 140
<212> TYPE: DNA
<213> ORGANISM: Ruminococcaceae

<400> SEQUENCE: 59
tggggaatat tgggcaatgg gggaaaccct gacccagcaa cgccgcgtga aggaagaagg     60
ctttcgggtt gtaaacttct tttaccaggg acgaaggacg tgacggtacc tggagaaaaa    120
gcaacggcta actacgtgcc                                                140

<210> SEQ ID NO 60
<211> LENGTH: 142
<212> TYPE: DNA
<213> ORGANISM: Ruminococcaceae

<400> SEQUENCE: 60
tggggaatat tgggcaatgg gggaaaccct gacccagcaa cgccgcgtga aggaagaagg     60
ctttcgggtt gtaaacttct tttacctagg gacgaaggac gtgacggtac ctggagaaaa    120
agacaacggc taactacgtg cc                                             142

<210> SEQ ID NO 61
<211> LENGTH: 140
<212> TYPE: DNA
<213> ORGANISM: Ruminococcaceae

<400> SEQUENCE: 61
tggggaatat tgggcaatgg gggaaaccct gacccagcaa cgccgcgtga aggaagaagg     60
ctttcgggtt gtaaacttct tttaccaggg acgaaggacg tgacggtacc tggagaaaag    120
acaacggcta actacgtgcc                                                140

<210> SEQ ID NO 62
<211> LENGTH: 141
<212> TYPE: DNA
<213> ORGANISM: Oscillibacter

<400> SEQUENCE: 62
tggggaatat tgggcaatgg gcgcaagcct gacccagcaa cgccgcgtga aggaagaagg     60
ctttcgggtt gtaaacttct tttctggggg acgaagaaag tgacggtacc ccacggaata    120
agccacggct aactacgtgc c                                              141

<210> SEQ ID NO 63
<211> LENGTH: 140
<212> TYPE: DNA
<213> ORGANISM: Ruminococcaceae

<400> SEQUENCE: 63
tggggaatat tgggcaatgg gcgcaagcct gacccagcaa cgccgcgtga aggaagaagg     60
ctttcgggtt gtaaacttct tttctggggg cgaagaaag tgacggtacc ccaggaataa     120
gccacggcta actacgtgcc                                                140
```

<210> SEQ ID NO 64
<211> LENGTH: 140
<212> TYPE: DNA
<213> ORGANISM: Oscillibacter

<400> SEQUENCE: 64

```
tggggaatat tgggcaatgg gcgcaagcct gacccagcaa cgccgcgtga aggaagaagg    60
ctttcgggtt gtaaacttct tttctggggg acgaagaaag tgacggtacc ccaggaataa   120
gccacggcta actacgtgcc                                               140
```

<210> SEQ ID NO 65
<211> LENGTH: 139
<212> TYPE: DNA
<213> ORGANISM: Ruminococcaceae

<400> SEQUENCE: 65

```
tggggaatat tgggcaatgg gcgcaagcct gacccagcaa cgccgcgtga aggaagaagg    60
ctttcgggtt gtaaacttct tttctcgggg acgaacaaat gacggtaccc gaggaataag   120
ccacggctaa ctacgtgcc                                                139
```

<210> SEQ ID NO 66
<211> LENGTH: 139
<212> TYPE: DNA
<213> ORGANISM: Butyricicoccus

<400> SEQUENCE: 66

```
tggggaatat tgcgcaatgg gggcaaccct gacgcagcaa cgccgcgtga ttgaagaagg    60
tcttcggatt gtaaaaatct tttatcaagg acgaagaagt gacggtactt gatgaataag   120
ctccggctaa ctacgtgcc                                                139
```

<210> SEQ ID NO 67
<211> LENGTH: 139
<212> TYPE: DNA
<213> ORGANISM: bacterium

<400> SEQUENCE: 67

```
tggggaatat tgggcaatgg ggggaaccct gacccagcaa cgccgcgtga gggaagaagg    60
ttttcggatc gtaaacctct gtccttggtg aagaggagaa gacggtagcc aaggaggaag   120
ccccggctaa ctacgtgcc                                                139
```

<210> SEQ ID NO 68
<211> LENGTH: 139
<212> TYPE: DNA
<213> ORGANISM: bacterium

<400> SEQUENCE: 68

```
tggggaatat tgggcaatgg gggaaaccct gacccagcaa cgccgcgtga gggaagaagg    60
ttttcggatc gtaaacctct gtccttggtg aagagaagaa gacggtagcc aaggaggaag   120
ccccggctaa ctacgtgcc                                                139
```

<210> SEQ ID NO 69
<211> LENGTH: 137
<212> TYPE: DNA
<213> ORGANISM: Dorea

<400> SEQUENCE: 69

```
tggggaatat tgcacaatgg gcgaaagcct gatgcagcaa cgccgcgtga aggatgaagt    60
atttcggtat gtaaacttct atcagcaggg aagataacga cggtacctga ctaagaagcc   120
ccggctaact acgtgcc                                                  137
```

<210> SEQ ID NO 70
<211> LENGTH: 140
<212> TYPE: DNA
<213> ORGANISM: Clostridiales
<400> SEQUENCE: 70

```
tggggaatat tgcacaatgg gcgcaagcct gatgcagcaa cgccgcgtga acgaagaagg    60
tcttcggatt gtaaagttct gtccttaggg aagaagaaag tgacggtacc taaggaggaa   120
gccccggcta actacgtgcc                                               140
```

<210> SEQ ID NO 71
<211> LENGTH: 109
<212> TYPE: DNA
<213> ORGANISM: Lachnospiraceae
<400> SEQUENCE: 71

```
tggggaatat tgcacaatgg gcgaaagcct gatgcagcga cgccgcgtga gtgaagaagt    60
atttcggtat gtaaagctct atcagcaggg aagaaaatga cggtacctg              109
```

<210> SEQ ID NO 72
<211> LENGTH: 137
<212> TYPE: DNA
<213> ORGANISM: Clostridiales
<400> SEQUENCE: 72

```
tggggaatat tgcacaatgg gggaaaccct gatgcagcga cgccgcgtga aggaagaagt    60
atttcggtat gtaaacttct atcagcaggg aagaaaatga cggtacctga ctaagaagcc   120
ccggctaatt acgtgcc                                                  137
```

<210> SEQ ID NO 73
<211> LENGTH: 163
<212> TYPE: DNA
<213> ORGANISM: Allobaculum
<400> SEQUENCE: 73

```
tagggaattt ttcgtcaatg ggcgcaagcc tgaacgagca atgccgcgtg ggcgaagaag    60
gtcttcggat cgtaaaactc tgttgcgggg gaaaaaggaa gggaagagga aatgcttttc   120
ttttgatggt acccgccag aaagtcacgg ctaactacgt gcc                     163
```

<210> SEQ ID NO 74
<211> LENGTH: 163
<212> TYPE: DNA
<213> ORGANISM: Allobaculum
<400> SEQUENCE: 74

```
tagggaattt ttcgtcaatg ggcgcaagcc tgaacgagca atgccgcgtg agcgaagaag    60
gtcttcggat cgtaaaactc tgttgcgggg gaaaaaggaa ggaaagagga aatgcttttc   120
ttttgatggt acccgccag aaagtcacgg ctaactacgt gcc                     163
```

<210> SEQ ID NO 75
<211> LENGTH: 164
<212> TYPE: DNA
<213> ORGANISM: Allobaculum

<400> SEQUENCE: 75
tagggaattt tcgtcaatgg gcgcaagcct gaacgagcaa tgccgcgtgg gcgaagaagg      60
tcttcggatc gtaaaaactc tgttgcgggg gaaaaaagga agggaagagg aaatgctttt     120
cttttgatgg taccccgcca gaaagtcacg gctaactacg tgcc                      164

<210> SEQ ID NO 76
<211> LENGTH: 164
<212> TYPE: DNA
<213> ORGANISM: Allobaculum

<400> SEQUENCE: 76
tagggaattt tcgtcaatgg gcgcaagcct gaacgagcaa tgccgcgtgg gcgaagaagg      60
tcttcggatc gtaaaactct gtttgcgggg ggaaaaagga agggaagagg aaatgctttt     120
cttttgatgg taccccgcca gaaagtcacg gctaactacg tgcc                      164

<210> SEQ ID NO 77
<211> LENGTH: 162
<212> TYPE: DNA
<213> ORGANISM: Allobaculum

<400> SEQUENCE: 77
tagggaattt tcgtcaatgg gcgcaagcct gaacgagcaa tgccgcgtgg gcgaagaagg      60
tcttcggatc gtaaaactct gttgcggggg aaaaaggaag ggaagaggaa atgcttttct     120
tttgatggta ccccgccaga agtcacggc taactacgtg cc                         162

<210> SEQ ID NO 78
<211> LENGTH: 161
<212> TYPE: DNA
<213> ORGANISM: Allobaculum

<400> SEQUENCE: 78
tagggaattt tcgtcaatgg gcgcaagcct gaacgagcaa tgccgcgtga gcgaagaagg      60
tcttcggatc gtaaaactct gttgcgggga aaaggaaggg aagaggaaat gcttttcttt     120
tgtatggtac cccgccagaa agtcacggct aactacgtgc c                         161

<210> SEQ ID NO 79
<211> LENGTH: 162
<212> TYPE: DNA
<213> ORGANISM: Allobaculum

<400> SEQUENCE: 79
tagggaattt tcgtcaatgg gcgcaagcct gaacgagcaa tgccgcgtgg gcgaagaagg      60
tcttcggatc gtaaaactct gttgcggggg aaaaggaagg gaagaggaaa tgcttttctt     120
ttgtatggta ccccgccaga agtcacggc taactacgtg cc                         162

<210> SEQ ID NO 80
<211> LENGTH: 161
<212> TYPE: DNA
<213> ORGANISM: Allobaculum

<400> SEQUENCE: 80
tagggaattt tcgtcaatgg gcgcaagcct gaacgagcaa tgccgcgtgg gcgaagaagg      60
tcttcggatc gtaaaactct gttgcggggg aaaaggaagg gaagaggaaa tgcttttctt     120
ttgatggtac cccgccagaa agtcacggct aactacgtgc c                         161

<210> SEQ ID NO 81
<211> LENGTH: 159
<212> TYPE: DNA
<213> ORGANISM: Allobaculum

<400> SEQUENCE: 81
ggtaattttc gtcaatgggc gcaagcctga acgagcaatg ccgcgtgggc gaagaaggtc    60
ttcggatacg taaactctgt tgcggggggaa aaggaaggg aagaggaaat gctttctttt   120
gatggtaccc cgccagaaag tcacggctaa ctacgtgcc                          159

<210> SEQ ID NO 82
<211> LENGTH: 163
<212> TYPE: DNA
<213> ORGANISM: Allobaculum

<400> SEQUENCE: 82
tagggaattt tcgtcaatgg gcgcaagcct gaacgagcaa tgccgcgtga gcgaagaagg    60
tcttcggatc gtaaaactct gttgcggggg aaaaaggaag ggaagaggaa atgcttttct   120
tttgatggta ccccgcccag aaagtcacgg ctaactacgt gcc                     163

<210> SEQ ID NO 83
<211> LENGTH: 163
<212> TYPE: DNA
<213> ORGANISM: Allobaculum

<400> SEQUENCE: 83
tagggaattt tcgtcaatgg gcgcaagcct gaacgagcaa tgccgcgtga gcgaagaagg    60
tcttcggatc gtaaaactct gttgcggggg aaaaaaggaa gggaagagga aatgcttttc   120
ttttgatggt accccgccag aaagtcacgg ctaactacgt gcc                     163

<210> SEQ ID NO 84
<211> LENGTH: 162
<212> TYPE: DNA
<213> ORGANISM: Allobaculum

<400> SEQUENCE: 84
tagggaattt tcgtcaatgg gcgcaagcct gaacgagcaa tgccgcgtga gcgaagaagg    60
tcttcggatc gtaaaactct gttgcggggg aaaaaggaag ggaagaggaa atgcttttct   120
tttgatggta ccccgccaga aagtcacggc taactacgtg cc                      162

<210> SEQ ID NO 85
<211> LENGTH: 163
<212> TYPE: DNA
<213> ORGANISM: Allobaculum

<400> SEQUENCE: 85
tagggaattt ttcgtcaatg ggcgcaagcc tgaacgagca atgccgcgtg aacgaggaag    60
gtcttcggat cgtaaagttc tgttgagagg gaaaaagggt caccagagga aatgctggtg   120
aagtgatatt acctttcgag gaagtcacgg ctaactacgt gcc                     163

<210> SEQ ID NO 86
<211> LENGTH: 162
<212> TYPE: DNA
<213> ORGANISM: Allobaculum

<400> SEQUENCE: 86
tagggaattt tcgtcaatgg gcgcaagcct gaacgagcaa tgccgcgtga acgaggaagg    60

```
tcttcggatc gtaaagttct gttgagaggg aaaaagggtc accagaggaa atgctggtga    120
agtgatatta cctttcgagg aagtcacggc taactacgtg cc                      162
```

<210> SEQ ID NO 87
<211> LENGTH: 160
<212> TYPE: DNA
<213> ORGANISM: Allobaculum

<400> SEQUENCE: 87

```
ggtaattttc gtcaatgggc gcaagcctga acgagcaatg ccgcgtgaac gaggaaggtc    60
ttcggatcgt aaagttctgt tgagagggaa aagggtcac cagaggaaat gctggtgaag    120
tgatattacc tttcgaggaa gtcacggcta actacgtgcc                         160
```

<210> SEQ ID NO 88
<211> LENGTH: 163
<212> TYPE: DNA
<213> ORGANISM: Allobaculum

<400> SEQUENCE: 88

```
tagggaattt tcgtcaatgg gcgcaagcct gaacgagcaa tgccgcgtga acgaggaagg    60
tcttcggatc gtaaagttct gttgagaggg aaaaagggt caccagagga aatgctggtg    120
aagtgatatt acctttcgag gaagtcacgg ctaactacgt gcc                     163
```

<210> SEQ ID NO 89
<211> LENGTH: 161
<212> TYPE: DNA
<213> ORGANISM: Allobaculum

<400> SEQUENCE: 89

```
tagggaattt tcgtcaatgg gcgcaagcct gaacgagcaa tgccgcgtga acgaggaagg    60
tcttcggatc gtaaagttct gttgagaggg aaaagggtca ccagaggaaa tgctggtgaa    120
gtgatattac ctttcgagga agtcacggct aactacgtgc c                       161
```

<210> SEQ ID NO 90
<211> LENGTH: 163
<212> TYPE: DNA
<213> ORGANISM: Allobaculum

<400> SEQUENCE: 90

```
tagggaattt tcgtcaagtg ggcgcaagcc tgaacgagca atgccgcgtg aacgaggaag    60
gtcttcggat acgtaaagtt ctgttgagag gaaaaagggt caccagagga aatgctggtg    120
aagtgatatt acctttcgag gaagtcacgg ctaactacgt gcc                     163
```

<210> SEQ ID NO 91
<211> LENGTH: 161
<212> TYPE: DNA
<213> ORGANISM: Allobaculum

<400> SEQUENCE: 91

```
tagggaattt tcgtcaatgg gcgcaagcct gaacgagcaa tgccgcgtga gcgaagaagg    60
tcttcggatc gtaaaactct gttgcggggg aaaaggaagg gaagaggaaa tgcttttctt    120
ttgatggtac cccgccagaa agtcacggct aactacgtgc c                       161
```

<210> SEQ ID NO 92
<211> LENGTH: 162
<212> TYPE: DNA

-continued

<213> ORGANISM: Holdemania

<400> SEQUENCE: 92
tagggaattt tcggcaatgg gcgaaagcct gaccgagcaa cgccgcgtga gtgaagaagg    60
ccttcgggtt gtaaagctct gttgtgaagg aagaacggct catagaggga atgctatggg   120
agtgacggta ctttaccaga aagccacggc taactacgtg cc                      162

<210> SEQ ID NO 93
<211> LENGTH: 163
<212> TYPE: DNA
<213> ORGANISM: Phascolarctobacterium

<400> SEQUENCE: 93
tggggaatct tccgcaatgg acgaaagtct gacggagcaa cgccgcgtga gtgatgaagg    60
atttcggtct gtaaagctct gttgtttatg acgaacgtgc agtgtgtgaa caatgcattg   120
caatgacggt agtaaacgag gaagccacgg ctaactacgt gcc                     163

<210> SEQ ID NO 94
<211> LENGTH: 137
<212> TYPE: DNA
<213> ORGANISM: Alphaaproteobacteria

<400> SEQUENCE: 94
tgaggaatat tgggcaatgg gggcaaccct gacccagcca tgccgcgtga gtgaagaagg    60
ttttcggatt gtaaagctct ttcggatgtg acgatgatga cggtagcatc taaagaagcc   120
ccggcaaact tcgtgcc                                                  137

<210> SEQ ID NO 95
<211> LENGTH: 117
<212> TYPE: DNA
<213> ORGANISM: Helicobacter
<220> FEATURE:
<221> NAME/KEY: misc_feature
<222> LOCATION: 2..2
<223> OTHER INFORMATION: n is a, c, g, or t

<400> SEQUENCE: 95
gngggaaacc ctgaagcagc aacgccgcgt ggaggatgaa ggtttcggat tgtaaactcc    60
tttgttagag aagataatga cggtatctaa cgaataagca ccggctaact ccgtgcc      117

<210> SEQ ID NO 96
<211> LENGTH: 137
<212> TYPE: DNA
<213> ORGANISM: Helicobacter

<400> SEQUENCE: 96
tagggaatat tgctcaatgg gggaaaccct gaagcagcaa cgccgcgtgg aggatgaagg    60
ttttcggatt gtaaactcct tttgttagag aagataatga cggtatctaa cgaataagca   120
ccggctaact ccgtgcc                                                  137

<210> SEQ ID NO 97
<211> LENGTH: 157
<212> TYPE: DNA
<213> ORGANISM: Prevotella

<400> SEQUENCE: 97
tgaggaatat tggtcaatgg gcggaagcct gaaccagcca gtagcgtgc aggaagacgg    60 ccctacgggt tgtaaactgc ttttatgcgg ggataaagtg caatacgtgt attgctttgc   120

```
aggtaccgca tgaataagga ccggctaatt ccgtgcc                                      157

<210> SEQ ID NO 98
<211> LENGTH: 157
<212> TYPE: DNA
<213> ORGANISM: Prevotella

<400> SEQUENCE: 98
tgaggaatat tggtcaatgg gcggaagcct gaaccagcca agtagcgtgc aggatgacgg             60
ccctacgggt tgtaaactgc tttttttgcgg gaataaagcg gctcacgtgt gagcctttgc           120
atgtaccgca cgaataagga ccggctaatt ccgtgcc                                      157

<210> SEQ ID NO 99
<211> LENGTH: 157
<212> TYPE: DNA
<213> ORGANISM: Prevotella

<400> SEQUENCE: 99
tgaggaatat tggtcaatgg gcgagagcct gaaccagcca agtagcgtgc aggatgacgg             60
ccctatgggt tgtaaactgc ttttatacgg gataaagtt ggggacgtgt ccccatttgt            120
aggtaccgta tgaataagga ccggctaatt ccgtgcc                                      157

<210> SEQ ID NO 100
<211> LENGTH: 159
<212> TYPE: DNA
<213> ORGANISM: Prevotellaceae

<400> SEQUENCE: 100
tgaggaatat tggtcaatgg tcgtgagact gaaccagcca agtagcgtgc gggatgaagg             60
ccctccgggt cgtaaaccgc ttttagacgg ggataaaagg gcatacgtgt atgccgtatt           120
gcatgtaccg tcagaaaaag gaccggctaa ttccgtgcc                                    159

<210> SEQ ID NO 101
<211> LENGTH: 157
<212> TYPE: DNA
<213> ORGANISM: Bacteroidales

<400> SEQUENCE: 101
tgaggaatat tggtcaatgg gcgagagcct gaaccagcca agtagcgtga aggaagactg             60
ccctatgggt tgtaaacttc ttttataagg gaataaagag cgccacgtgt ggtgtgttgt            120 atgtaccttta tgaataagca tcggctaatt ccgtgcc                                     157

<210> SEQ ID NO 102
<211> LENGTH: 157
<212> TYPE: DNA
<213> ORGANISM: Bacteroidales

<400> SEQUENCE: 102
tgaggaatat tggtcaatgg gcgtgagcct gaaccagcca agccgcgtga gggaagaagg             60
cgccaggcgt cgtaaacctc ttttgccggg gaacaaaggg cgccacgtgt ggcgttgtga           120
gtgtacccgg agaaaaagca tcggctaact ccgtgcc                                      157

<210> SEQ ID NO 103
<211> LENGTH: 157
<212> TYPE: DNA
<213> ORGANISM: Bacteroidales
```

<400> SEQUENCE: 103
tgaggaatat tggtcaatgg gcgtgagcct gaaccagcca agccgcgtga gggaggaagg      60
cgccaggcgt cgtaaacctc ttttgccggg gaacaaaggg cgccacgtgt ggcgttgtga     120
gtgtacccgg agaaaagca tcggctaact ccgtgcc                               157

<210> SEQ ID NO 104
<211> LENGTH: 156
<212> TYPE: DNA
<213> ORGANISM: Bacteroidales

<400> SEQUENCE: 104
tgaggaatat tggtcaatgg gcgtgagcct gaaccagcca agccgcgtga gggaggaagg      60
cgccaggcgt cgtaaacctc ttttgccggg gaacaaaggg cgccacgtgt ggcgttgtga     120
gtgtacccgg agaaaagcat cggctaactc cgtgcc                               156

<210> SEQ ID NO 105
<211> LENGTH: 158
<212> TYPE: DNA
<213> ORGANISM: Bacteroidales

<400> SEQUENCE: 105
tgaggaatat tggtcaatgg gcgtgagcct gaaccagcca agccgcgtga gggaggaagg      60
cgccaggcgt cgtaaacctc ttttgccggg gaacaaaggg cgccacgtgt ggcgttgtga     120
gtgtacccgg agaaaaaagc atcggctaac tccgtgcc                             158

<210> SEQ ID NO 106
<211> LENGTH: 157
<212> TYPE: DNA
<213> ORGANISM: Butyricimonas

<400> SEQUENCE: 106
tgaggaatat tggtcaatgg gcgggagcct gaaccagcca agccgcgtga gggaataagg      60
cgccaagcgt cgtaaacctc ttttgtcagg gaacaaaagc gggcacgcgt gcccgtccga     120
gtgtacctga agaaaagca tcggctaact ccgtgcc                               157

<210> SEQ ID NO 107
<211> LENGTH: 158
<212> TYPE: DNA
<213> ORGANISM: Porphyromonadaceae

<400> SEQUENCE: 107
tgaggaatat tggtcaatgg gcgagagcct gaaccagcca agccgcgtga aggaagaagg      60
tgctaagcat tgtaaacttc ttttgtcagg gaacaaagag cgcgacgagt cgcgccgtga     120
gtgtacctga agaaaaagac atcggctaac tccgtgcc                             158

<210> SEQ ID NO 108
<211> LENGTH: 157
<212> TYPE: DNA
<213> ORGANISM: Porphyromonadaceae

<400> SEQUENCE: 108
tgaggaatat tggtcaatgg gcgagagcct gaaccagcca agccgcgtga aggaagaagg      60
tgctaagcat tgtaaacttc ttttgtcagg gaacaaagag cgcgacgagt cgcgccgtga     120
gtgtacctga agaaaagca tcggctaact ccgtgcc                               157

-continued

```
<210> SEQ ID NO 109
<211> LENGTH: 156
<212> TYPE: DNA
<213> ORGANISM: Porphyromonadaceae

<400> SEQUENCE: 109
tgaggaatat tggtcaatgg gcgagagcct gaaccagcca agccgcgtga aggaagaagg      60
tgctaagcat tgtaaacttc ttttgtcagg gaacaaagag cgcgacgagt cgcgccgtga     120
gtgtacctga agaaaagcat cggctaactc cgtgcc                              156

<210> SEQ ID NO 110
<211> LENGTH: 157
<212> TYPE: DNA
<213> ORGANISM: Porphyromonadaceae

<400> SEQUENCE: 110
tgaggaatat tggtcaatgg tcggaagact gaaccagcca agccgcgtga aggaagaagg      60
tgctcggcat cgtaaacttc ttttgtcagg gaacaaaggg cggtacgtgt accgctgtga     120
gtgtacctga agaaaagca tcggctaact ccgtgcc                              157

<210> SEQ ID NO 111
<211> LENGTH: 158
<212> TYPE: DNA
<213> ORGANISM: Porphyromonadaceae

<400> SEQUENCE: 111
tgaggaatat tggtcaatgg tcggaagact gaaccagcca agccgcgtga aggaagaagg      60
tgctcggcat cgtaaacttc ttttgtcagg gaacaaaggg cggtacgtgt accgctgtga     120
gtgtacctga agaaaaagc atcggctaac tccgtgcc                             158

<210> SEQ ID NO 112
<211> LENGTH: 157
<212> TYPE: DNA
<213> ORGANISM: Porphyromonadaceae

<400> SEQUENCE: 112
tgaggaatat tggtcaatgg gcgtgagcct gaaccagcca agccgcgtga aggaagaagg      60
tgcagggcat cgtaaacttc ttttgccggg gaacaataag cgggactagt cccgcgacga     120
gtgtacccgg agaaaagca tcggctaact ccgtgcc                              157

<210> SEQ ID NO 113
<211> LENGTH: 157
<212> TYPE: DNA
<213> ORGANISM: Porphyromonadaceae

<400> SEQUENCE: 113
tgaggaatat tggtcaatgg gcgtgagcct gaaccagcca agccgcgtga aggaagaagg      60
tgcagggcat cgtaaacttc ttttgccggg gaacaataag cgggactagt cccgcgacga     120
gtgtacccgg agaaaagaca tcggctaact ccgtgcc                             157

<210> SEQ ID NO 114
<211> LENGTH: 157
<212> TYPE: DNA
<213> ORGANISM: Porphyromonadaceae

<400> SEQUENCE: 114
tgaggaatat tggtcaatgg tcgggagact gaaccagcca agccgcgtga gggatggagg      60
```

```
tacagagtat cgtaaacctc ttttgtcagg gaacaaaggg cgccacgtgt ggcgctatga    120
gggtacctga agaaaaagca tcggctaact ccgtgcc                            157
```

<210> SEQ ID NO 115
<211> LENGTH: 157
<212> TYPE: DNA
<213> ORGANISM: Barnesiella

<400> SEQUENCE: 115

```
tgaggaatat tggtcaatgg agagatcct gaaccagcca agccgcgtga gggaagacgg     60
cactacgtgt tgtaaacctc ttttgccggg gaacaaaagc ggggacgcgt ccccgtccgc   120
gtgtacccgg agaaaaagca tcggctaact ccgtgcc                            157
```

<210> SEQ ID NO 116
<211> LENGTH: 157
<212> TYPE: DNA
<213> ORGANISM: Barnesiella

<400> SEQUENCE: 116

```
tgaggaatat tggtcaatgg gcgggagcct gaaccagcca agtcgcgtga gggaagacgg    60
ccctacgggt tgtaaacctc ttttgtcggg gagcaaagag cgccacgcgt ggcgagatga   120
gagtacccga agaaaaagca tcggctaact ccgtgcc                            157
```

<210> SEQ ID NO 117
<211> LENGTH: 158
<212> TYPE: DNA
<213> ORGANISM: Barnesiella

<400> SEQUENCE: 117

```
tgaggaatat tggtcaatgg gcgggagcct gaaccagcca agtcgcgtga gggaagacgg    60
ccctacgggt tgtaaacctc ttttgtcggg gagcaaagag cgccacgcgt ggcgagatga   120
gagtacccga agaaaaagac atcggctaac tccgtgcc                           158
```

<210> SEQ ID NO 118
<211> LENGTH: 157
<212> TYPE: DNA
<213> ORGANISM: Porphyromonadaceae

<400> SEQUENCE: 118

```
tgaggaatat tggtcaatgg gcgggagcct gaaccagcca agccgcgtga aggaagacgg    60
ccctacgggt tgtaaacttc ttttgttgca ggacaacacc ccggacgcgt ccgggcatga   120
gtgtatgcaa agaaaaagca tcggctaact ccgtgcc                            157
```

<210> SEQ ID NO 119
<211> LENGTH: 157
<212> TYPE: DNA
<213> ORGANISM: Bacteroidales

<400> SEQUENCE: 119

```
tgaggaatat tggtcaatgg gcgggagcct gaaccagcca agccgcgtga gggaataagg    60
ccctacgggt cgtaaacctc ttttgtcggg gaacaaaacc ggagacgagt ctccggctgc   120
gtgtacccga agaaaaagca tcggctaact ccgtgcc                            157
```

<210> SEQ ID NO 120
<211> LENGTH: 158
<212> TYPE: DNA
<213> ORGANISM: Bacteroidales

<400> SEQUENCE: 120
tgaggaatat tggtcaatgg gcgggagcct gaaccagcca agccgcgtga gggaagaagg      60
cgctcagcgt cgtaaacctc tttagccggg gaacaaagag ctgctcggga agcagcgttg     120
agcgtacccg gagaataagc atcggctaac tccgtgcc                             158

<210> SEQ ID NO 121
<211> LENGTH: 158
<212> TYPE: DNA
<213> ORGANISM: Porphyromonadaceae

<400> SEQUENCE: 121
tgaggaatat tggtcaatgg gcggaagcct gaaccagcca agtcgcgtga gggacgacgg      60
tcctacggat tgtaaacctc ttttgccggg gagcaatgcg cggtacgcgt accgcgacgg     120
agagtacccg gagaaaaagc atcggctaac tccgtgcc                             158

<210> SEQ ID NO 122
<211> LENGTH: 157
<212> TYPE: DNA
<213> ORGANISM: Porphyromonadaceae

<400> SEQUENCE: 122
tgaggaatat tggtcaatgg gcgagagcct gaaccagcca agtcgcgtga gggaagacgg      60
ccctacgggt tgtaaacctc ttttgtcggg gagcaaagag cgccacgcgt ggcgagatga     120
gagtacccga agaaaagaca tcggctaact ccgtgcc                              157

<210> SEQ ID NO 123
<211> LENGTH: 157
<212> TYPE: DNA
<213> ORGANISM: Barnesiella

<400> SEQUENCE: 123
tgaggaatat tggtcaatgg gcgcgagcct gaaccagcca agtcgcgtga gggaagacgg      60
ccctacgggt tgtaaacctc ttttgtcggg gagcaaggac tgccacgagt ggcagggcga     120
gagtacccga agaaaagca tcggctaact ccgtgcc                               157

<210> SEQ ID NO 124
<211> LENGTH: 157
<212> TYPE: DNA
<213> ORGANISM: Porphyromonadaceae

<400> SEQUENCE: 124
tgaggaatat tggtcaatgg gcgggagcct gaaccagcca agtcgcgtga gggaagacgg      60
tcttacggat tgtaaacctc ttttgccggg gagcaaaggg cgccacgcgt ggcgtttcga     120
gagtacccgg agaaaagca tcggctaact ccgtgcc                               157

<210> SEQ ID NO 125
<211> LENGTH: 157
<212> TYPE: DNA
<213> ORGANISM: Porphyromonadaceae

<400> SEQUENCE: 125
tgaggaatat tggtcaatgg ccgagaggct gaaccagcca agtcgcgtga gggaagacgg      60
tcctatggat tgtaaacctc ttttgtcggg gagcaaaagg cgtcacgtgt gacgctatga     120
gagtacccga agaaaagca tcggctaact ccgtgcc                               157

<210> SEQ ID NO 126
<211> LENGTH: 157
<212> TYPE: DNA
<213> ORGANISM: Bacteroidales

<400> SEQUENCE: 126
tgaggaatat tggtcaatgg ccggaaggct gaaccagcca agccgcgtga gggaggaagg      60
cgcagagcgt cgcagacctc ttttgccggg ggacaaaagg ccggactcgt ccggtcctga    120
gggtacccgg agaaaaagca tcggctaact ccgtgcc                             157

<210> SEQ ID NO 127
<211> LENGTH: 158
<212> TYPE: DNA
<213> ORGANISM: Barnesiella

<400> SEQUENCE: 127
tgaggaatat tggtcaatgg gcgcgagcct gaaccagcca agtcgcgtga gggatgacgg      60
ccctacgggt tgtaaaccct ttttgtcggg gagcaaattc cgttacgtgt aacggagtcg    120
agagtacccg aagaaaaagc atcggctaac tccgtgcc                            158

<210> SEQ ID NO 128
<211> LENGTH: 158
<212> TYPE: DNA
<213> ORGANISM: Porphyromonadaceae

<400> SEQUENCE: 128
tgaggaatat tggtcaatgg gcggaagcct gaaccagcca agtcgcgtga gggaagacgg      60
tcctatggat tgtaaaccct ttttgcaggg gagcaaggca cggtacgtgt accgtgaagg    120
agagtaccct gagaaaaagc atcggctaac tccgtgcc                            158

<210> SEQ ID NO 129
<211> LENGTH: 158
<212> TYPE: DNA
<213> ORGANISM: Porphyromonadaceae

<400> SEQUENCE: 129
tgaggaatat tggtcaatgg gcggaagcct gaaccagcca agtcgcgtga gggaagacgg      60
tcctatggat tgtaaaccct ttttgtcggg gagcaaagcc gctcacgtgt gagcggaagg    120
agagtacccg aagaaaaagc atcggctaac tccgtgcc                            158

<210> SEQ ID NO 130
<211> LENGTH: 158
<212> TYPE: DNA
<213> ORGANISM: Porphyromonadaceae

<400> SEQUENCE: 130
tgaggaatat tggtcaatgg gcggaagcct gaaccagcca agtcgcgtga gggaggacgg      60
tcctatggat tgtaaaccct ttttgtcggg gagcaaagcc gctcacgtgt gagcggaagg    120
agagtacccg aagaaaaagc atcggctaac tccgtgcc                            158

<210> SEQ ID NO 131
<211> LENGTH: 157
<212> TYPE: DNA
<213> ORGANISM: Barnesiella

<400> SEQUENCE: 131
tgaggaatat tggtcaatgg ccgaagggct gaaccagcca agtcgcgtga gggaagacgg      60

```
ccctacgggt tgtaaacctc ttttgccggg gagcaaaggc ggtcactggt gaccggatga    120
gagtacccgg agaaaaagca tcggctaact ccgtgcc                            157
```

<210> SEQ ID NO 132
<211> LENGTH: 158
<212> TYPE: DNA
<213> ORGANISM: Porphyromonadaceae

<400> SEQUENCE: 132

```
tgaggaatat tggtcaatgg gcgagagcct gaaccagcca agtcgcgtga gggaagacgg    60
tcctatggat tgtaaacctc ttttgtcagg gagcaaggag ggccacgagt ggcgcttcgg   120
agagtacctg aagaaaaagc atcggctaac tccgtgcc                           158
```

<210> SEQ ID NO 133
<211> LENGTH: 158
<212> TYPE: DNA
<213> ORGANISM: Barnesiella

<400> SEQUENCE: 133

```
tgaggaatat tggtcaatgg ccgagaggct gaaccagcca agtcgcgtga gggaagacgg    60
ccctacgggt tgtaaacctc ttttgtcggg gagcaaacag cgcaacgcgc ttgcgcattg   120
agagtacccg aagaaaaagc atcggctaac tccgtgcc                           158
```

<210> SEQ ID NO 134
<211> LENGTH: 157
<212> TYPE: DNA
<213> ORGANISM: Barnesiella

<400> SEQUENCE: 134

```
tgaggaatat tggtcaatgg gcgagagcct gaaccagcca agtcgcgtga gggaagacgg    60
ccctacgggt tgtaaacctc ttttgtcggg gagcaaagag cgccacgcgt ggcgagatga   120
gagtacccga agaaaaagca tcggctaact ccgtgcc                            157
```

<210> SEQ ID NO 135
<211> LENGTH: 157
<212> TYPE: DNA
<213> ORGANISM: Porphyromonadaceae

<400> SEQUENCE: 135

```
tgaggaatat tggtcaatgg gcgagagcct gaaccagcca agtcgcgtga gggaagacgg    60
ccctatgggt tgtaaacctc ttttgccggg gagcaaagaa ccgcacgtgt gcggtctgga   120
gagtacccgg agaaaaagca tcggctaact ccgtgcc                            157
```

<210> SEQ ID NO 136
<211> LENGTH: 158
<212> TYPE: DNA
<213> ORGANISM: Porphyromonadaceae

<400> SEQUENCE: 136

```
tgaggaatat tggtcaatgg gcggaagcct gaaccagcca agtcgcgtga gggaataagg    60
ccctaagggt cgtaaacctc ttttgccggg gagcaatggt tcgcttgcga gcggacaggg   120
agagtacccg gagaaaaagc atcggctaac tccgtgcc                           158
```

<210> SEQ ID NO 137
<211> LENGTH: 157
<212> TYPE: DNA

<213> ORGANISM: Barnesiella

<400> SEQUENCE: 137

| tgaggaatat tggtcaatgg ccgtaaggct gaaccagcca agtcgcgtga gggaagacgg | 60 |
| cccctacgggt tgtaaacctc ttttgccggg gagcaaaagg cgccacgcgt ggcgtttcga | 120 |
| gagtacccgg agaaaaagca tcggctaact ccgtgcc | 157 |

<210> SEQ ID NO 138
<211> LENGTH: 158
<212> TYPE: DNA
<213> ORGANISM: Barnesiella

<400> SEQUENCE: 138

| tgaggaatat tggtcaatgg gcgtaagcct gaaccagcca agtcgcgtga gggaagacgg | 60 |
| ccctatgggt tgtaaacctc ttttgtcggg gagcaaagcc gcccacgtgt gggcggaagg | 120 |
| agagtacccg aagaaaaagc atcggctaac tccgtgcc | 158 |

<210> SEQ ID NO 139
<211> LENGTH: 158
<212> TYPE: DNA
<213> ORGANISM: Barnesiella

<400> SEQUENCE: 139

| tgaggaatat tggtcaatgg gcgtaagcct gaaccagcca agtcgcgtga gggaagacgg | 60 |
| ccctatgggt tgtaaacctc ttttgtcggg gagcaaagcc gcccacgagt gggcggaagg | 120 |
| agagtacccg aagaaaaagc atcggctaac tccgtgcc | 158 |

<210> SEQ ID NO 140
<211> LENGTH: 159
<212> TYPE: DNA
<213> ORGANISM: Porphyromonadaceae

<400> SEQUENCE: 140

| tgaggaatat tggtcaatgg gcgtaagcct gaaccagcca agtcgcgtga gggaagacgg | 60 |
| ccctatgggt tgtaaacctc ttttgtcggg gagcaaagcc gcccacgagt gggcggaagg | 120 |
| agagtacccg aagaaaaaga catcggctaa ctccgtgcc | 159 |

<210> SEQ ID NO 141
<211> LENGTH: 158
<212> TYPE: DNA
<213> ORGANISM: Porphyromonadaceae

<400> SEQUENCE: 141

| tgaggaatat tggtcaatgg gcgtaagcct gaaccagcca agtcgcgtga gggaagacgg | 60 |
| ccctatgggt tgtaaacctc ttttgtcggg gagcaaagcc gcccacgagt gggcggaagg | 120 |
| agagtacccg aagaaaagac atcggctaac tccgtgcc | 158 |

<210> SEQ ID NO 142
<211> LENGTH: 158
<212> TYPE: DNA
<213> ORGANISM: Porphyromonadaceae

<400> SEQUENCE: 142

| tgaggaatat tggtcaatgg gcggtagcct gaaccagcca agtcgcgtga gggaagacgg | 60 |
| tcctatggat tgtaaacctc ttttgccggg gagcaaggcc atgtacgtgt acgtggcctg | 120 |
| agagtacccg gagaaaaagc atcggctaac tccgtgcc | 158 |

<210> SEQ ID NO 143
<211> LENGTH: 158
<212> TYPE: DNA
<213> ORGANISM: porphyromonadaceae

<400> SEQUENCE: 143
tgaggaatat tggtcaatgg gcgcgagcct gaaccagcca agtcgcgtga gggaagacgg      60
tcctaaggat tgtaaacctc ttttgtcagg gagcaaggag cgccacgtgt ggcgcggcga     120
gagtacctga agaaaaagac atcggctaac tccgtgcc                             158

<210> SEQ ID NO 144
<211> LENGTH: 157
<212> TYPE: DNA
<213> ORGANISM: Porphyromonadaceae

<400> SEQUENCE: 144
tgaggaatat tggtcaatgg gcgcgagcct gaaccagcca agtcgcgtga gggaagacgg      60
tcctaaggat tgtaaacctc ttttgtcagg gagcaaggag cgccacgtgt ggcgcggcga     120
gagtacctga agaaaaagca tcggctaact ccgtgcc                              157

<210> SEQ ID NO 145
<211> LENGTH: 157
<212> TYPE: DNA
<213> ORGANISM: Porphyromonadaceae

<400> SEQUENCE: 145
tgaggaatat tggtcaatgg gcgagagcct gaaccagcca agtcgcgtga gggaagacag      60
tcctatggat tgtaaacctc ttttgccggg gagcaaagag cggcacgtgt gccgcgccga     120
gagtacccgg agaaaaagca tcggctaact ccgtgcc                              157

<210> SEQ ID NO 146
<211> LENGTH: 157
<212> TYPE: DNA
<213> ORGANISM: Butyricimonas

<400> SEQUENCE: 146
tgaggaatat tggtcaatgg gcgagagcct gaaccagcca agtcgcgtga gggaagacgg      60
tcctatggat tgtaaacctc ttttgccggg gagcaaagag cggcacgtgt gccgcgccga     120
gagtacccgg agaaaaagca tcggctaact ccgtgcc                              157

<210> SEQ ID NO 147
<211> LENGTH: 157
<212> TYPE: DNA
<213> ORGANISM: Porphyromonadaceae

<400> SEQUENCE: 147
tgaggaatat tggtcaatgg gcgagagcct gaaccagcca agtcgcgtga gggaagacgg      60
tcctatggat tgtaaacctc ttttgtcggg gagcaacgaa ggcacgtgtg ccagaagcga     120
gattacccga agaaaaagca tcggctaact ccgtgcc                              157

<210> SEQ ID NO 148
<211> LENGTH: 158
<212> TYPE: DNA
<213> ORGANISM: Porphyromonadaceae

<400> SEQUENCE: 148

```
tgaggaatat tggtcaatgg gcgagagcct gaaccagcca agtcgcgtga gggaagacgg      60
tcctatggat tgtaaacctc ttttgtcggg gagcaacgaa ggcacgtgtg ccagaagcga     120
gattacccga agaaaaagac atcggctaac tccgtgcc                            158
```

<210> SEQ ID NO 149
<211> LENGTH: 157
<212> TYPE: DNA
<213> ORGANISM: Porphyromonadaceae

<400> SEQUENCE: 149

```
tgaggaatat tggtcaatgg gcgagagcct gaaccagcca agtcgcgtga gggaagacgg      60
tcctatggat tgtaaacctc ttttgtcggg gagcaacgaa ggcacgtgtg cctgaagcga     120
gattacccga agaaaaagca tcggctaact ccgtgcc                             157
```

<210> SEQ ID NO 150
<211> LENGTH: 158
<212> TYPE: DNA
<213> ORGANISM: Porphyromonadaceae

<400> SEQUENCE: 150

```
tgaggaatat tggtcaatgg gcgggagcct gaaccagcca agtcgcgtga gggaagacgg      60
tcctatggat tgtaaacctc ttttgtcggg gagcaaagag gccacgtgtg gtcaaaagcg     120
agagtacccg aagaaaaagc atcggctaac tccgtgcc                            158
```

<210> SEQ ID NO 151
<211> LENGTH: 159
<212> TYPE: DNA
<213> ORGANISM: Porphyromonadaceae

<400> SEQUENCE: 151

```
tgaggaatat tggtcaatgg gcgggagcct gaaccagcca agtcgcgtga gggaagacgg      60
tcctatggat tgtaaacctc ttttgtcggg gagcaaagag gccacgtgtg gtcaaaagcg     120
agagtacccg aagaaaaaga catcggctaa ctccgtgcc                           159
```

<210> SEQ ID NO 152
<211> LENGTH: 157
<212> TYPE: DNA
<213> ORGANISM: Porphyromonadaceae

<400> SEQUENCE: 152

```
tgaggaatat tggtcaatgg gcggaagcct gaaccagcca agtcgcgtga gggaagacgg      60
tcctatggat tgtaaacctc ttttgtcggg gagcaaggat ccgcacgagt gcggaggcga     120
gagtacccga agaaaaagca tcggctaact ccgtgcc                             157
```

<210> SEQ ID NO 153
<211> LENGTH: 158
<212> TYPE: DNA
<213> ORGANISM: Porphyromonadaceae

<400> SEQUENCE: 153

```
tgaggaatat tggtcaatgg gcggaagcct gaaccagcca agtcgcgtga gggaagacgg      60
tcctatggat tgtaaacctc ttttgtcggg gagcaaggat ccgcacgagt gcggaggcga     120
gagtacccga agaaaaagac atcggctaac tccgtgcc                            158
```

<210> SEQ ID NO 154
<211> LENGTH: 157

```
<212> TYPE: DNA
<213> ORGANISM: Butyricimonas

<400> SEQUENCE: 154
tgaggaatat tggtcaatgg gcgagagcct gaaccagcca agtcgcgtga gggaagaatg    60
gtctatggcc tgtaaacctc ttttgtcagg gaagaataag gatgacgagt cattcgatgc   120
cagtacttga cgaataagca tcggctaact ccgtgcc                             157

<210> SEQ ID NO 155
<211> LENGTH: 157
<212> TYPE: DNA
<213> ORGANISM: Alistipes

<400> SEQUENCE: 155
tgaggaatat tggtcaatgg acgcaagtct gaaccagcca tgccgcgtgc aggaagacgg    60
ctctatgagt tgtaaactgc ttttgtacga gggtaaaccc ggatacgtgt atccggctga   120
aagtatcgta cgaataagga tcggctaact ccgtgcc                             157

<210> SEQ ID NO 156
<211> LENGTH: 162
<212> TYPE: DNA
<213> ORGANISM: bacterium

<400> SEQUENCE: 156
ctaaggatat tccgcaacgg gcggaagccc ggcggagcga cgccgcgtgg acgaggaagg    60
ccggaaggtt gcagagtcct tttgcggggg aagaaggagc gcggaggga atgccgcggc   120 ggcgaccgaa ccccgcgaat aagggcggc taattacgtg cc                        162

<210> SEQ ID NO 157
<211> LENGTH: 155
<212> TYPE: DNA
<213> ORGANISM: Bifidobacterium

<400> SEQUENCE: 157
tggggaatat tgcacaatgg gcgcaagcct gatgcagcga cgccgcgtgc gggatggagg    60
ccttcgggtt gtaaaccgct tttgttcaag ggcaaggcac ggcttcgggc cgtgttgagt   120
ggattgttcg aataagcacc ggctaactac gtgcc                               155

<210> SEQ ID NO 158
<211> LENGTH: 137
<212> TYPE: DNA
<213> ORGANISM: Lachnospiraceae

<400> SEQUENCE: 158
tggggaatat tgcacaatgg ggggaaccct gatgcagcga cgccgcgtgg gtgaagaagt    60
atttcggtat gtaaagccct atcagcaggg aagaaaaga cggtacctga ctaagaagcc   120
ccggctaact acgtgcc                                                   137

<210> SEQ ID NO 159
<211> LENGTH: 137
<212> TYPE: DNA
<213> ORGANISM: Hespellia

<400> SEQUENCE: 159
tggggaatat tgcacaatgg gggaaaccct gatgcagcga cgccgcgtga aggaagaagt    60
atttcggtat gtaaacttct atcagcaggg aagaaaatga cggtatctga ctaagaagcc   120
```

```
ccggctaact acgtgcc                                                137
```

```
<210> SEQ ID NO 160
<211> LENGTH: 137
<212> TYPE: DNA
<213> ORGANISM: Marvinbryantia

<400> SEQUENCE: 160
tgggggatat tgcacaatgg gggaaaccct gatgcagcga cgccgcgtgg gtgaagaagt    60
atttcggtat gtaaagccct atcagcaggg aagaaaatga cagtacctga ataagaagcc   120
ccggctaact acgtgcc                                                 137
```

```
<210> SEQ ID NO 161
<211> LENGTH: 138
<212> TYPE: DNA
<213> ORGANISM: Lachnospiraceae

<400> SEQUENCE: 161 tggggatat tgcacaatgg ggggaaccct gatgcagcga cgccgcgtgg gtgaagaagt     60
atttcggtat gtaaagccct atcagcaggg aagaaagaag acggtacctg agtaagaagc   120
cccggctaac tacgtgcc                                                138
```

```
<210> SEQ ID NO 162
<211> LENGTH: 139
<212> TYPE: DNA
<213> ORGANISM: Lachnospiraceae

<400> SEQUENCE: 162
tggggagtat tgcacaatgg gggaaacccg tgatgcagcg acgccgcgtg agtgaagaag    60
tatttcggta tgtaaagctc tatcagcagg gaagaaaata gacggtacct gactaagaag   120
ccccggctaa ctacgtgcc                                               139
```

```
<210> SEQ ID NO 163
<211> LENGTH: 140
<212> TYPE: DNA
<213> ORGANISM: Lachnospiraceae

<400> SEQUENCE: 163
tgggggatat tggacaatgg ggggaaccct gatccagcga cgccgcgtga gtgaagaagt    60
atttcggtat gtaaagctct atcagcaggg aagaaagaaa tgacggtacc tgaccaagaa   120
gccccggcta actacgtgcc                                              140
```

```
<210> SEQ ID NO 164
<211> LENGTH: 142
<212> TYPE: DNA
<213> ORGANISM: Lachnospiraceae

<400> SEQUENCE: 164
tggggaatat tgcacaatgg ggggaaccct gatgcagcga cgccgcgtga gtgaagaagt    60
aattcgttac gtaaagctct atcagcaggg aagaaaaaga aatgacggta cctgattaag   120
aagccccggc taactacgtg cc                                           142
```

```
<210> SEQ ID NO 165
<211> LENGTH: 138
<212> TYPE: DNA
<213> ORGANISM: Lachnospiraceae

<400> SEQUENCE: 165
```

```
tggggaatat tgcacaatgg ggggaacccT gatgcagcaa tgccgcgtga gtgaagaagt    60
atttcggtat gtaaagctct atcagcaggg aagaaaaaag acggtacctg actaagaagc   120
cccggctaac tacgtgcc                                                 138
```

<210> SEQ ID NO 166
<211> LENGTH: 138
<212> TYPE: DNA
<213> ORGANISM: Lachnospiraceae

<400> SEQUENCE: 166

```
tggggaatat tgcacaatgg gggaaaccct gatgcagcaa tgccgcgtga gtgaagaagt    60
atttcggtat gtaaagctct atcagcaggg aagaaaaaag acggtacctg actaagaagc   120
cccggctaac tacgtgcc                                                 138
```

<210> SEQ ID NO 167
<211> LENGTH: 139
<212> TYPE: DNA
<213> ORGANISM: Lachnospiraceae

<400> SEQUENCE: 167

```
tggggaatat tgcacaatgg aggaaactct gatgcagcga cgccgcgtga gtgaagaagt    60
aattcgttac gtaaagctct atcagcaggg aagaaaaaat gacggtacct gactaagaag   120
caccggctaa atacgtgcc                                                139
```

<210> SEQ ID NO 168
<211> LENGTH: 139
<212> TYPE: DNA
<213> ORGANISM: Lachnospiraceae

<400> SEQUENCE: 168

```
tggggaatat tgcacaatgg aggaaactct gatgcagcga cgccgcgtga gtgaagaagt    60
aattcgttac gtaaagctct atcagcaggg agaaaaaaat gacggtacct gactaagaag   120
caccggctaa atacgtgcc                                                139
```

<210> SEQ ID NO 169
<211> LENGTH: 137
<212> TYPE: DNA
<213> ORGANISM: Oribacterium

<400> SEQUENCE: 169

```
tggggatat tgcacaatgg gggaaaccct gatgcagcga cgccgcgtga gtgaagaagt     60
atttcggtat gtaaagctct atcagcaggg aagaagatga cagtacctga ctaagaagcc   120
ccggctaact acgtgcc                                                  137
```

<210> SEQ ID NO 170
<211> LENGTH: 137
<212> TYPE: DNA
<213> ORGANISM: Coprococcus

<400> SEQUENCE: 170

```
tggggaatat tgcacaatgg ggggaaccct gatgcagcaa cgccgcgtga gtgaagaagt    60
atttcggtat gtaaagctct atcagcaggg aagaaaatga cggtacctga ctaagaagct   120
ccggctaaat acgtgcc                                                  137
```

<210> SEQ ID NO 171

```
<211> LENGTH: 137
<212> TYPE: DNA
<213> ORGANISM: Ruminococcus

<400> SEQUENCE: 171
tggggaatat tgcacaatgg gggaaaccct gatgcagcga tgccgcgtgg aggaagaagg      60
ttttcggatt gtaaactcct gtcttaaagg acgataatga cggtacttta ggaggaagct     120
ccggctaact acgtgcc                                                    137

<210> SEQ ID NO 172
<211> LENGTH: 138
<212> TYPE: DNA
<213> ORGANISM: Roseburia

<400> SEQUENCE: 172
tggggaatat tgcacaatgg gcgcaagcct gatgcagcga cgccgcgtga gtgaggaagt      60
atttcggtat gtaaagctct atcagcaggg aagaagaatg acggtacctg actaagaagc     120
accggctaaa tacgtgcc                                                   138

<210> SEQ ID NO 173
<211> LENGTH: 137
<212> TYPE: DNA
<213> ORGANISM: Lachnospiraceae

<400> SEQUENCE: 173
tggggaatat tgcacaatgg agggaactct gatgcagcga cgccgcgtga gtgaagaagt      60
aattcgttat gtaaagctct gtcagcaggg agaaagtga cggtacctga aaagaagct      120 ccggctaaat acgtgcc                                                    137

<210> SEQ ID NO 174
<211> LENGTH: 137
<212> TYPE: DNA
<213> ORGANISM: Lachnospiraceae

<400> SEQUENCE: 174
tggggaatat tgcacaatgg gggaaaccct gatgcagcga cgccgcgtga gtgaagaaat      60
atttcggtat gtaaagctct atcagcaggg aagaaaatga cggtacctga gtaagaagcc     120
ccggctaact acgtgcc                                                    137

<210> SEQ ID NO 175
<211> LENGTH: 138
<212> TYPE: DNA
<213> ORGANISM: Lachnospiraceae

<400> SEQUENCE: 175
tggggaatat tgcacaatgg gggaaaccct gatgcagcga cgccgcgtga gtgaagaagt      60
aattcgttat gtaaagctct atcagcaagg aagaaaaaag acggtacttg actaagaagc     120
cccggctaaa tacgtgcc                                                   138

<210> SEQ ID NO 176
<211> LENGTH: 137
<212> TYPE: DNA
<213> ORGANISM: Lachnospiraceae

<400> SEQUENCE: 176
tggggaatat tgcacaatgg gggaaaccct gatgcagcga cgccgcgtgg gtgaagaagt      60
atttcggtat gtaaagccct atcagcaggg aagaagatga cagtacctga ctaagaagcc     120
```

```
ccggctaact acgtgcc                                                    137

<210> SEQ ID NO 177
<211> LENGTH: 137
<212> TYPE: DNA
<213> ORGANISM: Lachnospiraceae

<400> SEQUENCE: 177
tgggggatat tgcacaatgg ggggaaccct gatgcagcga cgccgcgtgg gtgaaggagt      60
actccggtat gtaaagccct atcggcaggg aagaagatga cggtacctga ctaagaagct     120
ccggctaaat acgtgcc                                                    137

<210> SEQ ID NO 178
<211> LENGTH: 137
<212> TYPE: DNA
<213> ORGANISM: Butyrivibrio

<400> SEQUENCE: 178 tggggatat tgcacaatgg gggaaccct gatgcagcga cgccgcgtga gtgaagaagt        60
atttcggtat gtaaagctct atcagcaggg aagaaagtga cagtacctga gtaagaagcc    120
ccggctaact acgtgcc                                                    137

<210> SEQ ID NO 179
<211> LENGTH: 140
<212> TYPE: DNA
<213> ORGANISM: Lachnospiraceae

<400> SEQUENCE: 179
tgggggatat tggacaatgg ggggaaccct gatccagcga cgccgcgtga gtgaagaagt      60
atctcggtat gtaaagctct atcagcaggg aagaaagaaa tgacggtacc tgagtaagaa    120
gccccggcta actacgtgcc                                                 140

<210> SEQ ID NO 180
<211> LENGTH: 140
<212> TYPE: DNA
<213> ORGANISM: Lachnospiraceae

<400> SEQUENCE: 180
tgggggatat tggacaatgg ggggaaccct gatccagcga cgccgcgtga gtgaagaagt      60
atctcggtat gtaaagctct gtcagcaggg aagaaagaaa tgacggtacc tgaccaagaa    120
gccccggcta actacgtgcc                                                 140

<210> SEQ ID NO 181
<211> LENGTH: 140
<212> TYPE: DNA
<213> ORGANISM: lachnospiraceae

<400> SEQUENCE: 181
tgggggatat tggacaatgg ggggaaccct gatccagcga cgccgcgtga gtgaagaagt      60
atttcggtat gtaaagctct gtcagcaggg aagaaagaaa tgacggtacc tgaagaagaa    120
gccccggcta actacgtgcc                                                 140

<210> SEQ ID NO 182
<211> LENGTH: 138
<212> TYPE: DNA
<213> ORGANISM: Lachnospiraceae
```

```
<400> SEQUENCE: 182
tgggggatat tgcacaatgg ggggaacccct gatgcagcga cgccgcgtgg gtgaaggagt    60
gcttcggcat gtaaagccct atcggcaggg aagaagaagg acggtacctg actaagaagc   120
cccggctaac tacgtgcc                                                  138

<210> SEQ ID NO 183
<211> LENGTH: 137
<212> TYPE: DNA
<213> ORGANISM: Lachnospiraceae

<400> SEQUENCE: 183
tgggggatat tgcacaatgg ggggaacccct gatgcagcga cgccgcgtgg gtgaagaagc    60
gccccggcgc gtaaagccct atcggcaggg aagaagatga cggtacctgg ctaagaagcc   120
ccggctaact acgtgcc                                                   137

<210> SEQ ID NO 184
<211> LENGTH: 135
<212> TYPE: DNA
<213> ORGANISM: Lachnospiraceae

<400> SEQUENCE: 184
ggggatattg cacaatgggg gaacccgtga tgcagcgacg ccgcgtgggt gaagaagcgc    60
cccggcgcgt aaagccctat cggcagggaa gaagatgacg gtacctggct aagaagcccc   120
ggctaactac gtgcc                                                    135

<210> SEQ ID NO 185
<211> LENGTH: 137
<212> TYPE: DNA
<213> ORGANISM: Lachnospiraceae

<400> SEQUENCE: 185
tggggaatat tgcacaatgg ggggaacccct gatgcagcga cgccgcgtga gtgaagaagt    60
atttcggtat gtaaagctct atcagcagga acgaagaaga cggtacctga ctaagaagcc   120
ccggctaact acgtgcc                                                   137

<210> SEQ ID NO 186
<211> LENGTH: 138
<212> TYPE: DNA
<213> ORGANISM: Lachnospiraceae

<400> SEQUENCE: 186
tggggaatat tgcacaatgg ggaaaccct gatgcagcga cgccgcgtga gtgaagaagt    60
aattcgttac gtaaagctct atcagcagga aagaagaag acggtacctg actaagaagc   120
cccggctaac tacgtgcc                                                  138

<210> SEQ ID NO 187
<211> LENGTH: 137
<212> TYPE: DNA
<213> ORGANISM: Roseburia

<400> SEQUENCE: 187
tgggggatat tgcacaatgg ggggaacccct gatgcagcga cgccgcgtga gcgaagaagt    60
atttcggtat gtaaagctct atcagcgggg aagagaatga cggtacccga ctaagaagct   120
ccggctaaat acgtgcc                                                   137
```

```
<210> SEQ ID NO 188
<211> LENGTH: 137
<212> TYPE: DNA
<213> ORGANISM: Lachnospiraceae

<400> SEQUENCE: 188 tggggatat tgcacaatgg gggaaaccct gatgcagcga cgccgcgtga gtgaagaagt      60
atttcggtat gtaaagctct atcagcaggg aagaagatga cagtacctga ataagaagcc    120
ccggctaact acgtgcc                                                   137

<210> SEQ ID NO 189
<211> LENGTH: 137
<212> TYPE: DNA
<213> ORGANISM: Coprococcus

<400> SEQUENCE: 189
tggggaatat tgcacaatgg gggaaaccct gatgcagcga cgccgcgtga gcgaggaagt     60
atttcggtat gtaaagctct atcagcaggg aagaaaatga cggtacctga ctaagaagcc    120
ccggctaact acgtgcc                                                   137

<210> SEQ ID NO 190
<211> LENGTH: 138
<212> TYPE: DNA
<213> ORGANISM: bacterium

<400> SEQUENCE: 190
tggggaatat tgggcaatgg gcgcaagcct gacccagcaa cgccgcgtga gcgatgaagg     60
tcttcggatt gtaaagctct gtcgcagggg acgaagtatg acggtaccct gtaagaaagc    120
cccggcaaac tacgtgcc                                                  138

<210> SEQ ID NO 191
<211> LENGTH: 138
<212> TYPE: DNA
<213> ORGANISM: Lachnospiraceae

<400> SEQUENCE: 191
tggggaatat tgcacaatgg gggaaaccct gatgcagcga cgccgcgtga gcgaagaagt     60
atctcggtat gtaaagctct atcagcaggg aagaagaatg acggtacctg agtaagaagc    120
accggctaaa tacgtgcc                                                  138

<210> SEQ ID NO 192
<211> LENGTH: 137
<212> TYPE: DNA
<213> ORGANISM: Lachnospiraceae

<400> SEQUENCE: 192 tggggatat tgcacaatgg gggaaaccct gatgcagcga cgccgcgtga gcgaagaagt      60
atttcggtat gtaaagctct atcagcaggg aagaaaatga cggtacctga acaagaagct    120
ccggctaaat acgtgcc                                                   137

<210> SEQ ID NO 193
<211> LENGTH: 137
<212> TYPE: DNA
<213> ORGANISM: Coprococcus

<400> SEQUENCE: 193
tggggaatat tgcacaatgg ggggaaccct gatgcagcaa cgccgcgtga gtgaagaagt     60
```

```
atttcggtat gtaaagctct atcagcaggg aagaaaatga cggtacctga ctaagaagca    120
ccggctaaat acgtgcc                                                   137

<210> SEQ ID NO 194
<211> LENGTH: 138
<212> TYPE: DNA
<213> ORGANISM: Lachnospiraceae

<400> SEQUENCE: 194 tggggatat tgcacaatgg ggggaaccct gatgcagcga cgccgcgtga gtgaaggagt     60
acttcggtat gtaaagctct atcagcaggg aagaagcaag acgtacctg accaagaagc    120 cccggctaac tacgtgcc                                                  138

<210> SEQ ID NO 195
<211> LENGTH: 137
<212> TYPE: DNA
<213> ORGANISM: Lachnospiraceae

<400> SEQUENCE: 195
tggggaatat tgcacaatgg ggggaaccct gatgcagcga cgccgcgtga gcgaagaagt    60
atttcggtat gtaaagctct atcagcaggg aagaaaatga cggtacctga ctaagaagcc   120
ccggctaact acgtgcc                                                   137

<210> SEQ ID NO 196
<211> LENGTH: 140
<212> TYPE: DNA
<213> ORGANISM: bacterium

<400> SEQUENCE: 196
tggggaatat tgggcaatgg aggcaactct gacccagcaa cgccgcgtga gcgatgaagg    60
tcttcggatt gtaaagctct ttaagtgggg acgaagaaag tgactgtacc cacagaataa   120
gcctcggcta actacgtgcc                                                140

<210> SEQ ID NO 197
<211> LENGTH: 140
<212> TYPE: DNA
<213> ORGANISM: bacterium

<400> SEQUENCE: 197
tggggaatat tgggcaatgg aggaaactct gacccagcaa cgccgcgtga atgatgaagg    60
tcttcggatt gtaaagttct tttctaaggg aagaagaaag tgacggtacc ttaggaataa   120
gcctcggcta actacgtgcc                                                140

<210> SEQ ID NO 198
<211> LENGTH: 137
<212> TYPE: DNA
<213> ORGANISM: marvinbryantia

<400> SEQUENCE: 198
tggggaatat tgcacaatgg ggggaaccct gatgcagcaa tgccgcgtgg gtgaagaagt    60
accccggtat gtaaagccct atcagcaggg aagaaaatga cggtacctgg ctaagaagcc   120
ccggctaact acgtgcc                                                   137

<210> SEQ ID NO 199
<211> LENGTH: 137
<212> TYPE: DNA
<213> ORGANISM: Lachnospiraceae
```

<400> SEQUENCE: 199

```
tggggaatat tgcacaatgg gggaaaccct gatgcagcga cgccgcgtga gcgaagaagt    60
atttcggtat gtaaagctct atcagcaagg aagataatga cggtacttga ctaagaagct   120
ccggctaaat acgtgcc                                                  137
```

<210> SEQ ID NO 200
<211> LENGTH: 140
<212> TYPE: DNA
<213> ORGANISM: Lachnospiraceae

<400> SEQUENCE: 200

```
tggggaatat tgcacaatgg gcgaaagcct gatgcagcaa cgccgcgtga aggaagaagg    60
gtttcggctc gtaaacttct atcaacaggg acgaaggaag tgacggtacc tgaataagaa   120
gccccggcta actacgtgcc                                               140
```

<210> SEQ ID NO 201
<211> LENGTH: 137
<212> TYPE: DNA
<213> ORGANISM: Coprococcus

<400> SEQUENCE: 201

```
tggggaatat tgcacaatgg gggaaaccct gatgcagcaa cgccgcgtga gtgaagaagt    60
atttcggtat gtaaagctct atcagcaggg aagaaaatga cggtacctga ctaagaagct   120
ccggctaaat acgtgcc                                                  137
```

<210> SEQ ID NO 202
<211> LENGTH: 137
<212> TYPE: DNA
<213> ORGANISM: Ruminococcaceae

<400> SEQUENCE: 202

```
tggggaatat tgcacaatgg gggaaaccct gatgcagcga cgccgcgtgg aggaagaagg    60
ccctcgggtt gtaaactcct gtctttgggg acgataatga cggtacccaa ggaggaagcc   120
acggctaact acgtgcc                                                  137
```

<210> SEQ ID NO 203
<211> LENGTH: 137
<212> TYPE: DNA
<213> ORGANISM: Clostridiales

<400> SEQUENCE: 203

```
tggggaatat tgcacaatgg gggaaaccct gatgcagcga cgccgcgtgg aggaagaagg    60
ccctcgggtt gtaaactcct gtcttcgggg acgataatga cggtacccga ggaggaagcc   120
acggctaact acgtgcc                                                  137
```

<210> SEQ ID NO 204
<211> LENGTH: 137
<212> TYPE: DNA
<213> ORGANISM: Clostridiales

<400> SEQUENCE: 204

```
tgggggatat tgcacaatgg ggggaaccct gatgcagcga cgccgcgtga gcgaagaaga    60
tcttcggatt gtaaagctct gtcttagggg acgatgatga cggtaccctg agaggaagcc   120
acggctaact acgtgcc                                                  137
```

```
<210> SEQ ID NO 205
<211> LENGTH: 138
<212> TYPE: DNA
<213> ORGANISM: Ruminococcaceae

<400> SEQUENCE: 205
tgggggatat tgcgcaatgg gggcaaccct gacgcagcaa cgccgcgtga aggatgaagg      60
ttttcggatt gtaaacttct tttcttaagg acgaaatttg acggtactta aggaataagc     120
tccggctaac tacgtgcc                                                   138

<210> SEQ ID NO 206
<211> LENGTH: 140
<212> TYPE: DNA
<213> ORGANISM: Oscillibacter

<400> SEQUENCE: 206
tggggaatat tgggcaatgg gcgcaagcct gacccagcaa cgccgcgtga aggaagaagg      60
ctttcgggtt gtaaacttct tttaagaggg acgaaggaag tgacggtacc tcttgaataa     120
gccacggcta actacgtgcc                                                 140

<210> SEQ ID NO 207
<211> LENGTH: 137
<212> TYPE: DNA
<213> ORGANISM: Clostridiales

<400> SEQUENCE: 207
tgagggatat tggtcaatgg gggaaaccct gaaccagcaa cgccgcgtga gggaagacgg      60
tcttcggatt gtaaacctttt gtcctctgtg aagataatga cggtagcaga ggaggaagct    120
ccggctaact acgtgcc                                                    137

<210> SEQ ID NO 208
<211> LENGTH: 137
<212> TYPE: DNA
<213> ORGANISM: Clostridiales

<400> SEQUENCE: 208
tgggggatat tgcacaatgg gggaaaccct gatgcagcaa cgccgcgtga aggaagaagg      60
tcttcggatt gtaaactttt gtccttggtg aagataatga cggtagccaa ggaggaagct     120
ccggctaact acgtgcc                                                    137

<210> SEQ ID NO 209
<211> LENGTH: 139
<212> TYPE: DNA
<213> ORGANISM: Oscillibacter

<400> SEQUENCE: 209
tggggaatat tgggcaatgg gcgcaagcct gacccagcaa cgccgcgtga aggaagaagg      60
ctttcgggtt gtaaacttct tttgtcaggg aagagcagaa gacggtacct gacgaataag     120
ccacggctaa ctacgtgcc                                                  139

<210> SEQ ID NO 210
<211> LENGTH: 138
<212> TYPE: DNA
<213> ORGANISM: Clostridia

<400> SEQUENCE: 210
tgggggatat tgcacaatgg gggaaaccct gatgcagcga cgccgcgtgt gggaagacgg      60
```
tcctctggat tgtaaaccac tgtccccagg gacgaagatg acggtacctg gggaggaagc    120
tccggctaac tacgtgcc                                                 138

<210> SEQ ID NO 211
<211> LENGTH: 138
<212> TYPE: DNA
<213> ORGANISM: Ruminococcaceae

<400> SEQUENCE: 211
tggggaatat tgcacaatgg ggggaaccct gatgcagcga tgccgcgtgg aggaagaagg    60
ttttcggatt gtaaactcct gtcgacagga agaaaaagg actgtacctg tcaagaaagc     120
tccggctaac tacgtgcc                                                 138

<210> SEQ ID NO 212
<211> LENGTH: 137
<212> TYPE: DNA
<213> ORGANISM: Ruminococcus

<400> SEQUENCE: 212
tggggaatat tgcacaatgg ggggaaccct gatgcagcga tgccgcgtgg aggaagaagg    60
ttttcggatt gtaaactcct gtcttaaagg acgataatga cggtacttta ggaggaagct    120
ccggctaact acgtgcc                                                  137

<210> SEQ ID NO 213
<211> LENGTH: 137
<212> TYPE: DNA
<213> ORGANISM: Ruminococcaceae

<400> SEQUENCE: 213
tggggaatat tgcacaatgg aggaaactct gatgcagcga tgccgcgtga gggaagaagg    60
ttttcggatt gtaaacctct gtcttaaggg acgataatga cggtacctta ggaggaagct    120
ccggctaact acgtgcc                                                  137

<210> SEQ ID NO 214
<211> LENGTH: 137
<212> TYPE: DNA
<213> ORGANISM: Ruminococcaceae

<400> SEQUENCE: 214 tggggatat tgcacaatgg agggaactct gatgcagcga tgccgcgtga gggaagaagg     60
ttttcggatt gtaaacctct gtggacagag acgataatga cggtatctgt caaggaagcc    120
acggctaact acgtgcc                                                  137

<210> SEQ ID NO 215
<211> LENGTH: 137
<212> TYPE: DNA
<213> ORGANISM: Ruminococcaceae

<400> SEQUENCE: 215 tggggatat tgcacaatgg gggaaccct gatgcagcga tgccgcgtga gggaagaagg      60
ttttcggatt gtaaacctct gtggaggggg acgataatga cggtaccct taaggaagcc     120 acggctaact acgtgcc                                                  137

<210> SEQ ID NO 216
<211> LENGTH: 137
<212> TYPE: DNA

<213> ORGANISM: Ruminococcaceae

<400> SEQUENCE: 216

```
tgggggatat tggacaatgg gggaaaccct tatccagcga cgccgcgtga gggaagaagg    60
ttttcggatt gtaaacctct gtcagcgggg acgataatga cggtacccgc ggaggaagcc   120
acggctaact acgtgcc                                                  137
```

<210> SEQ ID NO 217
<211> LENGTH: 138
<212> TYPE: DNA
<213> ORGANISM: Fastidiosipila

<400> SEQUENCE: 217

```
tggggaatat tgggcaatgg gcgaaagcct gacccagcga cgccgcgtga aggaagacgg    60
tcttcggatt gtaaacttta gtactcaggg acgaagaaat gacggtacct gaggttaagc   120
cacggctaac tacgtgcc                                                 138
```

<210> SEQ ID NO 218
<211> LENGTH: 138
<212> TYPE: DNA
<213> ORGANISM: Ruminococcus

<400> SEQUENCE: 218

```
tgggggatat tgcgcaatgg gggaaaccct gacgcagcaa cgccgcgtga aggaagaagg    60
ttttcggatt gtaaacttct tttattaagg acgaaagatg acggtactta atgaataagc   120
tccggctaac tacgtgcc                                                 138
```

<210> SEQ ID NO 219
<211> LENGTH: 139
<212> TYPE: DNA
<213> ORGANISM: Oscillibacter

<400> SEQUENCE: 219

```
tggggaatat tgggcaatgg acgcaagtct gacccagcaa cgccgcgtga aggaagaagg    60
ctttcgggtt gtaaacttct tttgtcaggg aagagaagaa gacggtacct gacgaacaag   120
ccacggctaa ctacgtgcc                                                139
```

<210> SEQ ID NO 220
<211> LENGTH: 139
<212> TYPE: DNA
<213> ORGANISM: Oscillibacter

<400> SEQUENCE: 220

```
tggggaatat tgggcaatgg gcgcaagcct gacccagcaa cgccgcgtga aggaagaagg    60
ctttcgggtt gtaaacttct tttgacaggg aagagcagaa gacggtacct gtcgaataag   120
ccacggctaa ctacgtgcc                                                139
```

<210> SEQ ID NO 221
<211> LENGTH: 138
<212> TYPE: DNA
<213> ORGANISM: Ruminococcus

<400> SEQUENCE: 221

```
tgggggatat tgcgcaatgg gggcaaccct gacgcagcaa cgccgcgtga aggatgaagg    60
ttttcggatt gtaaacttct tttattaagg acgaattttg acggtactta atgaataagc   120
tccggctaac tacgtgcc                                                 138
```

<210> SEQ ID NO 222
<211> LENGTH: 139
<212> TYPE: DNA
<213> ORGANISM: Oscillibacter

<400> SEQUENCE: 222

```
tggggaatat tgggcaatgg gcgcaagcct gacccagcaa cgccgcgtga aggaagaagg    60
ctttcgggtt gtaaacttct tttaagaggg aagagcagaa gacggtacct cttgaataag   120
ctccggctaa ctacgtgcc                                                139
```

<210> SEQ ID NO 223
<211> LENGTH: 140
<212> TYPE: DNA
<213> ORGANISM: bacterium

<400> SEQUENCE: 223

```
tggggaatat tgggcaatgg gggaaaccct gacccagcaa cgccgcgtga gggaagaagg    60
ctttcgggtt gtaaacctct tttaccaggg acgaaggacg tgacggtacc tggagaaaaa   120
gcaacggcta actacgtgcc                                               140
```

<210> SEQ ID NO 224
<211> LENGTH: 140
<212> TYPE: DNA
<213> ORGANISM: Ruminococcaceae

<400> SEQUENCE: 224

```
tggggaatat tgggcaatgg gggaaaccct gacccagcaa cgccgcgtga aggaagaagg    60
ccttcgggtt gtaaacttct tttaccaggg acgaaggacg tgacggtacc tggagaaaaa   120
gcaacggcta actacgtgcc                                               140
```

<210> SEQ ID NO 225
<211> LENGTH: 140
<212> TYPE: DNA
<213> ORGANISM: Oscillibacter

<400> SEQUENCE: 225

```
tggggaatat tgggcaatgg gcgaaagcct gacccagcaa cgccgcgtga aggaagaagg    60
ccttcgggtt gtaaacttct tttaagaggg acgaagaaag tgacggtacc tcttgaataa   120
gccacggcta actacgtgcc                                               140
```

<210> SEQ ID NO 226
<211> LENGTH: 140
<212> TYPE: DNA
<213> ORGANISM: Fastidiosipila

<400> SEQUENCE: 226

```
tggggaatat tgggcaatgg gcgcaagcct gacccagcaa cgccgcgtga aggaagaagg    60
ctttcgggtt gtaaacttct tttgagaggg acgaaacaaa tgacggtacc tcttgaataa   120
gccacggcta actacgtgcc                                               140
```

<210> SEQ ID NO 227
<211> LENGTH: 140
<212> TYPE: DNA
<213> ORGANISM: Oscillibacter

<400> SEQUENCE: 227

```
tggggaatat tgggcaatgg gcggaagcct gacccagcaa cgccgcgtga aggaagaagg    60
ctttcgggtt gtaaacttct tttcttgggg acgaagaaag tgacggtacc caaggaataa   120
gccacggcta actacgtgcc                                                140
```

<210> SEQ ID NO 228
<211> LENGTH: 140
<212> TYPE: DNA
<213> ORGANISM: Oscillibacter

<400> SEQUENCE: 228

```
tggggaatat tgggcaatgg gcgcaagcct gacccagcaa cgccgcgtga aggaagaagg    60
ctttcgggtt gtaaacttct tttgaggggg acgaaggatg tgacggtacc ccttgaataa   120
gccacggcta actacgtgcc                                                140
```

<210> SEQ ID NO 229
<211> LENGTH: 140
<212> TYPE: DNA
<213> ORGANISM: Oscillibacter

<400> SEQUENCE: 229

```
tggggaatat tgggcaatgg gcgcaagcct gacccagcaa cgccgcgtga aggaagaagg    60
ctttcgggtt gtaaacttct tttcttgggg acgaagaaag tgacggtacc cgaggaataa   120
gccacggcta actacgtgcc                                                140
```

<210> SEQ ID NO 230
<211> LENGTH: 137
<212> TYPE: DNA
<213> ORGANISM: Marvinbryantia

<400> SEQUENCE: 230

```
tggggaatat tgcacaatgg gggaaaccct gatgcagcga cgccgcgtgg gtgaagaagt    60
atttcggtat gtaaagccct atcagcaggg aagatcatga cggtacctga ctaagaagcc   120
ccggctaact acgtgcc                                                   137
```

<210> SEQ ID NO 231
<211> LENGTH: 140
<212> TYPE: DNA
<213> ORGANISM: Oscillibacter

<400> SEQUENCE: 231

```
tggggaatat tgggcaatgg gcgcaagcct gacccagcaa cgccgcgtga aggaagaagg    60
ctttcgggtt gtaaacttct tttctgaggg acgaagcaag tgacggtacc ttaggaataa   120
gccacggcta actacgtgcc                                                140
```

<210> SEQ ID NO 232
<211> LENGTH: 139
<212> TYPE: DNA
<213> ORGANISM: Ruminococcaceae

<400> SEQUENCE: 232

```
tggggaatat tgggcaatgg gcgcaagcct gacccagcaa cgccgcgtga aggaagaagg    60
ctttcgggtt gtaaacttct tttgacaggg aagaggagaa gacggtacct gtcgaataag   120
ctccggctaa ctacgtgcc                                                 139
```

<210> SEQ ID NO 233
<211> LENGTH: 139

```
<212> TYPE: DNA
<213> ORGANISM: Ruminococcaceae

<400> SEQUENCE: 233
tggggaatat tgggcaatgg gcgcaagcct gacccagcaa cgccgcgtga aggaagaagg    60
ccctcgggtt gtaaacttct tttatcaggg acgaagaagt gacggtacct gatgaataag   120
ccacggctaa ctacgtgcc                                                139

<210> SEQ ID NO 234
<211> LENGTH: 138
<212> TYPE: DNA
<213> ORGANISM: Clostridiales

<400> SEQUENCE: 234
tggggaatat tgcgcaatgg gggaaaccct gacgcagcaa cgccgcgtga ttgaagaagg    60
ccttcgggtt gtaaagatct ttaatcgggg acgaattttg acggtacccg aagaataagc   120
tccggctaac tacgtgcc                                                 138

<210> SEQ ID NO 235
<211> LENGTH: 138
<212> TYPE: DNA
<213> ORGANISM: Clostridiales

<400> SEQUENCE: 235
tggggaatat tgcgcaatgg gggaaaccct gacgcagcaa cgccgcgtga ttgaagaagg    60
ccctcgggtt gtaaagatct ttaatcgggg acgaagaatg acggtacccg aagaataagc   120
tccggctaac tacgtgcc                                                 138

<210> SEQ ID NO 236
<211> LENGTH: 138
<212> TYPE: DNA
<213> ORGANISM: Clostridiales

<400> SEQUENCE: 236
tggggaatat tgcgcaatgg gggaaaccct gacgcagcaa cgccgcgtga gtgaagaagg    60
ccttcgggtt gtaaagctct ttaatcaggg acgaagaacg acggtacctg aagaataagc   120
tccggctaac tacgtgcc                                                 138

<210> SEQ ID NO 237
<211> LENGTH: 140
<212> TYPE: DNA
<213> ORGANISM: Firmicutes

<400> SEQUENCE: 237
tggggaatat tgggcaatgg gcgaaagcct gacccagcaa cgccgcgtga aggaagaagg    60
tcttcggatt gtaaacttct tttatcaggg acgaaggaag tgacggtacc tgatgaataa   120
gccacggcta actacgtgcc                                               140

<210> SEQ ID NO 238
<211> LENGTH: 137
<212> TYPE: DNA
<213> ORGANISM: bacterium

<400> SEQUENCE: 238
tcgggaatat tgcgcaatgg aggcaactct gacgcagtga cgccgcgtat aggaagaagg    60
ttttcggatt gtaaactatt gtccacaggg aagaaaagga ctgtacctgt gaagaaagct   120
```
ccggctaact acgtgcc 137

<210> SEQ ID NO 239
<211> LENGTH: 138
<212> TYPE: DNA
<213> ORGANISM: Firmicutes

<400> SEQUENCE: 239
tcgggaatat tgcgcaatgg aggaaactct gacgcagtga cgccgcgtat aggaagaagg    60
ttttcggatt gtaaactatt gtccacaggg aagataaaag actgtacctg tgaagaaagc   120
tccggctaac tacgtgcc                                                 138

<210> SEQ ID NO 240
<211> LENGTH: 138
<212> TYPE: DNA
<213> ORGANISM: bacterium

<400> SEQUENCE: 240
tcgggaatat tgcgcaatgg aggaaactct gacgcagtga cgccgcgtat aggaagaagg    60
ttttcggatt gtaaactatt gtcgataggg aagaaaaaag actgtaccta tcaagaaagc   120
tccggctaac tacgtgcc                                                 138

<210> SEQ ID NO 241
<211> LENGTH: 138
<212> TYPE: DNA
<213> ORGANISM: Clostridia

<400> SEQUENCE: 241
tcgggaatat tgcgcaatgg agggaactct gacgcagtga cgccgcgtat aggaagaagg    60
ttttcggatt gtaaactatt ttagtcaggg aagaaagcag acggtacctg aagaataagc   120
tccggctaac tacgtgcc                                                 138

<210> SEQ ID NO 242
<211> LENGTH: 138
<212> TYPE: DNA
<213> ORGANISM: bacterium

<400> SEQUENCE: 242
tcgggaatat tgcacaatgg aggaaactct gatgcagtga cgccgcgtgc aggaagaagg    60
ttttcggatt gtaaactgct ttagacaggg aagaaaaaag acagtacctg tagaataagc   120
tccggctaac tacgtgcc                                                 138

<210> SEQ ID NO 243
<211> LENGTH: 138
<212> TYPE: DNA
<213> ORGANISM: bacterium

<400> SEQUENCE: 243
tcgggaatat tgcgcaatgg aggaaactct gacgcagtga cgccgcgtat aggaagaagt    60
ttttcggaat gtaaactatt gtcgttaggg aagagaaagg acagtaccta aggaggaagc   120
tccggctaac tacgtgcc                                                 138

<210> SEQ ID NO 244
<211> LENGTH: 138
<212> TYPE: DNA
<213> ORGANISM: Clostridia

<400> SEQUENCE: 244

```
tcgggaatat tgcgcaatgg agggaactct gacgcagtga cgccgcgtat aggaagaagg    60
ttttcggatt gtaaactatt gtcgttaggg aagaaaaaag acagtaccta aggaggaagc   120
cccggctaac tatgtgcc                                                 138

<210> SEQ ID NO 245
<211> LENGTH: 138
<212> TYPE: DNA
<213> ORGANISM: bacterium

<400> SEQUENCE: 245
tcgggaatat tgcgcaatgg aggaaactct gacgcagtga cgccgcgtat aggaagaagg    60
tcttcggatt gtaaactatt gtcgttaggg aagagaaagg acagtaccta aggaggaagc   120
tccggctaac tacgtgcc                                                 138

<210> SEQ ID NO 246
<211> LENGTH: 140
<212> TYPE: DNA
<213> ORGANISM: bacterium

<400> SEQUENCE: 246
tcgggaatat tgcgcaatgg aggaaactct gacgcagtga cgccgcgtgc aggaagaagg    60
ttttcggatt gtaaactgct ttagacaggg aagaaacaaa tgacagtacc tgtagaataa   120
gctccggcta actacgtgcc                                               140

<210> SEQ ID NO 247
<211> LENGTH: 137
<212> TYPE: DNA
<213> ORGANISM: bacterium

<400> SEQUENCE: 247
tcgggaatat tgcgcaatgg aggaaactct gacgcagtga cgccgcgtat aggaagaagg    60
ttttcggatt gtaaactatt gtcgtgaggg aagaaattga cagtacctca ggaggaagct   120
ccggctaact atgtgcc                                                  137

<210> SEQ ID NO 248
<211> LENGTH: 138
<212> TYPE: DNA
<213> ORGANISM: bacterium

<400> SEQUENCE: 248
tcgggaatat tgcgcaatgg aggaaactct gacgcagtga cgccgcgtat aggaagaagg    60
ttttcggatt gtaaactatt gtcgttaggg aagagaaagg acagtaccta aggaggaagc   120
tccggctaac tacgtgcc                                                 138

<210> SEQ ID NO 249
<211> LENGTH: 140
<212> TYPE: DNA
<213> ORGANISM: bacterium

<400> SEQUENCE: 249
tcgggaatat tgcgcaatgg aggaaactct gacgcagtga cgccgcgtgc aggaagaagg    60
ttttcggatt gtaaactgct ttagacaggg aagaaagaaa tgacggtacc tgtagaataa   120
gctccggcta actacgtgcc                                               140

<210> SEQ ID NO 250
```

```
<211> LENGTH: 138
<212> TYPE: DNA
<213> ORGANISM: bacterium

<400> SEQUENCE: 250
tcgggaatat tgcgcaatgg aggaaactct gacgcagtga cgccgcgtat aggaagaagg      60
ttttcggatt gtaaactatt gtcgttaggg aagataaaag actgtaccta aggaggaagc     120
cccggctaac tatgtgcc                                                    138

<210> SEQ ID NO 251
<211> LENGTH: 138
<212> TYPE: DNA
<213> ORGANISM: bacterium

<400> SEQUENCE: 251
tcgggaatat tgcgcaatgg aggaaactct gacgcagtga cgccgcgtat aggaagaagt      60
ttttcggaat gtaaactatt gtcattaggg aagagaaagg acggtaccta aggaggaagc     120
cccggctaac tatgtgcc                                                    138

<210> SEQ ID NO 252
<211> LENGTH: 138
<212> TYPE: DNA
<213> ORGANISM: bacterium

<400> SEQUENCE: 252
tcgggaatat tgcgcaatgg aggaaactct gacgcagtga cgccgcgtat aggaagaagg      60
ttttcggatt gtaaactatt gtcgttaggg aagaaaaaag acagtaccta aggaggaagc     120
cccggctaac tatgtgcc                                                    138

<210> SEQ ID NO 253
<211> LENGTH: 139
<212> TYPE: DNA
<213> ORGANISM: bacterium

<400> SEQUENCE: 253
ttgggaatat tggacaatgg aggaaactct gatccagtga cgccgcgtga aggaagaagg      60
tcttcggatt gtaaacttat tttgtcaggg aagaataaat gactgtacct gaagaaaaag     120
caccggctaa ctacgtgcc                                                   139

<210> SEQ ID NO 254
<211> LENGTH: 140
<212> TYPE: DNA
<213> ORGANISM: Clostridiales

<400> SEQUENCE: 254
tggggaatat tgcgcaatgg gggaaaccct gacgcagcaa cgccgcgtgc aggaagaagg      60
tcttcggatt gtaaactgtt gtcgcagggg aagaagacag tgacggtacc ctgtgagaaa     120
gtcacggcta actacgtgcc                                                  140

<210> SEQ ID NO 255
<211> LENGTH: 139
<212> TYPE: DNA
<213> ORGANISM: bacterium

<400> SEQUENCE: 255
tggggaatat tgggcaatgg gcgaaagcct gacccagcaa cgccgcgtgg aggaagaagg      60
ttttcggatc gtaaactcct gtcctaagag acgaggaaga gacggtatct taggaggaag    120
```
ccccggctaa ctacgtgcc                                              139

<210> SEQ ID NO 256
<211> LENGTH: 140
<212> TYPE: DNA
<213> ORGANISM: bacterium

<400> SEQUENCE: 256
tggggaatat tgggcaatgg gcgaaagcct gacccagcaa cgccgcgtga gggaagaagg    60
ttttcggatt gtaaacctct gtcctaagtg acgaaggaag tgacggtagc ttaggaggaa   120
gccccggcta actacgtgcc                                              140

<210> SEQ ID NO 257
<211> LENGTH: 140
<212> TYPE: DNA
<213> ORGANISM: bacterium

<400> SEQUENCE: 257
tggggaatat tgggcaatgg gcgaaagcct tacccagcaa cgccgcgtga gggaagaagg    60
ttttcggatt gtaaacctct gtcctggggg acgaaggaag tgacggtacc ccgggaggaa   120
gccccggcta actacgtgcc                                              140

<210> SEQ ID NO 258
<211> LENGTH: 137
<212> TYPE: DNA
<213> ORGANISM: Clostridiales

<400> SEQUENCE: 258
tggggaatat tgggcaatgg gggaaaccct gacccagcaa cgccgcgtga aggaagaagg    60
ttttcggatc gtaaacttct atccttggtg aaaatgatga tggtagccaa gaaggaagcc   120
ccggctaact acgtgcc                                                 137

<210> SEQ ID NO 259
<211> LENGTH: 140
<212> TYPE: DNA
<213> ORGANISM: bacterium

<400> SEQUENCE: 259
tggggaatat tgggcaatgg gcgaaagcct gacccagcaa cgccgcgtga gggaagaagg    60
gtttcggctc gtaaacctct gtcctatggg acgaaggaag tgacggtacc ataggaggaa   120
gccccggcta actacgtgcc                                              140

<210> SEQ ID NO 260
<211> LENGTH: 137
<212> TYPE: DNA
<213> ORGANISM: Clostridiales

<400> SEQUENCE: 260
tggggaatat tgcacaatgg gcgaaagcct gatgcagcaa cgccgcgtga gcgaagaagg    60
tcttcggatc gtaaagctct gtccttgggg aagataatga cggtacccaa ggaggaagcc   120
ccggctaact acgtgcc                                                 137

<210> SEQ ID NO 261
<211> LENGTH: 140
<212> TYPE: DNA
<213> ORGANISM: bacterium

-continued

```
<400> SEQUENCE: 261
tggggaatat tgggcaatgg aggcaactct gacccagcaa cgccgcgtga atgaagaagg    60
tcctaggatt gtaaagttct tttatgatag acgaataaaa tgacggtata tcatgaataa   120
gccacggcta actacgtgcc                                                140

<210> SEQ ID NO 262
<211> LENGTH: 140
<212> TYPE: DNA
<213> ORGANISM: bacterium

<400> SEQUENCE: 262
tggggaatat tgggcaatgg aggcaactct gacccagcaa cgccgcgtga atgaagaagg    60
ccttcgggtt gtaaagttct ttaatggggg acgaagaaag tgacggtacc ccaagaataa   120
gccacggcta actacgtgcc                                                140

<210> SEQ ID NO 263
<211> LENGTH: 137
<212> TYPE: DNA
<213> ORGANISM: Lachnospiraceae

<400> SEQUENCE: 263
tgggggatat tgcacaatgg gggaaaccct gatgcagcga cgccgcgtga gtgaagaagt    60
atttcggtat gtaaagctct atcagcaggg aagaaaatga cggtacctga ctaagaagcc   120
ccggctaact acgtgcc                                                   137

<210> SEQ ID NO 264
<211> LENGTH: 163
<212> TYPE: DNA
<213> ORGANISM: Firmicutes

<400> SEQUENCE: 264
ttaggaatat tcgtcaatgg gggaaaccct gaacgagcaa tgccgcgtga gtgatgacgg    60
tctttatgat tgtaaaactc tgttgtaagg aaagaaccct tatcatagga aatgatgata   120
agttgacggt accttaccag aaagccccgg ctaactacgt gcc                      163

<210> SEQ ID NO 265
<211> LENGTH: 146
<212> TYPE: DNA
<213> ORGANISM: Anaeroplasma

<400> SEQUENCE: 265
tagggaattt tcggcaatgg ggggaaccct gaccgagcaa cgccgcgtga acgaagaagt    60
tattcgtaat gtaaagttct tttatcaggg aagaaaagaa gggaattgac ggtacctgat   120
gaataagctc cggctaacta cgtgcc                                         146

<210> SEQ ID NO 266
<211> LENGTH: 162
<212> TYPE: DNA
<213> ORGANISM: Clostridiales

<400> SEQUENCE: 266
tggggaatct tccgcaatgg gcgaaagcct gacggagcga cgccgcgtga gtgaagaagg    60
tcttcggacc gtaaagctct tttgttgcag gcgaaaggac ttaagaggaa atgcttaagt   120
taagacggta tggaacgaat aagccacggc taactacgtg cc                       162
```

```
<210> SEQ ID NO 267
<211> LENGTH: 137
<212> TYPE: DNA
<213> ORGANISM: incertae sedis

<400> SEQUENCE: 267
tagggaatct ttcacaatgg gcgaaagcct gatggagcaa cgccgcgtgc aggatgaagg      60
ccttcgggtt gtaaactgct tttataagcg agaaatatga tggtaactta tgaataagga     120
tcggctaact acgtgcc                                                    137

<210> SEQ ID NO 268
<211> LENGTH: 140
<212> TYPE: DNA
<213> ORGANISM: bacterium

<400> SEQUENCE: 268
tggggaattt tggacaatgg acggaagtct gatccagcaa cgcagcgtga aggacgaagg      60
ttctcggatt gtaaacttct tttgcagggg aagaaaaaaa tgacggtacc ctgtgaataa     120
gccacggcta actacgtgcc                                                 140
```